US 6,610,711 B2

(12) United States Patent
Armer et al.

(10) Patent No.: US 6,610,711 B2
(45) Date of Patent: Aug. 26, 2003

(54) 4-PHENYLPIPERIDINES FOR THE TREATMENT OF PRURITIC DERMATOSES

(75) Inventors: Richard Edward Armer, Sandwich (GB); Christopher James Dutton, Sandwich (GB); David Morris Gethin, Sandwich (GB); Stephen Paul Gibson, Sandwich (GB); Julian Duncan Smith, Sandwich (GB); Ivan Tommasini, Sandwich (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/646,255

(22) PCT Filed: May 17, 1999

(86) PCT No.: PCT/IB99/00886

§ 371 (c)(1),
(2), (4) Date: May 11, 2000

(87) PCT Pub. No.: WO99/59971

PCT Pub. Date: Nov. 25, 1999

(65) Prior Publication Data

US 2003/0078282 A1 Apr. 24, 2003

(30) Foreign Application Priority Data

May 18, 1998 (GB) .............................................. 9810671

(51) Int. Cl.[7] ..................... A61K 31/445; C07D 211/26

(52) U.S. Cl. ....................... 514/331; 514/307; 514/311; 514/326; 546/22; 546/139; 546/176; 546/197; 546/207; 546/209; 546/210; 546/211; 546/229

(58) Field of Search ................................. 514/307, 311, 514/326, 331; 546/22, 139, 176, 209, 210, 211, 197, 207, 229

(56) References Cited

FOREIGN PATENT DOCUMENTS

| EP | 0287339 | 4/1987 |
|---|---|---|
| EP | 0506468 | 3/1991 |
| EP | 0506478 | 3/1991 |
| GB | 1525584 | 3/1978 |
| WO | WO 96/31508 | * 10/1996 |
| WO | WO 98/27081 | * 6/1998 |
| WO | WO 98/47885 | * 10/1998 |

* cited by examiner

*Primary Examiner*—Ceila Chang
(74) *Attorney, Agent, or Firm*—Peter C. Richardson; Paul H. Ginsburg; Jolene W. Appleman

(57) ABSTRACT

Novel compounds having general formula (I), and pharmaceutically and veterinarily acceptable salts thereof wherein $R^1$, $R^2$, $R^3$, W, $Y^1$, $Y^2$, X, n and y are as defined above and processes for their preparation and intermediate compounds prepared therein. The novel compounds are useful for having utility in the treatment of pruritic dermatoses including allergic dermatitis and atopy in animals and humans.

41 Claims, No Drawings

4-PHENYLPIPERIDINES FOR THE TREATMENT OF PRURITIC DERMATOSES

CROSS REFERENCE TO RELATED APPLICATIONS

This application is the National Stage of International Application No. PCT/IB99/00886, filed May 17, 1999.

FIELD OF THE INVENTION

This invention relates to novel 4-phenylpiperidines having utility in the treatment of pruritic dermatoses including allergic dermatitis and atopy in animals and humans, and processes for the preparation of and intermediates used in the preparation of such compounds.

BACKGROUND OF THE INVENTION

Itching or pruritus is a common dermatological symptom which can give rise to considerable distress, in both humans and animals. Pruritus is often associated with inflammatory skin disease which can commonly be caused by hypersensitivity reactions, such as reaction to insect bites e.g. flea bites, or to environmental allergens such as house dust mite or pollen; or by bacterial and fungal infections of the skin or ectoparasite infections. Previous treatments for pruritus include the use of corticosteroids and antihistamines, however both have undesired side effects. Other therapies include the use of essential fatty acid dietary supplements which are slow to act and offer only limited efficacy against allergic dermatitis. A variety of emollients such as soft paraffin, glycerine and lanolin are also employed but with limited success and there is a continuing need for an effective remedy.

Certain 1,3,4-trisubstituted 4-aryl-piperidine derivatives are disclosed in GB-A-1525584 as potent narcotic antagonists which also display analgesic properties. These compounds are also claimed in EP-B-0287339 as opioid antagonists which block the effect of agonists at the mu or kappa receptors having potential utility in treating a variety of disorders associated with these receptors such as eating disorders, opiate overdose, depression, smoking, alcoholism, sexual dysfunction, shock, stroke, spinal damage and head trauma; utility as an appetite suppressant for weight loss has also been suggested. Further related 1-N-substituted-4-aryl piperidines are disclosed in EP-A-0506468 and EP-A-0506478. Potential utility is suggested in preventing peripherally mediated undesired opiate effects and in relieving the symptoms of idiopathic constipation and irritable bowel syndrome.

SUMMARY OF THE INVENTION

According to the present invention we provide novel 4-phenylpiperidines which are potent and effective antipruritic agents.

Thus the present invention provides compounds having the formula:

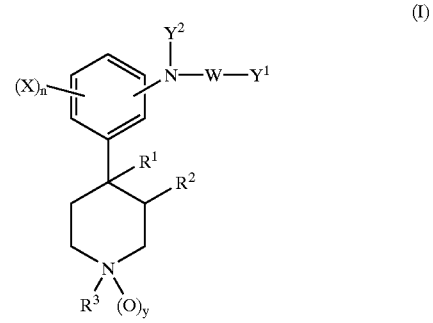

(I)

and pharmaceutically and veterinarily acceptable salts thereof wherein:

$R^1$ and $R^2$ are each independently H or $C_1$–$C_4$ alkyl; $R^3$ is $C_1$–$C_{10}$ alkyl, $C_3$–$C_{10}$ alkenyl, or $C_3$–$C_{10}$ alkynyl; wherein said alkyl, alkenyl or alkynyl group may optionally be substituted by one or more substituents independently chosen from:

OH; CN; one or more halo atoms; $C_1$–$C_6$ alkoxy; $C_1$–$C_6$ alkoxycarbonyl; $C_2$–$C_6$ alkanoyl; $C_2$–$C_6$ alkanoyloxy; $C_3$–$C_8$ cycloalkyl; $C_3$–$C_8$ cycloalkoxy; $C_4$–$C_9$ cycloalkanoyl; aryl; aryloxy; aryl($C_1$–$C_4$) alkoxy; heteroaryl; a saturated heterocyclic group; adamantyl or $ZBNR^4R^5$ wherein Z is a direct bond, CO or $S(O)_p$ wherein p=0, 1, 2 and wherein $B=(CH_2)_m$ wherein m=from 0 to 10 and wherein $R^4$ and $R^5$ are independently selected from H, $C_1$–$C_{10}$ alkyl, $C_3$–$C_{10}$ alkenyl, $C_3$–$C_{10}$ alkynyl, $C_3$–$C_8$ cycloalkyl, aryl or heteroaryl or wherein $R^4$ and $R^5$ represent unbranched $C_2$–$C_6$ alkylene groups which when taken together with the N to which they are bonded form a 4 to 7 membered saturated heterocyclic ring optionally containing O, S or N—$R^6$ wherein said heterocyclic ring may be substituted by one or more $C_1$–$C_4$ alkyl groups and wherein $R^6$ is H, $C_1$–$C_6$ alkyl, $C_3$–$C_8$ cycloalkyl, —($C_1$–$C_6$ alkylene)($C_3$–$C_8$ cycloalkyl) or —($C_1$–$C_6$ alkylene) aryl and wherein when Z is a direct bond and m=0, then $R^3$ is not a terminal alkenyl or alkynyl;

W is $SO_2$, C=O, P($Y^1$)=O or P($Y^1$)=S;

X is one or more substitutents independently selected from H, halo, $C_1$–$C_4$ alkyl, $C_1$–$C_4$ alkoxy, halo ($C_1$–$C_4$) alkyl or halo($C_1$–$C_4$)alkoxy;

$Y^1$ is $C_1$–$C_{10}$ alkyl which may optionally be substituted by one or more halo atoms or by OH, $C_1$–$C_4$ alkoxy, $C_2$–$C_6$ alkanoyloxy, $CONH_2$, $NH_2$ or aryl; $NH_2$, mono or di-($C_1$–$C_4$) alkylamino, $C_3$–$C_8$ cycloalkyl, aryl, phthalimidyl or heteroaryl;

$Y^2$ is H, $C_1$–$C_4$ alkyl, or $C_3$–$C_6$ alkenyl, wherein said alkyl or alkenyl groups may optionally be substituted by aryl, aryloxy or heteroaryl;

n is 0, 1 or 2; and y is 0 or 1.

In the definitions above, alkyl, alkenyl and alkynyl groups may be straight or branched-chain and halo means fluoro, chloro, bromo or iodo. The terms haloalkyl and haloalkoxy mean substituted by one or more halo atoms. Aryl and aryloxy means a phenyl, naphthyl, phenoxy or naphthyloxy group respectively which may optionally be substituted with from one to three substituents, each independently selected from OH, $C_1$–$C_4$ alkyl, $C_1$–$C_4$ alkoxy, $C_1$–$C_4$ haloalkyl, $C_1$–$C_4$ haloalkoxy, $C_2$–$C_5$ alkanoyl, halo, CN, $CH_2CN$, and $CONH_2$.

By heteroaryl is meant a 5 or 6 membered aromatic heterocyclic group containing as heteroatom one or more oxygen, sulphur or nitrogen atoms, and which may optionally be fused to a benzene ring and which may optionally be substituted in the heteroaryl or fused benzene ring with one or more substituents independently chosen from $C_1$–$C_4$ alkyl, $C_1$–$C_4$ alkoxy, $C_1$–$C_4$ haloalkyl, $C_1$–$C_4$ haloalkoxy, OH, =O, halo, aryl wherein aryl is preferably phenyl and CN. Particular examples of heteroaryl groups include pyrrolyl, imidazolyl, isoxazolyl, tetrazolyl, pyridyl, indolyl, benzofuranyl and quinolinyl, each optionally substituted as defined above.

By saturated heterocyclic groups is meant a 3 to 8 membered saturated heterocyclic group which contains as heteroatoms one or more oxygen, sulphur or nitrogen atoms, wherein the nitrogen atoms may optionally be substituted by $C_1$–$C_4$ alkyl and wherein the ring may optionally be benzofused. Particular examples include tetrahydropyranyl, 1,4-dioxanyl, piperidinyl, N-methyl-piperidinyl, piperazinyl, morpholinyl and 2,3-dihydro-1-benzofuranyl.

The piperidines of this invention form pharmaceutically or veterinarily acceptable acid addition salts with a wide variety of inorganic and organic acids. The particular acid used in salt formation is not critical; however, the corresponding salt that is formed must be substantially non-toxic to animals. Typical acids generally used include sulfuric, hydrochloric, hydrobromic, phosphoric, hydroiodic, sulfamic, citric, acetic, maleic, malic, succinic, tartaric, cinamic, benzoic, ascorbic and related acids. The piperidines additionally form quaternary ammonium salts, for example, with a variety of organic esters of sulfuric, hydrohalic and aromatic sulfonic acids, such as, for example camphorsulfonic acid.

The compounds of the invention contain one or more asymmetric centres and thus they can exist as enantiomers and diasteromers. The invention includes the use of both the separated individual isomers as well as mixtures of isomers.

Preferred herein are compounds wherein $N(Y^2)(WY^1)$ is in the meta position, y is zero, $W=SO_2$, $R^1$ and $R^2$ are $C_1$–$C_4$ alkyl groups with trans relative stereochemistry, preferably methyl groups, as detailed in the relative configuration illustrated by the general formula (Ia):

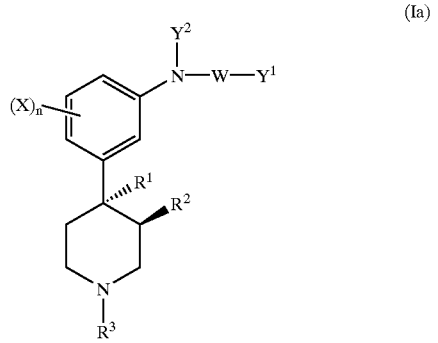

(Ia)

or compounds wherein $N(Y^2)(WY^1)$ is in the meta position, $W=SO_2$, $R^1$ is propyl and $R^2$ is hydrogen; $Y^2$ is hydrogen and wherein:

$Y^1$ is $C_1$–$C_{10}$ alkyl, preferably $C_1$–$C_6$ alkyl, more preferably $C_1$–$C_4$ alkyl, most preferably methyl, ethyl, propyl, isopropyl or butyl; imidazolyl or pyridyl; mono- or di-$C_1$–$C_3$ alkylamino, more preferably dimethylamino or monoisopropylamino; phenyl; or $C_1$–$C_{10}$ alkyl, preferably $C_1$–$C_6$ alkyl, more preferably $C_1$–$C_2$ alkyl substituted by $C_1$–$C_2$ alkoxy, or phenyl and wherein, $R^3$ is selected from: $C_4$–$C_{10}$ straight or branched chain alkyl, preferably $C_5$–$C_7$ alkyl, more preferably hexyl, preferably straight chain alkyl; or;

$C_1$–$C_{10}$ alkyl, preferably $C_1$–$C_4$ alkyl, more preferably $C_2$–$C_3$ alkyl substituted by: $C_5$–$C_6$ cycloalkyl, preferably cyclohexyl, optionally substituted by one or more $C_1$–$C_4$ alkyl groups, preferably methyl or dimethyl; $C_3$–$C_4$ alkoxy, preferably butoxy; $C_5$–$C_6$ cycloalkyloxy, preferably cyclohexyloxy; aryloxy, preferably phenoxy, optionally mono-substituted at the ortho position by chlorine, or, at the ortho or para positions for fluorine, bromine, iodine, or at the o-position for $C_1$–$C_2$ alkyl, preferably methyl; aryl $(C_1$–$C_2)$alkoxy, preferably benzyloxy; $C_5$–$C_6$ cycloalkanoyl, preferably cyclohexanoyl; saturated 5- or 6-membered heterocyclic ring wherein the heteroatom(s) are at the 2- or 4-positions, preferably a 2-tetrahydropyranyl; or heteroaryl selected from isoxazolyl or indolyl; or;

$C_1$–$C_{10}$ alkyl, preferably $C_1$–$C_3$ alkyl substituted by: aryl, preferably phenyl optionally substituted by $C_1$–$C_4$ alkyl, preferably ortho or meta methyl or ortho or para ethyl or ortho or para mono- or di-halo, preferably chloro of fluoro, or $CH_2CN$; $ZNR^4R^5$ wherein Z is carbonyl or a direct link, $R^4$ is hydrogen and $R^5$ is $C_5$–$C_6$ cycloalkyl, preferably, cyclohexyl; or $C_2$–$C_{10}$ alkyl, preferably $C_2$–$C_3$ alkyl substituted by hydroxy and $C_5$–$C_6$ cycloalkyl, preferably 3-cyclohexyl-3-hydroxypropyl; or $C_3$–$C_{10}$alkenyl, preferably, $C_3$–$C_6$ alkenyl, more preferably hex-5-enyl; or $C_3$–$C_4$ alkenyl substituted by: $C_5$–$C_6$ cycloalkyl, preferably cyclohexyl; aryl, preferably phenyl; or $C_3$–$C_{10}$ alkynyl, preferably $C_3$–$C_6$ alkynyl, more preferably hex-2-ynyl.

Preferred $Y^1$ groups for use herein include: methane, ethane, propane, 1-methylethane, butane, 3-pyridine, 1-methyl-1H-imidazol-4-yl, N-isopropylamino, 2-methoxyethane, N,N-dimethylamino, benzene and α-toluene.

More preferred $Y^1$ groups for use herein are: methane, ethane, propane, 1-methylethane, butane, 3-pyridine, 1-methyl-1H-imidazol-4-yl, N-isopropylamino and 2-methoxyethane.

Preferred $R^3$ groups for use herein include: N-(N-cyclohexylamino carbonylmethyl), N-(3-(4,4-dimethylcyclohexyl)propyl), N-(2-butoxyethyl), N-(3-phenoxypropyl), N-(3-(4-fluorophenoxy)propyl), N-(2-(2-chlorophenoxy)ethyl), N-(2-cyclohexyloxyethyl), N-(2-(4-fluorophenoxy)ethyl), N-(2-(2-chlorophenyl)ethyl), N-(1-(4-cyanomethylphenyl)methyl), N-(2-phenylethyl), N-(2-(5-[2,3-dihydro-1-benzofuranyl])ethyl), N-(3-(2,6-dimethylphenoxy)propyl), N-(2-(3-indolyl)ethyl), N-(hex-5-enyl), N-(hex-2-ynyl), N-(2-(2-methylphenoxy)ethyl), N-(2-benzyloxyethyl), N-(2-cyclohexylideneethyl), N-hexyl, N-(5-methylhexyl), N-(3-cyclohexylpropyl), N-benzyl, N-(3-phenylpropyl), N-(3-cyclohexyl-3-oxopropyl), N-(2-(3-methylphenyl)ethyl), N-(1-(4- ethylphenyl)methyl), N-(2-(2-methylphenyl)ethyl), N-(3-(2-methylphenyl)propyl), N-(3-(tetrahydropyran-2-yl)propyl), N-((S)-3-cyclohexyl-3-hydroxypropyl), N-((E)-3-cyclohexylprop-2-enyl) and N-cinnamyl.

More preferred $R^3$ groups for use herein are: N-(2-(2-methylphenoxy)ethyl), N-(2-benzyloxyethyl), N-(2-cyclohexylideneethyl), N-hexyl, N-(5-methylhexyl), N-(3-cyclohexylpropyl), N-benzyl, N-(3-phenylpropyl), N-(3-cyclohexyl-3-oxopropyl), N-(2-(3-methylphenyl)ethyl), N-(1-(4-ethylphenyl)methyl), N-(2-(2-methylphenyl)ethyl), N-(3-(2-methylphenyl)propyl), N-(3-(tetrahydropyran-2-yl)propyl), N-((S)-3-cyclohexyl-3-hydroxypropyl), N-((E)-3-cyclohexylprop-2-enyl) and N-cinnamyl.

Highly preferred herein are compounds wherein $N(Y^2)(WY^1)$ is in the meta position, y is zero, n is zero, $W=SO_2$, $R^1$ and $R^2$ are methyl groups with trans relative stereochemistry; $Y^2$ is hydrogen and wherein $Y^1$ is methane, ethane, propane, 1-methylethane, butane, 3-pyridine, 1-methyl-1H-imidazol-4-yl or N-isopropylamino and wherein $R^3$ is selected from: hexyl; methyl-hexyl; preferably 5-methyhexyl; or ethyl or propyl substituted by: cyclohexyl; cyclohexanoyl; 2-tetrahydropyranyl or methyl, ethyl or propyl, substituted by: phenyl, optionally substituted by methyl or ethyl; or 3-cyclohexyl-3-hydroxypropyl; or prop-2-enyl substituted by cyclohexyl or phenyl.

Highly preferred $Y^1$ groups for use herein are: methane, ethane, propane, 1-methylethane, butane, 3-pyridine, 1-methyl-1H-imidazol-4-yl and N-isopropylamino.

Highly preferred $R^3$ groups for use herein are: N-hexyl, N-(5-methylhexyl), N-(3-cyclohexylpropyl), N-benzyl, N-(3-phenylpropyl), N-(3-cyclohexyl-3-oxopropyl), N-(2-(3-methylphenyl)ethyl), N-(1-(4-ethylphenyl)methyl), N-(2-(2-methylphenyl)ethyl), N-(3-(2-methylphenyl)propyl), N-(3-(tetrahydropyran-2-yl)propyl), N-((S)-3-cyclohexyl-3-hydroxypropyl), N-((E)-3-cyclohexylprop-2-enyl) and N-cinnamyl.

Highly preferred compounds according to the present invention include:
(±)-4-(3-ethanesulfonylaminophenyl)-N-hexyl-trans-3,4-dimethylpiperidine,
(±)-4-(3-ethanesulfonylaminophenyl)-N-hexyl-trans-3,4-dimethylpiperidine,
(±)-4-(3-ethanesulfonylaminophenyl)-trans-3,4-dimethyl-N-(5-methylhexyl)piperidine,
(±)-trans-3,4-dimethyl-N-(5-methylhexyl)-4-(3-propanesulfonylaminophenyl)piperidine,
(±)-N-hexyl-trans-3,4-dimethyl-4-(3-propanesulfonylaminophenyl)piperidine,
(±)-N-(3-cyclohexylpropyl)-trans-3,4-dimethyl-4-(3-propanesulfonylaminophenyl)piperidine,
(±)-N-benzyl-trans-3,4-dimethyl-4-(3-propanesulfonylaminophenyl)piperidine,
(±)-trans-3,4-dimethyl-N-(3-phenylpropyl)-4-(3-propanesulfonylaminophenyl)piperidine,
(±)-N-hexyl-trans-3,4-dimethyl-4-(3-(2-methylethane)sulfonylaminophenyl)piperidine,
(±)-4-(3-n-butanesulfonylaminophenyl)-N-hexyl-trans-3,4-dimethylpiperidine,
(±)-N-hexyl-trans-3,4-dimethyl-4-(3-(3-pyridinesulfonylamino) phenyl)piperidine,
(±)-trans-3,4-dimethyl-N-(5-methylhexyl)-4-(3-(1-methyl-1H-imidazole-4-sulfonylamino)phenyl)piperidine,
(±)-N-hexyl-trans-3,4-dimethyl-4-(3-(1-methyl-1H-imidazole-4-sulfonylamino)phenyl)piperidine,
(±)-N-(3-cyclohexylpropyl)-trans-3,4-dimethyl-4-(3-(1-methyl-1H-imidazole-4-sulfonylamino)phenyl)piperidine,
(±)-trans-3,4-dimethyl-4-(3-(1-methyl-1H-imidazole-4-sulfonylamino) phenyl)-N-(3-phenylpropyl)piperidine,
(±)-N-hexyl-trans-3,4-dimethyl-4-(3-N-isopropylsulfamoylaminophenyl)piperidine,
(±)-4-(3-methanesulfonylaminophenyl)-trans-3,4-dimethyl-N-(5-methylhexyl)piperidine,
(+)-N-hexyl-4-(3-methanesulfonylaminophenyl)-trans-3,4-dimethylpiperidine,
(±)-N-(3-cyclohexyl-3-oxopropyl)-4-(3-methanesulfonylaminophenyl)-trans-3,4-dimethylpiperidine,
(±)-N-(3-cyclohexylpropyl)-4-(3-methanesulfonylaminophenyl)-trans-3,4-dimethylpiperidine,
(±)-4-(3-methanesulfonylaminophenyl)-trans-3,4-dimethyl-N-(2-(3-methylphenyl)ethyl)piperidine,
(±)-4-(3-methanesulfonylaminophenyl)-trans-3,4-dimethyl-N-(3-phenylpropyl)piperidine,
(±)-4-(3-methanesulfonylaminophenyl)-trans-3,4-dimethyl-N-(1-(4-ethylphenyl)methyl)piperidine,
(±)-4-(3-methanesulfonylaminophenyl)-trans-3,4-dimethyl-N-(2-(2-methylphenyl)ethyl)piperidine,
(±)-4-(3-methanesulfonylaminophenyl)-trans-3,4-dimethyl-N-(3-(2-methylphenyl)propyl)piperidine,
(±)-4-(3-methanesulfonylaminophenyl)-trans-3,4-dimethyl-N-(3-(tetrahydropyran-2-yl)-propyl)piperidine,
(±)-N-((S)-3-cyclohexyl-3-hydroxypropyl)-4-(3-methanesulfonylaminophenyl)-trans-3,4-dimethylpiperidine,
(±)-N-((E)-3-cyclohexylprop-2-enyl)-4-(3-methanesulfonylaminophenyl)-trans-3,4-dimethylpiperidine and
(±)-N-cinnamyl-4-(3-methanesulfonylaminophenyl)-trans-3,4-dimethylpiperidine.

Especially preferred herein are compounds wherein $N(Y^2)(WY^1)$ is in the meta position, y is zero, n is zero, $W=SO_2$, $R^1$ and $R^2$ are methyl groups with trans relative stereochemistry; $Y^2$ is hydrogen and wherein $Y^1$ is methane, ethane, propane and wherein $R^3$ is selected from: hexyl or 5-methylhexyl; or methyl or ethyl substituted by phenyl, substituted methyl or ethyl; or propyl substituted by phenyl, optionally substituted by methyl.

Especially preferred $Y^1$ groups for use herein are: methane, ethane and propane.

Especially preferred $R^3$ groups for use herein are: N-hexyl, N-(5-methylhexyl), N-benzyl, N-(3-phenylpropyl), N-(2-(3-methylphenyl)ethyl), N-(2-(2-methylphenyl)ethyl) and N-(3-(2-methylphenyl)propyl).

Especially preferred compounds herein are:
(±)-4-(3-ethanesulfonylaminophenyl)-N-hexyl-trans-3,4-dimethylpiperidine,
(+)-4-(3-ethanesulfonylaminophenyl)-N-hexyl-trans-3,4-dimethylpiperidine,
(±)-4-(3-ethanesulfonylaminophenyl)-trans-3,4-dimethyl-N-(5-methylhexyl)piperidine,
(±)-trans-3,4-dimethyl-N-(5-methylhexyl)-4-(3-propanesulfonylaminophenyl)piperidine,
(±)-N-hexyl-trans-3,4-dimethyl-4-(3-propanesulfonylaminophenyl)piperidine,
(±)-N-benzyl-trans-3,4-dimethyl-4-(3-propanesulfonylaminophenyl)piperidine,
(±)-trans-3,4-dimethyl-N-(3-phenylpropyl)-4-(3-propanesulfonylaminophenyl)piperidine,
(±)-4-(3-methanesulfonylaminophenyl)-trans-3,4-dimethyl-N-(5-methylhexyl)piperidine,
(+)-N-hexyl-4-(3-methanesulfonylaminophenyl)-trans-3,4-dimethylpiperidine, (±)-4-(3-methanesulfonylaminophenyl)-trans-3,4-dimethyl-N-(2-(3-methylphenyl)ethyl)piperidine, (±)-4-(3-methanesulfonylaminophenyl)-trans-3,4-dimethyl-N-(3-phenylpropyl)piperidine, (±)-4-(3-methanesulfonylaminophenyl)-trans-3,4-dimethyl-N-(2-(2-methylphenyl)ethyl)piperidine and (±)-4-(3-methanesulfonylaminophenyl)-trans-3,4-dimethyl-N-(3-(2-methylphenyl)propyl)piperidine.

For any of the above compounds use of a single enantiomer is preferred herein. In general, the (+) enantiomer is preferred.

According to a further aspect of the present invention there are provided compounds having the formula:

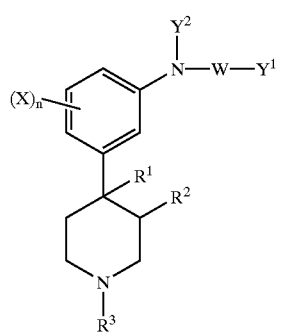

(Ib)

and pharmaceutically and veterinarily acceptable salts thereof wherein:

$R^1$ and $R^2$ are each independently H or $C_1$–$C_4$ alkyl;

$R^3$ is $C_1$–$C_{10}$ alkyl, $C_2$–$C_{10}$ alkenyl, or $C_2$–$C_{10}$ alkynyl; wherein said alkyl, alkenyl or alkynyl group may optionally be substituted by one or more substituents independently chosen from OH, ON, one or more halo atoms, amino, mono or di-($C_1$–$C_6$ alkyl)amino, $C_1$–$C_6$ alkoxy, $C_2$–$C_6$ alkanoyl, $C_2$–$C_6$ alkanoyloxy, $C_3$–$C_8$ cycloalkyl, $C_3$–$C_8$ cycloalkoxy, $C_4$–$C_9$ cycloalkanoyl, aryl, aryloxy, aryl ($C_1$–$C_4$) alkoxy, heteroaryl, a saturated heterocyclic group, or adamantyl;

W is $SO_2$, C=O, $P(Y^1)$=O or $P(Y^1)$=S;

X is H, halo, $C_1$–$C_4$ alkyl, $C_1$–$C_4$ alkoxy, or halo ($C_1$–$C_4$) alkyl;

$Y^1$ is $C_1$–$C_6$ alkyl which may optionally be substituted by one or more halo atoms or by OH, $C_1$–$C_4$ alkoxy, $C_2$–$C_6$ alkanoyloxy, $CONH_2$, $NH_2$ or aryl; $NH_2$, mono or di-($C_1$–$C_4$) alkylamino, $C_3$–$C_8$ cycloalkyl, aryl or heteroaryl;

$Y^2$ is H, $C_1$–$C_4$ alkyl, or $C_2$–$C_6$ alkenyl, wherein said alkyl or alkenyl groups may optionally be substituted by aryl or heteroaryl;

and n is 0, 1 or 2.

DETAILED DESCRIPTION OF THE INVENTION

The compounds of the invention may be prepared by a number of different processes. In one process the compounds of formula I may be prepared from an amine of the formula II:

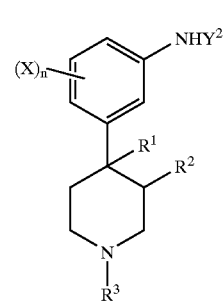

(II)

wherein $R^1$, $R^2$, $R^3$, $Y^2$ and n are as defined for formula (I), by reaction with a group of the formula Q—W—$Y^1$, wherein W and $Y^1$ are as defined for formula I and wherein Q is a suitable leaving group and is preferably a halogen atom, generally chloro, or with an anhydride of the formula $(Y^1W)_2O$.

Thus for the preparation of the sulfonamides of formula (I) wherein W is $SO_2$, the reaction is typically performed using a sulfonylchloride e.g. methanesulfonylchloride. The reaction is generally performed in a reaction inert organic solvent in the present of a base and is generally complete within a few hours at room temperature. The product is isolated and purified by conventional techniques.

Similarly, for the preparation of amides of formula (I) wherein W is CO, the reaction is either performed using the appropriate acylchloride or anhydride or when $Y^1$ is $C(R_7)(R_8)OH$ wherein $R_7$ and $R_8$ are independently selected from H, $C_1$–$C_4$ alkyl via rearrangement of a compound of general formula (VI) as described hereinafter, and wherein W is $P(Y^1)$=O or $P(Y^1)$=S, the appropriate phosphinic or thiophosphinic chloride, e.g. dimethylphosphinic chloride or dimethylphosphinothioic chloride. An alternative process proceeds via reaction of the N-unsubstituted piperidine (III):

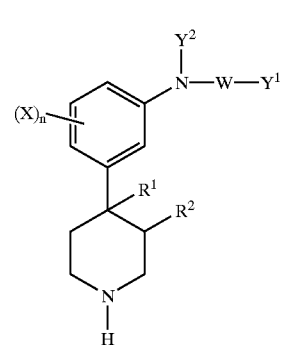

(III)

wherein $R^1$, $R^2$, $Y^1$, $Y^2$, W, X and n are as defined for the compound of formula (I) above, by reaction with a compound of formula $R^3$—X, wherein X is chloro, bromo, iodo or a leaving group such as an arylsulfonate (e.g. bromobenzenesulfonate), and $R^3$ is as previously defined for the compound of formula (I). The route is particularly useful when $R^3$ is a substituted alkyl, alkenyl or alkynyl group. Thus for example reaction with an arylsubstituted bromoalkane is achieved in a reaction inert organic solvent such as N,N-dimethylformamide in the presence of an acid acceptor such as sodium hydrogen carbonate by heating at between 80° C. and 120° C., preferably at about 100° C., for 3 or 4 hours. The product is isolated and purified by conventional techniques. The route may also be adapted using an acid chloride or using an acid of formula $R^9CO_2H$ with a coupling agent such as dicyclohexylcarbodiimide, to give the corresponding compound wherein the piperidine N-substituent is $COR^9$ (where $R^9$ is as defined for $R^3$ but lacking a $CH_2$ attachment group) and subsequent reduction yields the corresponding compound of formula (I).

The starting materials of formula (II) are prepared from the corresponding 3-hydroxyphenyl piperidine (IV) by conventional synthetic procedures. Thus for example the procedure shown in Scheme 1 may be used to prepare the compounds of formula II wherein $R^1$, $R^{2,}$ $R^3$ and $(X)_n$ are as defined for formula I above.

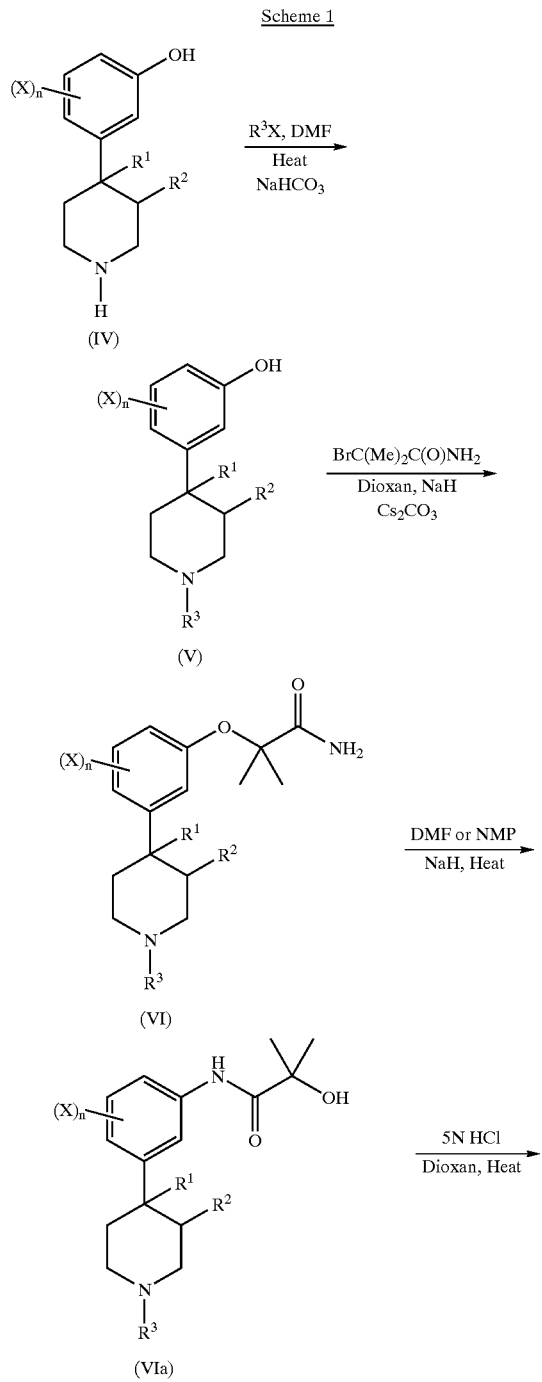

Scheme 1

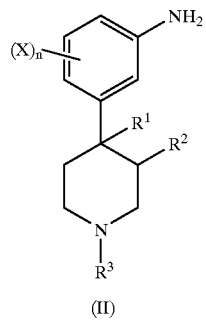

(II)

Thus for example, when $(X)_n$ is H, and $R^1$ and $R^2$ are both methyl, having the trans-configuration, the process starts with (±)-4-(3-hydroxyphenyl)-trans-3,4-dimethylpiperidine. Reaction with a compound of the formula $R^3X$, wherein X is chloro, bromo, iodo or a leaving group such as a bromobenzensulfonate group, for example hexylbromide gives the corresponding compound of formula (V). This is then reacted with caesium carbonate and sodium hydride, followed by 2-bromo-2-methylpropionamide to give the 3-(1-carbamoyl-1-methylethoxy) product (VI). Reaction of this product with sodium hydride in a reaction inert organic solvent such as N-methylpyrrolidine or N,N-dimethylformamide with heating, gives the 3-(2-hydroxy-2-methyl-propanoylamino)phenyl derivative (VIa), which is itself a compound of the invention. Subsequent hydrolysis, for example by heating with hydrochloric acid in dioxan gives the amine intermediate (II).

As an alternative process, the 3-hydroxyphenyl derivative (V) may be reacted with N-phenylbis(trifluoromethanesulfonimide) in dichloromethane in the presence of triethylamine to yield the corresponding 3-trifluoromethanesulfonyloxy derivative. This is reacted with benzophenone imine and 2,2'-bis(diphenylphosphino)-1,1'-binaphthyl in the presence of caesium carbonate and palladium(II)acetate by heating in tetrahydrofuran, to yield the 3-diphenylmethylidineamino derivative which is subsequently treated with dilute hydrochloric acid in tetrahydrofuran to yield the 3-aminophenyl intermediate (II).

The compounds of formula (IV) are either available by literature methods or are prepared by analogous procedures from readily available starting materials. Such as, for example, preparation of the 4-methyl or 4-n-propyl substituted phenols having the general formula (IV) from 1-bromo-3-(1-methylethoxy)benzene and N-ethyl-4-piperidone as described in Preparations 43, 44 and then, either Preparations 51, 52 and the intermediate compound from Preparation 53 to provide the 4-methyl analogue or, Preparations 65 to 67 to provide the 4-n-propyl analogue herein. Also, compounds of general formula (IV) wherein $(X)_n$ is hydrogen and $R^1$ and $R^3$ are hydrogen or $C_1$–$C_4$ alkyl such as methyl or propyl and $R^2$ is hydrogen can be made from 1-bromo-3-(1-methylethoxy)benzene and N-ethyl-4-piperidone as described in Preparations 43 to 47 herein. Compounds of general formula (V) wherein $(X)_n$ is hydrogen can be converted to compounds of general formula (V) wherein $(X)_n$ is $C_1$–$C_4$ alkyl such as methyl by, for example the process outlined in Preparations 71 to 73 herein. By a process analogous to that described for direct chlorination of compounds having the general formula (I), compounds of general formula (IV) wherein $(X)_n$ is hydrogen can be converted to compounds of general formula (IV) wherein $(X)_n$ is a halogen, such as chlorine by the process outlined in Examples 155 to 157.

The compounds of formula (III) are typically prepared from the corresponding compound of formula (I) wherein $R^3$ is benzyl. This is removed by conventional catalytic hydrogenation to yield the N-unsubstituted piperidine (III).

In some cases it is possible to introduce further substituents into the compound of formula (I) directly. Such additional substituents may be obtained by conversions of the $(X)_n$, $Y^1$, $Y^2$, $R^1$ or $R^2$ groups as described hereinafter.

Thus, for example, chlorination of a compound of the formula (I) wherein $(X)_n$ is H may be performed by reaction with a solution of chlorine in acetic acid to yield the corresponding compound where $(X)_n$ is a chlorine substituent. This process yields both the 4- and 6-substituted and the 4,6-disubstituted products.

Additional conversion of the terminal moiety of the $Y^1$ group on compounds having the general formula (I) wherein W is $SO_2$ and $Y_1$ is a $C_1$–$C_{10}$ alkyl, preferably a $C_1$–$C_3$ alkyl group substituted by a $C_1$–$C_4$ alkoxy group such as for example methoxy, or, a phthalimido group, or, a $C_2$–$C_6$ alkanoyloxy group such as ethoxycarbonylmethane to the corresponding alcohol, alkylamine or aminocarbonyl compounds can be achieved by the methods outlined in the respective Examples 20, 18 and 22.

Conversion of the $Y^2$ group on compounds having the general formula (I) wherein $Y^2$ is hydrogen, to compounds wherein $Y^2$ is an alkyl group may be achieved via direct alkylation as illustrated in Examples 69 and 78 herein.

Alternatively compounds having the general formula (I) wherein $Y^2$ is an alkyl group can be prepared from the amine compounds having the general formula (II) wherein $Y^2$ is hydrogen by direct alkylation of the amine to provide an alkylated amine followed by sulfonylation to provide a compound of general formula (I) as illustrated in Example 167 herein.

Similarly, compounds of formula (I) may be converted to the corresponding N-oxides via treatment with a suitable oxidising agent, such as aqueous hydrogen peroxide solution, as illustrated in Examples 168 and 169 herein.

As may be envisaged certain $R^3$ groups having the general formula $ZBNR^4R^5$ may be converted to form different groups of the general formula $ZBNR^4R^5$, such as for example reduction of an amide of an amide group to an amine group, as illustrated hereinafter in Example 51.

The above procedures may be adapted as appropriate to the particular reactants and groups involved and other variants will be evident to the skilled chemist by reference to standard textbooks and to the examples provided hereafter to enable all of the compounds of formula (I) to be prepared.

As an alternative process, the procedure shown in Scheme 2 may be used to prepare the compounds of formula (II):

Scheme 2

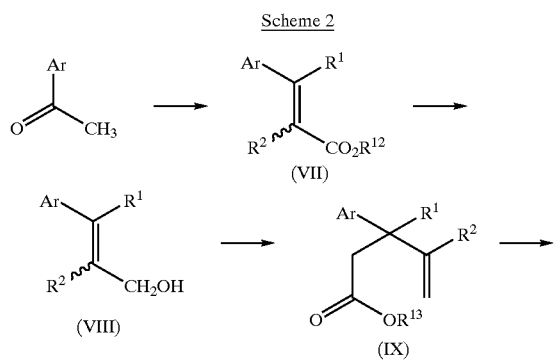

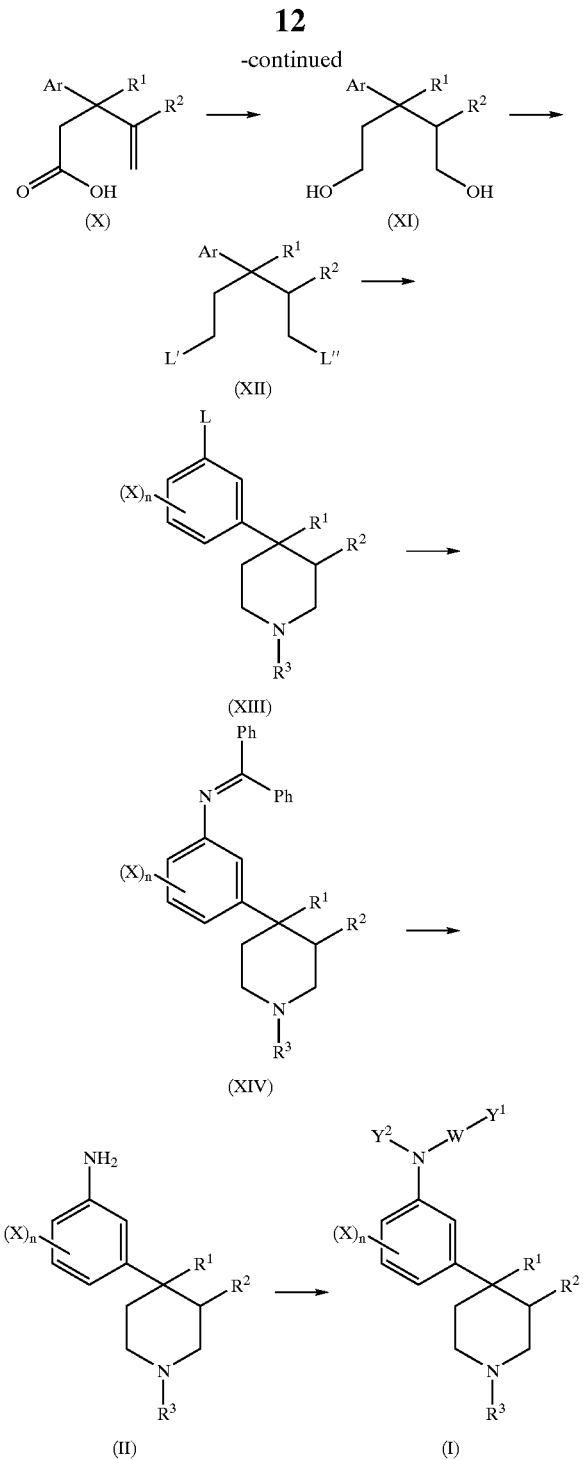

wherein $Y^1$, $Y^2$, W, $R^1$ and $R^2$ are as defined above and wherein each Ar is a phenyl group substituted by a further group L, wherein L is a bromo, iodo or —$NO_2$ or —$OR^{15}$ group, wherein $R^{15}$ is a $C_1$–$C_4$ alkyl group and wherein Ar is optionally substituted by one or more groups $(X)_n$ as defined above with the proviso that $(X)_n$ is not a bromo or iodo group; wherein $R^3$ is a straight or branched chain $C_1$–$C_{10}$ alkyl group, preferably a $C_1$–$C_6$ alkyl group, or a benzyl group and wherein said $C_1$–$C_{10}$ alkyl group may be substituted by one or more substituents selected from: aryl, preferably phenyl; or a $C_3$–$C_8$ cycloalkyl group, preferably $C_5$–$C_6$ cycloalkyl.

In scheme 2 the starting ketone is reacted with a phosphonate compound of the general formula: $(R^{10}O)_2P(O)CHR^2R^{11}$ wherein $R^{10}=C_1-C_4$ alkyl, preferably methyl or ethyl, $R^2$ is as defined previously herein and is preferably a methyl group, $R^{11}=CO_2R^{12}$ wherein $R^{12}$ is a $C_1-C_4$ alkyl group, preferably ethyl, and a strong alkali metal base such as butyl lithium, sodamide, sodium hydride, sodium alkoxide and preferably potassium t-butoxide, and, a relatively inert organic solvent such as a toluene/tetrahydrofuran (THF) mixture, ether, or preferably, toluene, to provide a mixture of cis- and trans-isomers of the α, β unsaturated ester compound of the general formula (VII).

The cis- and trans-isomers of compounds having the general formula (VII) can either be isolated, purified and/or separated at this stage or, as is preferred herein, isolated without purification and reduced with a suitable metal hydride reducing agent, preferably an aluminium hydride reducing agent, and especially diisobutylaluminium hydride in the presence of a suitable inert solvent such as toluene, THF, a THF/heptane mixture or preferably a THF/hexane mixture at low temperatures, in the range of from −78° C. to +70° C., preferably −78° C.-+20 C., to furnish a mixture of cis- and trans-isomers of alcohols having the general formula (VIII).

These isomers of compounds having the general formula (VIII) may be separated and purified at this stage. However, it is preferred herein to isolate the isomeric mixture and react this unpurified mixture of alcohols with a compound of the formula: $MeC(OR^{13})_3$ wherein $R^{13}$ is $C_1-C_4$ alkyl or aryl and is preferably methyl to give an intermediate ortho ester of general formula (VIIIa):

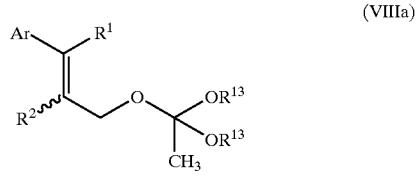

(VIIIa)

which can then either be heated in the absence of solvent or, preferably heated with a suitable high boiling hydrocarbon solvent, such as xylene or preferably petroleum ether (140–160) or nonane at elevated temperatures, preferably 140° C. to 160° C. to provide an ester compound having the general formula (IX).

Conversion of ester compounds having the general formula (IX) to compounds of the general formula (X) is accomplished via alkaline hydrolysis with a suitable base such as lithium hydroxide, potassium hydroxide or preferably sodium hydroxide in an aqueous alcoholic solvent such as aqueous methanol, ethanol or preferably aqueous isopropyl alcohol followed by an acidic work-up. The racemic mixture of (R)- and (S)-enantiomers of acids having the general formula (X) may either be resolved at this stage, as detailed herein after, or further reacted as a racemic mixture.

Hydroboration of the double bond and concomitant reduction of the acid group followed by oxidative work up of compounds having general formula (X) provides a mixture of diols having the general formula (XI). Suitable hydroborating and reducing agents include borane/tetrahydropyran, borane/diethyl ether, borane/dioxan, borane/toluene and preferably a diborane/tetrahydofuran complex generated in situ from sodium borohydride and boron trifluoride/tetrahydofuran complex. The oxidative work-up may be performed using sodium hydroxide in the presence of hydrogen peroxide, sodium perborate or, preferably, aqueous sodium percarbonate. Separation of the diastereomeric mixture of diols having general formula (XI) may be achieved by either recrystallisation techniques or flash column chromatography on silica gel with a suitable solvent, such as ethyl acetate in toluene. The ratio of solvents utilised will be dependant upon the particular diol mixture and the silica type and such determination is within the ordinary means of the skilled chemist.

The hydroxyl groups on compounds having the general formula (XI) are activated to afford suitable leaving groups (L' and L") to provide a compound having general formula (XII) via treatment with an alkyl, or aryl sulfonylhalide or anhydride of formula $R^{14}SO_2Hal$ wherein $R^{14}$ is phenyl, 4-methylphenyl, $C_1-C_4$ alkyl, preferably ethyl or methyl, and wherein Hal is chlorine, iodine, fluorine or bromine, preferably chlorine, in the presence of one or more equivalents of an amine base such as pyridine, trimethylamine, tripropyl amine or preferably triethylamine and a suitable solvent such as dichloromethane, tetrahydrfuran, dioxan, ethyl acetate or preferably toluene or wherein L' and L" are each independently selected from a halogen such as chlorine, bromine or iodine and wherein such dihalo derivatives are formed by reaction with a suitable halogenating agent such as thionyl chloride.

Cyclisation of compound (XII) to form a compound having the general formula (XIII) is achieved via treatment with a primary amine of the formula $R^3NH_2$ wherein $R^3$ is $C_1-C_{10}$ alkyl, wherein said $C_1-C_{10}$ alkyl may be substituted by one or more substitutents selected from: aryl, preferably phenyl; $C_3-C_8$ cycloalkyl, preferably cyclohexyl; and wherein $R^3NH_2$ is most preferably n-hexylamine. The reaction can be performed as a single phase reaction with an excess of $R^3NH_2$ in an inert organic solvent such as toluene, or, more preferably, as a 2-phase reaction system with base, which is preferably inorganic, and, optionally aqueous, such as sodium carbonate, and an inert organic solvent (other than $R^3NH_2$) such as toluene and wherein said base is preferably present at a molar equivalent level of at least 2:1 to the compound having the general formula (XII).

Conversion of compounds having the general formula (XIII) wherein L is bromo or iodo to compounds having the general formula (II) can be achieved via reaction with benzophenone imine and a suitable source of palladium such as palladium diacetate and a ligand, for the palladium, such as (R)-(+)-2,2'-bis(diphenyl phosphino)-1,1'-binaphthyl ((R)-(+)-BINAP)), or (S)-(−)-BINAP or a mixture of (R)-(+)- and (S)-(−)-BINAP in the presence of a base of formula MOR (wherein M is an alkali metal and R is a tertiary alkyl) such as sodium tertiary butoxide and a suitable solvent such as THF or toluene, or an alkali metal carbonate such as caesium carbonate in THF or dioxan as solvent. Such reaction furnishes an intermediate compound of general formula (XIV) which is treated with mineral acid, such as dilute hydrochloric acid, and optionally, heat, to provide an amine of general formula (II).

Conversion of compounds having the general formula (XIII) wherein L is —$NO_2$ to compounds of the general formula (II) can be achieved either via hydrogenation with a suitable catalyst such as 10% palladium on charcoal, or, using elemental iron or iron powder and calcium chloride in aqueous ethanol.

Conversion of compounds having the general formula (XIII) wherein L is —$OR^{15}$ wherein $R^{15}$ is a $C_1-C_4$ alkyl group, preferably isopropyl to compounds of the general formula (II) can be achieved via firstly conversion to the alcohol via acidic hydrolysis followed by conversion to the trifluromethylsulfonate of the general formula (XXV) as detailed hereinbefore, and subsequent treatment with benzophenone imine, a suitable source of palladium and a ligand, followed by acid hydrolysis of the imine of general formula (XIV) to furnish a compound of general formula (II) as detailed hereinbefore.

Conversion of compounds having the general formula (II) to the desired compounds of the general formula (I) may be achieved by any of the methods detailed herein.

A preferred process wherein $R^1$, $R^2$ and $R^{13}$ are methyl, L is bromo or iodo, $Y^1$ is methane, ethane or propane and $R^3$ is selected from: N-hexyl, N-(5-methylhexyl), N-benzyl, N-(3-phenylpropyl), N-(2-(3-methylphenyl)ethyl), N-(2-(2-methylphenyl)ethyl) or N-(3-(2-methylphenyl)propyl) and $R^{12}$ is ethyl and $(X)_n$ is hydrogen is illustrated in Scheme 3.

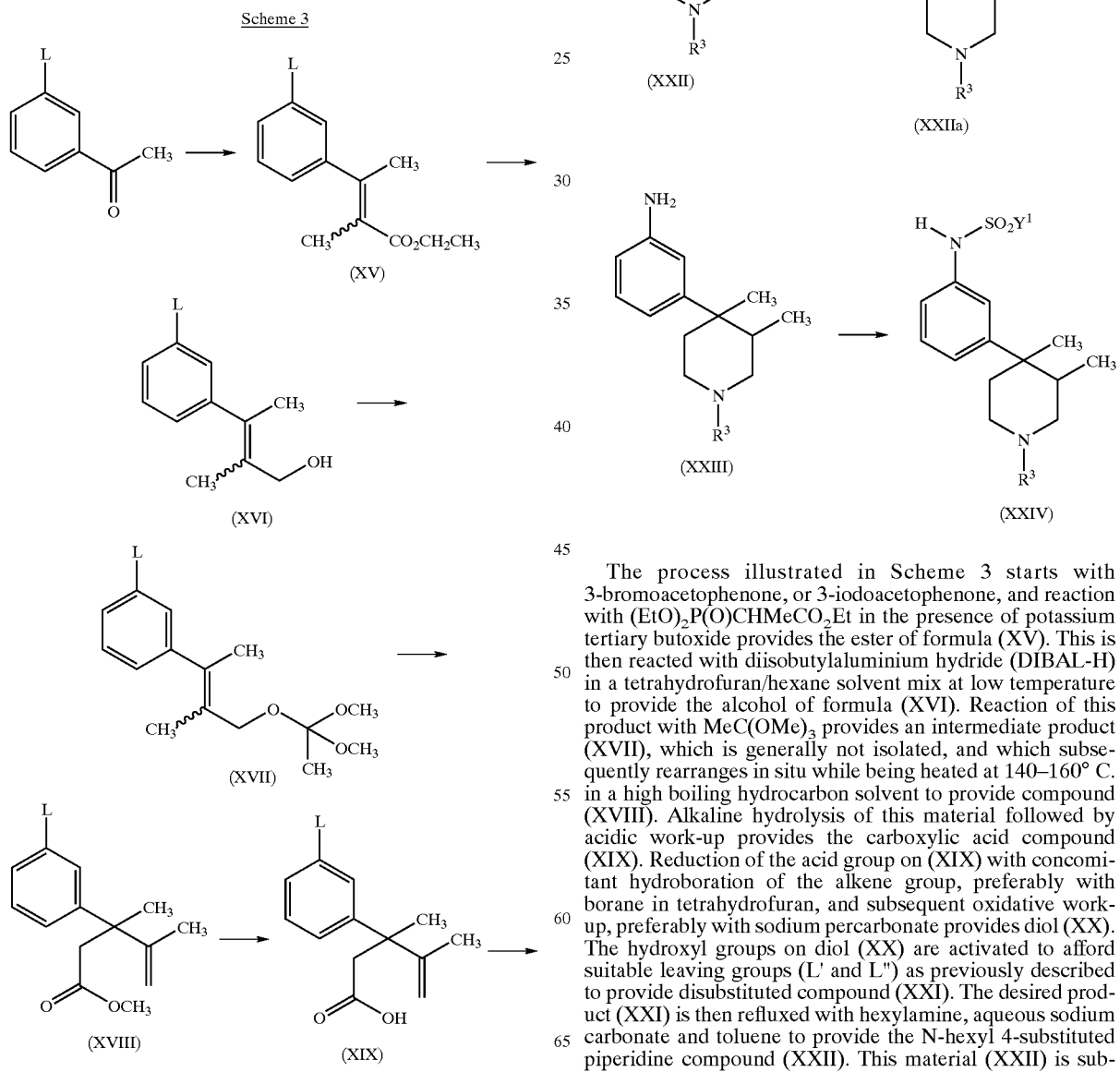

The process illustrated in Scheme 3 starts with 3-bromoacetophenone, or 3-iodoacetophenone, and reaction with $(EtO)_2P(O)CHMeCO_2Et$ in the presence of potassium tertiary butoxide provides the ester of formula (XV). This is then reacted with diisobutylaluminium hydride (DIBAL-H) in a tetrahydrofuran/hexane solvent mix at low temperature to provide the alcohol of formula (XVI). Reaction of this product with $MeC(OMe)_3$ provides an intermediate product (XVII), which is generally not isolated, and which subsequently rearranges in situ while being heated at 140–160° C. in a high boiling hydrocarbon solvent to provide compound (XVIII). Alkaline hydrolysis of this material followed by acidic work-up provides the carboxylic acid compound (XIX). Reduction of the acid group on (XIX) with concomitant hydroboration of the alkene group, preferably with borane in tetrahydrofuran, and subsequent oxidative work-up, preferably with sodium percarbonate provides diol (XX). The hydroxyl groups on diol (XX) are activated to afford suitable leaving groups (L' and L'') as previously described to provide disubstituted compound (XXI). The desired product (XXI) is then refluxed with hexylamine, aqueous sodium carbonate and toluene to provide the N-hexyl 4-substituted piperidine compound (XXII). This material (XXII) is subsequently converted to an amine via, firstly, treatment with benzophenone imine, sodium tertiary butoxide, BINAP and palladium diacetate to provide the intermediate imine (XXIIa) which is subsequently converted in situ to amine (XXIII) by acid hydrolysis with aqueous hydrochloric acid. The desired material (XXIV) may then be formed either as the free base via treatment of amine (XXIII) with methane sulfonylchloride, triethylamine in toluene or as a salt via subsequent treatment with a suitable acid such as (+) or (−) camphor sulfonic acid. This final conversion may be carried out either at room temperature over an extended period (up to several days) or in a shorter time at elevated temperatures.

As detailed earlier herein the compounds of the invention contain one or more chiral centres and thus can exist as enantiomers and diastereoisomers. Separation of individual isomers from mixtures of isomers can occur either at the end of the process or at relevant stages throughout the process as desired by the individual chemist. Such separation may be effected using standard techniques as are known in the art.

For example, in the reaction sequences illustrated in schemes 2, 3 and 4 separation of the mixture of cis and trans geometric isomers of the compounds having the general formulae (VII), (VIII), (XV) and (XVI) during the synthesis is not necessary. However, such separation can be effected using standard chromatographic techniques.

The mixture of enantiomers having the general formula (X) or (XIX) may be resolved using a chiral amine. Suitable chiral amines include: cinchonidine, cinchonine, (S)-(−)-(1-naphthyl)ethyl amine, (R)-(+)-(1-naphthyl)ethyl amine or preferably (S)-(+)-cyclohexylethyl amine. The compounds are resolved via formation of a diastereomeric mixture of amine salts which can be separated via recrystallisation in a suitable solvent such as butanone, isopropanol and preferably acetone. The thus separated amine salts may then be further purified by recrystallisation and/or treated with acid, such as hydrochloric acid, to furnish the separated (+) and (−) forms of the acid having the general formulae (X) and (XIX).

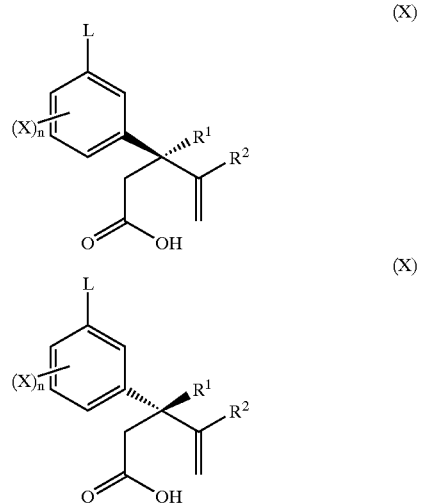

where the compound having the general formula (X) wherein $R^1$ and $R^2$ are methyl groups and L is bromine and n is zero, resolution with (S)-(+)-cyclohexylethyl amine provides the (+) compounds in a 95:5 ratio. Use of (R)-(−) cyclohexylethyl amine provides the (−) compounds in a 95:5 ratio In the reaction sequences illustrated in schemes 2, 3 and 4 separation of the mixture of cis- and trans-diastereoisomers of the compounds having the general formulae (I), (II), (XI), (XII), (XIII), (XX), (XXI), (XXII), (XXIII) and (XXIV) wherein the enantiomeric mixture has been previously separated as detailed hereinbefore, can be achieved by either standard chromatographic techniques or recrystallisation from a suitable solvent to provide the required cis or trans compounds with a diastereomeric purity of greater than 50:50, preferably 70:30 more preferably 80:20 and most preferably 95:5. For example a diastereoisomeric mixture of compounds of the formula (XXXI), prepared from the (+) enantiomer of the compound having the general formula (XI) wherein $R^1$ and $R^2$ are methyl groups and L is bromine and n is zero, were separated by chromatography on silica to provide the trans-dimethyl isomer as a single (+) enantiomer in greater than 95% diastereomeric purity.

If however, no separation is carried out during the process (as described in schemes 2 to 4) then chiral phase HPLC may be used to isolate the various final compounds i.e. compounds having the general formulae (I) or (XXIV).

Preferred for use herein are trans-dimethyl isomers.

In a further alternative process, based on the procedure shown in scheme 2, the starting aryl group may have the general formula (XXV):

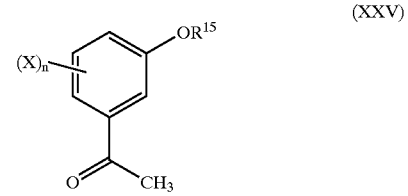

wherein $R^{15}=C_1-C_4$ alkyl, and $(X)_n$ is as defined previously herein.

This material may be converted to the corresponding ester of general formula (VII) and then to a piperidine of general formula (XIII), wherein L is $—OR^{15}$, as detailed in schemes 2 and 3. Conversion to the alcohol via acidic hydrolysis followed by conversion to the trifluromethylsulfonate (triflate) of the general formula (XXVI) as hereinbefore detailed.

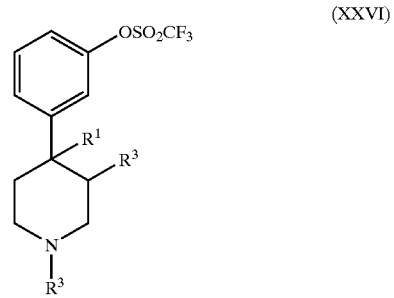

wherein $R^1$, $R^2$ and $R^3$ are as defined for the compounds of general formula (I).

Compounds having general formula (XXVI) may be converted to amines having formula (II) via the reaction with a source of palladium as detailed hereinbefore for compounds having general (XIII).

The processes illustrated herein according to the present invention for the preparation of compounds having the general formula (I) wherein the $N(Y^1)(WY^2)$ group is in the meta position can be applied by analogy to prepare compounds having the general formula (I) wherein the $N(Y^1)(WY^2)$ group is in the ortho or para positions.

It will be appreciated that where the processes according to the present invention for the preparation of compounds having the general formulae (I) and (XXIV) as defined herein give rise to intermediate compounds, these intermediate compounds provide additional embodiments of the invention.

Thus, according to a further aspect of the present invention there are provided intermediate compounds having the general formulae (II), (IIa), (III), (IIIa), (VI), (VIa), (VII), (VIII), (VIIIa), (IX), (X), (XI), (XII), (XIII), (XIV), (XV), (XVI), (XVII), (XVIII), (XIX), (XX), (XXI), (XXII), (XXIIa) and (XXIII) as illustrated in schemes 1, 2 and 3 and as described and defined hereinbefore.

It will be apparent to those skilled in the art that sensitive functional groups may need to be protected and deprotected during synthesis of a compound of the invention.

This may be achieved by conventional techniques, for example as described in 'Protective Groups in Organic Synthesis' by T W Greene and P G M Wuts, John Wiley and Sons Inc., 1991.

It will be appreciated by those skilled in the art that certain protected derivatives of compounds of formula (I), which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". Further, certain compounds of formula (I) may act as prodrugs of other compounds of formula (I).

It will further be appreciated by those skilled in the art, that certain moieties, known to those skilled in the art as "pro-moieties", for example as described in 'Design of Prodrugs' by H. Bundgaard, Elsevier, 1985, may be placed on appropriate functionalities when such functionalities are present within compounds of formula (I).

All protected derivatives, and prodrugs, of compounds of formulae (I), (II), (XXIII) and (XXIV) are included within the scope of the invention.

While it is possible to administer a compound of the invention directly without any formulation, the compounds are preferably employed in the form of a pharmaceutical or veterinary formulation comprising a pharmaceutically or veterinarily acceptable carrier, diluent or excipient and a compound of the invention. Such compositions will contain from 0.1 percent by weight to 90.0 percent by weight of the active ingredient.

The methods by which the compounds may be administered for veterinary use include oral administration by capsule, bolus, tablet or drench, topical administration as an ointment, a pour-on, spot-on, dip, spray, mousse, shampoo, collar or powder formulation or, alternatively, they can be administered by injection (e.g. subcutaneously, intramuscularly or intravenously), or as an implant.

Such formulations are prepared in a conventional manner in accordance with standard veterinary practice. Thus capsules, boluses or tablets may be prepared by mixing the active ingredient with a suitable finely divided diluent or carrier additionally containing a disintegrating agent and/or binder such as starch, lactose, talc or magnesium stearate, etc. Oral drenches are prepared by dissolving or suspending the active ingredient in a suitable medium. Pour-on or spot-on formulations may be prepared by dissolving the active ingredient in an acceptable liquid carrier vehicle such as butyl digol, liquid paraffin or a non-volatile ester, optionally with the addition of a volatile component such as propan-2-ol. Alternatively, pour-on, spot-on or spray formulations can be prepared by encapsulation, to leave a residue of active agent on the surface of the animal. Injectable formulations may be prepared in the form of a sterile solution which may contain other substances, for example enough salts or glucose to make the solution isotonic with blood. Acceptable liquid carriers include vegetable oils such as sesame oil, glycerides such as triacetin, esters such as benzyl benzoate, isopropyl myristate and fatty acid derivatives of propylene glycol, as well as organic solvents such as pyrrolidin-2-one and glycerol formal. The formulations are prepared by dissolving or suspending the active ingredient in the liquid carrier such that the final formulation contains from 0.1 to 10% by weight of the active ingredient.

These formulations will vary with regard to the weight of active compound contained therein, depending on the species of animal to be treated, the severity and type of infection and the body weight of the animal. For parenteral, topical and oral administration, typical dose ranges of the active ingredient are 0.01 to 100 mg per kg of body weight of the animal. Preferably the range is 0.1 to 10 mg per kg.

The compositions are preferably formulated in a unit dosage form, each dosage containing from about 1 to about 500 mg, more usually about 5 to about 300 mg, of the active ingredient. The term "unit dosage form" refers to physically discreet units suitable as unitary dosages for human subjects and other mammals, each unit containing a predetermined quantity of active material calculated to produce the desired therapeutic effect, in association with a suitable pharmaceutical carrier.

For veterinary use, the compounds of the invention are of particular value for treating pruritus in domestic animals such as cats and dogs and in horses. Thus the invention also provides a veterinary formulation comprising a compound of the formula (I), as defined above, together with a veterinarily acceptable diluent or carrier. Such formulations include in particular tablets (including palatable tablets), ointments, pour-on formulations, spot-on formulations, dips, sprays, mousse, shampoo, collar and powder formulations. Further acceptable dosage forms include, for example, capsules, boluses or drenches.

As an alternative for treating animals, the compounds may be administered with the animal feedstuff and for this purpose a concentrated feed additive or premix may be prepared for mixing with the normal animal feed.

For human use the compounds are administered as a pharmaceutical formulation containing the active ingredient together with a pharmaceutically acceptable diluent or carrier. Such compositions include conventional tablets, capsule and ointment preparations which are formulated in accordance with standard pharmaceutical practice.

Compounds of the invention may be administered either alone or in combination with one or more agents used in the treatment or prophylaxis of disease or in the reduction or suppression of symptoms. Examples of such agents (which are provided by way of illustration and should not be construed as limiting) include antiparastics e.g. fipronil, lufenuron, imidacloprid, avermectins (e.g. abamectin, ivermectin, doramectin), milbemycins, organophosphates, pyrethroids; antihistamines e.g. chlorpheniramine, trimeprazine, diphenhydramine, doxylamine; antifungals e.g. fluconazole, ketoconazole, itraconazole, griseofulvin, amphotericin B; antibacterials e.g. enrofloxacin, marbofloxacin, ampicillin, amoxycillin; anti-inflammatories e.g. prednisolone, betamethasone, dexamethasone, carprofen, ketoprofen; dietary supplements e.g. gamma-linoleic acid; and emollients.

The invention also provides for a method of treating pruritus, in a human or animal which comprises administering a therapeutically or prophylactically effective amount of a compound of the formula 1, as defined above, or a pharmaceutically or veterinarily acceptable salt thereof.

The following examples are illustrative of the preparation of typical compounds of the invention.

Melting points were determined using a Gallenkamp melting point apparatus and are uncorrected.

Nuclear magnetic resonance (NMR) spectral data were obtained using a Varian Unity 300 or 400, or Bruker $AC_{300}$ or AM300 spectrometer, the observed chemical shifts ($\delta$) being consistent with the proposed structures.

Mass spectral (MS) data were obtained on a Finnigan Mat. TSQ 7000, Finnigan Navigator, Fisons Instruments Trio 1000 or Micromass Platform LC spectrometer. The calculated and observed ions quoted refer to the isotopic composition of lowest mass.

HPLC means high performance liquid chromatography.

Room temperature means 20 to 25° C.

The prepared compounds as detailed in the Examples and Preparations have been named as derivatives of 4-phenylpiperidine. IUPAC nomenclature and rules have been used to describe the substituents thereon.

Biological Activity

The compounds of the invention are evaluated for their activity as antipruritic agents by measuring their ability to inhibit the hind leg scratching behaviour induced in rats by the administration of a known pruritogenic agent. These studies are based on the procedure described by Berendsen and Broekkamp in the European Journal of Pharmacology, 1991, 194, 201. The test is performed as follows:

Male Wistar rats (approximately 150 g body weight) are challenged with a pruritogen by subcutaneous injection of 5-methoxytryptamine hydrochloride (4 mg/3 ml/kg) dissolved in physiological saline into the scruff of the neck. At this dose a constant and quantifiable hindleg scratching response lasting up to 90 minutes is obtained.

The test compound is administered to the test animals by subcutaneous injection in an aqueous micelle formulation. The test compound is prepared in the following manner. The compound is dissolved in a vehicle (composition v/v %: glycerol formal, 24; tween 80, 17; benzyl alcohol, 1.5 and purified water to 100) then seven parts purified water is added to three parts of the above vehicle to give the aqueous micelle formulation. The compounds can be administered pre- or post-challenge or may be administered at the same time as the pruritogenic challenge.

After the pruritogen challenge has been administered, hindleg scratching is scored for each animal by recording the presence or absence of scratching during each 30 second interval as 1 or 0 scored respectively. The score for each animal is totalled after 25 minutes (maximum score 50). The efficacy of compounds is assessed by their ability to significantly reduce the score in treated groups compared to the control group.

Compounds according to the present invention, for example the compound of Example 101, were found to display anti-pruritic activity when tested in accordance with the above procedure.

Antipruritic activity was also demonstrated in dogs suffering from flea induced pruritus. Administration by subcutaneous injection or gavage at dose levels of 1–10 mg/kg led to a rapid and sustained reduction in pruritic behaviour such as scratching, rubbing and licking.

EXAMPLES

Example 1

(±)-N-Hexyl-4-(3-(2-hydroxy-2-methylpropanoylamino)phenyl)-trans-3,4-dimethylpiperidine To a solution of (±)-4-(3-(1-carbamoyl-1-methylethoxy) phenyl)-N-hexyl-3,4-dimethylpiperidine (Preparation 2, 13.13 g, 35 mmol) in N-methylpyrrolidinone (175 ml) under an atmosphere of nitrogen was added sodium hydride (60% dispersion in mineral oil, 4 g, 100 mmol) in four portions over 30 min. The resultant mixture was stirred for 30 min and then heated at 170° C. overnight. The reaction mixture was cooled, carefully poured onto water (200 ml) and extracted with diethyl ether (3×150 ml). The combined extracts were washed with water (2×100 ml), dried ($Na_2SO_4$) and concentrated in vacuo to afford the title compound as an orange oil (12.9 g, 98%) which was used without further purification.

NMR ($CDCl_3$, selected data for the free base): 0.8 (d, 3H), 0.9 (m, 3H), 2.0 (m, 1H), 2.3 (m, 4H), 2.5 (m, 2H), 2.8 (m, 1H), 7.05–7.55 (m, 4H), 8.75 (br. s, 1H).

MS (thermospray): M/Z [$MH^+$] 375.4; $C_{23}H_{38}N_2O_2$+H requires 375.3.

Example 2

(±)-4-(3-Acetylaminophenyl)-N-hexyl-trans-3,4-dimethylpiperidine

To a solution of (±)-4-(3-aminophenyl)-N-hexyl-trans-3,4-dimethylpiperidine (Preparation 5, 57 mg, 0.2 mmol) in dichloromethane (1.6 ml) at 0° C. under an atmosphere of nitrogen was added triethylamine (0.4 ml) followed by acetyl chloride (16 ml, 0.22 mmol) dropwise, and the resultant mixture was stirred overnight. The reaction mixture was diluted with saturated aqueous sodium hydrogen carbonate solution (5 ml) and extracted with dichloromethane (3×10 ml). The combined extracts were dried ($Na_2SO_4$) and concentrated in vacuo to give the crude product which was purified by silica (6 g) column chromatography eluting with ethyl acetate: hexane:0.880 ammonia (50:50:1) to give the title compound as a pale brown oil (60 mg, 92%).

NMR ($CDCl_3$, selected data for the free base): 0.75 (d, 3H), 0.9 (m, 3H), 2.0 (m, 1H), 2.15 (s, 3H), 2.3 (m, 4H), 2.5 (m, 2H), 2.8 (m, 1H), 7.0–7.4 (m, 4H).

MS (thermospray): M/Z [$MH^{30}$] 331.6; $C_{21}H_{34}N_2O$+H requires 331.3.

Example 3

(±)-N-Hexyl-4-(3-methanecarbamoylaminophenyl)-trans-3,4-dimethylpiperidine

To a solution of (±)-4-(3-aminophenyl)-N-hexyl-trans-3,4-dimethylpiperidine (Preparation 5, 70 mg, 0.243 mmol) in dichloromethane (2 ml) at 0° C. under an atmosphere of nitrogen was added triethylamine (0.5 ml) followed by methyl chloroformate (21 ml, 0.267 mmol) dropwise, and the resultant mixture was stirred overnight. The reaction mixture was diluted with saturated aqueous sodium hydrogen carbonate solution (5 ml) and extracted with dichloromethane (3×10 ml). The combined extracts were dried ($Na_2SO_4$) and concentrated in vacuo to give the crude product which was purified by silica (6 g) column chromatography, eluting with ethyl acetate:hexane:0.880 ammonia (40:60:1) to give the title compound as a clear oil (35 mg, 42%).

NMR ($CDCl_3$, selected data for the free base): 0.75 (d, 3H), 0.9 (m, 3H), 1.3 (s, 3H), 1.95 (m, 1H), 2.3 (m, 4H), 2.5 (m, 2H), 2.75 (m, 1H), 7.0–7.4 (m, 4H).

MS (thermospray): M/Z [$MH^+$] 347.1; $C_{21}H_{34}N_2O_2$+H requires 347.3.

Example 4

(±)-N-Hexyl-4-(3-methanesulfonylaminophenyl)-trans-3,4-dimethylpiperidine

To a solution of (±)-4-(3-aminophenyl)-N-hexyl-trans-3,4-dimethylpiperidine (Preparation 5, 7.5 g, 26 mmol) in pyridine (75 ml) at 0° C. under an atmosphere of nitrogen was added methanesulfonyl chloride (2.7 ml, 35 mmol) dropwise, and the resultant mixture was stirred overnight. Ice (100 g) was added and, after 1 h, the reaction mixture was extracted with ethyl acetate (5×200 ml). The combined extracts were dried ($Na_2SO_4$) and concentrated in vacuo at 80° C. to give the crude product which was purified by silica (150 g) column chromatography eluting with ethyl acetate:hexane:0.880 ammonia (40:60:1) to give the title compound as a golden oil (7.81 g, 82%).

NMR ($CDCl_3$, selected data for the free base): 0.75 (d, 3H), 0.9 (m, 3H), 2.0 (m, 1H), 2.3 (m, 4H), 2.5 (m, 2H), 2.8 (m, 1H), 3.0 (s, 3H), 7.0–7.4 (m, 4H).

MS (thermospray): M/Z [$MH^+$] 367.3; $C_{20}H_{34}N_2O_2S+H$ requires 367.2.

Example 5

Resolution of the enantiomers of (±)-N-hexyl-4-(3-methanesulfonylaminophenyl)-trans-3,4-dimethylpiperidine The enantiomers of (±)-N-hexyl-4-(3-methanesulfonylaminophenyl)-trans-3,4-dimethylpiperidine (Example 4) were separated by preparative HPLC on a Chiralpak™ AD column, 25 cm×2.0 cm; Flow 9.0 ml min$^{-1}$; employing U.V. detection at 220 nm; eluant hexane:propan-2-ol (95:5)+0.5% (v/v) diethylamine. Enantiomeric purity was determined using a Chiralpak™ AD column 25 cm×4.6 mm; Flow 1.0 ml min$^{-1}$; employing UV detection at 254 and 220 nm; eluant hexane:propan-2-ol (95:5)+0.5% (v/v) diethylamine.

Fraction 1 gave the (+)-enantiomer [a]$_D$+49.01 (c 1.00 in MeOH).

NMR ($CDCl_3$, selected data for the free base): 0.8 (d, 3H), 0.85 (m, 3H), 1.25–1.35 (m, 9H), 2.0 (m, 1H), 2.4 (m, 4H), 3.0 (s, 3H), 7.0–7.35 (m, 4H).

MS (thermospray): M/Z [$MH^+$] 367.3; $C_{20}H_{34}N_2O_2S+H$ requires 367.2.

Fraction 2 gave the (−)-enantiomer [a]$_D$−43.88 (c 1.29 in MeOH).

NMR ($CDCl_3$, selected data for the free base) 0.8 (d, 3H), 0.85 (m, 3H), 1.25–1.35 (m, 9H), 2.0 (m, 1H), 2.4 (m, 4H), 3.0 (s, 3H), 7.0–7.35 (m, 4H).

MS (thermospray): M/Z [$MH^+$] 367.3; $C_{20}H_{34}N_2O_2S+H$ requires 367.2.

Example 6

(±)-N-Hexyl-trans-3,4-dimethyl-4-(3-dimethylphosphinoylaminophenyl)piperidine

To a solution of (±)-4-(3-aminophenyl)-N-hexyl-trans-3,4-dimethylpiperidine (Preparation 5, 100 mg, 0.26 mmol) and triethylamine (2.6 ml) in dry dichloromethane (10 ml) under an atmosphere of nitrogen was added dropwise a solution of dimethylphosphinic chloride (234 mg, 0.154 mmol) in dry dichloromethane (2 ml) at 0° C., and the resultant mixture was stirred for 6 h at room temperature. The reaction mixture was diluted with water (20 ml) and extracted with dichloromethane (3×20 ml). The combined extracts were washed with brine (20 ml), dried ($MgSO_4$) and concentrated in vacuo to give the crude product which was purified by silica (3 g) column chromatography, eluting with diethyl ether:hexane:0.880 ammonia (80:20:1) then a gradient elution of ethyl acetate:methanol:0.880 ammonia (100:0:1 to 99:1:1) to give the title compound as a clear oil (38 mg, 40%).

NMR ($CDCl_3$, selected data for the free base): 0.75 (d, 3H), 0.9 (m, 3H), 1.6 (s, 3H), 1.7 (s, 3H), 2.0 (s, 1H), 2.1–2.6 (m, 6H), 2.8 (m, 1H), 4.85 (d, 1H), 6.8–7.2 (m, 4H).

MS (APCI): M/Z [$MH^+$] 365.0; $C_{21}H_{37}N_2OP+H$ requires 365.3.

Example 7

(±)-N-Hexyl-trans-3,4-dimethyl-4-(3-dimethylthiophosphinoylaminophenyl)piperidine To a solution of (±)-4-(3-aminophenyl)-N-hexyl-trans-3,4-dimethylpiperidine (Preparation 5, 100 mg, 0.26 mmol) in dry pyridine (10 ml) under an atmosphere of nitrogen was added dropwise dimethylphosphinothioic chloride (51 mg, 0.4 mmol) at 0° C., and the resultant mixture was stirred for 18 hours at room temperature. The reaction mixture was diluted with water (10 ml) and extracted with diethyl ether (4×20 ml). The combined extracts were dried ($MgSO_4$) and concentrated in vacuo at 60° C. to give the crude product which was purified by preparative thin layer chromatography, eluting with diethyl ether:hexane:0.880 ammonia (75:25:1) to give the title compound as a clear oil (38 mg, 40%).

NMR ($CDCl_3$, selected data for the free base): 0.75 (d, 3H), 0.9 (m, 3H), 1.7 (m, 1H), 1.95 (m, 6H), 2.85 (m, 1H), 4.7 (br.s, 1H), 6.8–7.25 (m, 4H).

MS (thermospray): M/Z [$M^+$] 381.2; $C_{21}H_{37}N_2PS+H$ requires 381.2.

Example 8

(±)-4-(3-Ethanesulfonylaminophenyl)-N-hexyl-trans-3,4-dimethylpiperidine

To a solution of (±)-4-(3-aminophenyl)-N-hexyl-trans-3,4-dimethylpiperidine (Preparation 5, 30 mg, 0.1 mmol) in pyridine (0.6 ml) at 0° C. under nitrogen was added ethanesulfonyl chloride (14 ml, 0.15 mmol), and the resultant mixture was stirred overnight. Ice (1 ml) was added and, after 30 min, the reaction mixture was extracted with diethyl ether (3×5 ml) and dichloromethane (2×5 ml). The combined extracts were dried ($Na_2SO_4$) and concentrated in vacuo to give the crude product. This was purified by silica (5 g) column chromatography eluting with ethyl acetate:hexane:0.880 ammonia (40:60:1) to give the title compound as a pale brown oil (23 mg, 58%).

NMR ($CDCl_3$, selected data for the free base): 0.75 (d, 3H), 0.85 (m, 3H), 2.2–2.6 (m, 6H), 2.8 (m, 1H), 3.1 (q, 2H), 5.2–5.8 (br.s, 1H), 7.0–7.3 (m, 4H).

MS (thermospray): M/Z [$M^+$] 381.3; $C_{21}H_{36}N_2O_2S+H$ requires 381.3.

Example 9

Resolution of the enantiomers of (±)-4-4-(3-ethanesulfonylaminophenyl)-N-hexyl-trans-3,4-dimethylpiperidine The enantiomers of (±)-4-(3-ethanesulfonylaminophenyl)-N-hexyl-trans-3,4-dimethylpiperidine (Example 8) were separated by preparative HPLC on a Chiralpak™ AS column, 25 cm×2.0 cm; Flow 10.0 ml min$^{-1}$; employing UV. detection at 220 nm; eluant hexane:propan-2-ol:diethylamine (95:5:0.5). Enantiomeric purity was determined using a Chiralpak™ AS column 25 cm×0.46 mm; Flow 1.0 ml min$^{-1}$; employing UV detection at 220 nm; eluant hexane:propan-2-ol:diethylamine (95:5:0.5).

Fraction 1 gave the (−)-enantiomer [a]$_D$−51.48 (c 5.39 in MeOH).

NMR (CDCl$_3$, selected data for the free base): 0.75 (d, 3H), 0.9 (m, 3H), 2.0 (m, 1H), 2.3 (m, 4H), 2.55 (m, 2H), 2.8 (m, 1H), 3.1 (q, 2H), 7.0–7.35 (m, 4H).

MS (APCI): M/Z [MH$^+$] 381.0; C$_{21}$H$_{36}$N$_2$O$_2$S+H requires 381.3.

Fraction 2 gave the (+)-enantiomer [a]$_D$+53.25 (c 5.39 in MeOH).

NMR (CDCl$_3$, selected data for the free base): 0.75 (d, 3H), 0.9 (m, 3H), 2.0 (m, 1H), 2.3 (m, 4H), 2.55 (m, 2H), 2.8 (m, 1H), 3.1 (q, 2H), 7.0–7.35 (m, 4H).

MS (APCI): M/Z [MH$^+$] 381.1; C$_{21}$H$_{36}$N$_2$O$_2$S+H requires 381.3.

Example 10

(±)-N-Hexyl-trans-3,4-dimethyl-4-(3-n-propanesulfonylaminophenyl)piperidine

To a solution of (±)-4-(3-aminophenyl)-N-hexyl-trans-3,4-dimethylpiperidine (Preparation 5, 36.9 mg, 0.13 mmol) in pyridine (0.6 ml) under an atmosphere of nitrogen was added n-propanesulfonyl chloride (22 ml, 0.19 mmol) dropwise, and the resultant mixture was stirred for 3 days before hydrolysing with ice (5 g). The reaction mixture was extracted with dichloromethane (2×10 ml) and the combined extracts were dried (Na$_2$SO$_4$), filtered and concentrated in vacuo at 80° C. to give the crude product which was purified by silica (6 g) column chromatography eluting with ethyl acetate:hexane:0.880 ammonia (50:50:1) to give the title compound as a pale yellow oil (39 mg, 73%).

NMR (CDCl$_3$, selected data for the free base): 0.75 (d, 3H), 0.9 (m, 3H), 1.0 (t, 3H), 2.0 (m, 1H), 2.2–2.6 (m, 6H), 2.8 (m, 1H), 3.05 (m, 2H), 7.0–7.3 (m, 4H).

MS (thermospray): M/Z [MH$^+$] 395.2; C$_{22}$H$_{38}$N$_2$O$_2$S+H requires 395.3.

Example 11

(±)-4-(3-n-Butanesulfonylaminophenyl)-N-hexyl-trans-3,4-dimethylpiperidine

To a solution of (±)-4-(3-aminophenyl)-N-hexyl-trans-3,4-dimethylpiperidine (Preparation 5, 37.8 mg, 0.13 mmol) in pyridine (0.6 ml) under an atmosphere of nitrogen was added n-butanesulfonyl chloride (26 ml, 0.20 mmol) dropwise, and the resultant mixture was stirred for 3 days before hydrolysing with ice (5 g). The reaction mixture was extracted with dichloromethane (2×10 ml) and the combined extracts were dried (Na$_2$SO$_4$), filtered and concentrated in vacuo at 80° C. to give the crude product which was purified by silica (6 g) column chromatography eluting with ethyl acetate:hexane:0.880 ammonia (60:40:1) to give the title compound as a pale yellow oil (51 mg, 95%).

NMR (CDCl$_3$, selected data for the free base): 0.75 (d, 3H), 0.9 (m, 3H), 2.0 (m, 1H), 2.2–2.6 (m, 8H), 2.8 (m, 1H), 3.05 (m, 2H), 7.0–7.3 (m, 4H).

MS (thermospray): M/Z [MH$^+$] 409.2; C$_{23}$H$_{40}$N$_2$O$_2$S+H requires 409.3.

Example 12

(±)-4-(3-n-Heptanesulfonylaminophenyl)-N-hexyl-trans-3,4-dimethylpiperidine

To a solution of (±)-4-(3-aminophenyl)-N-hexyl-trans-3,4-dimethylpiperidine (Preparation 5, 50 mg, 0.175 mmol) in pyridine (1 ml) at 0° C. under an atmosphere of nitrogen was added n-heptanesulfonyl chloride (Preparation 6, 69 mg, 0.35 mmol) dropwise, and the resultant mixture was stirred overnight. Ice (1 g) was added and, after 30 min, approx. 3 ml of saturated aqueous sodium bicarbonate solution was added. The mixture was concentrated in vacuo and the residue purified by silica (5 g) column chromatography eluting with dichloromethane. The residue was dissolved in hexane, filtered and the filtrate was concentrated in vacuo. The residue was dissolved in dichloromethane, excess 1M hydrogen chloride in diethyl ether was added and the precipitate was filtered and washed with ether. The solid was dissolved in dichloromethane and excess 0.880 ammonia was added and the mixture was concentrated in vacuo. The residue was dissolved in hexane, filtered and the filtrate was concentrated in vacuo to afford the title compound as an oil (20 mg, 25%).

NMR (CDCl$_3$, selected data for the free base): 0.85 (m, 6H), 1.80 (m, 2H), 3.05 (m, 2H), 7.0–7.3 (m, 4H).

Example 13

(±)-N-Hexyl-trans-3,4-dimethyl-4-(3-(2-methylethane)-sulfonylaminophenyl)piperidine To a solution of (±)-4-(3-aminophenyl)-N-hexyl-trans-3,4-dimethylpiperidine (Preparation 5, 30 mg, 0.1 mmol) in pyridine (0.6 ml) at 0° C. under nitrogen was added isopropylsulfonyl chloride (17 ml, 0.15 mmol) dropwise, and the resultant mixture was stirred overnight. Ice (1 ml) was added and, after 30 min, the reaction mixture was extracted with diethyl ether (3×5 ml) and dichloromethane (2×5 ml). The combined extracts were dried (Na$_2$SO$_4$) and concentrated in vacuo to give the crude product. This was purified by silica (5 g) column chromatography eluting with ethyl acetate:hexane:0.880 ammonia (40:60:1) to give the title compound as a pale brown oil (25 mg, 61%).

NMR (CDCl$_3$, selected data for the free base): 0.75 (d, 3H), 0.85 (m, 3H), 1.5 (m, 1H), 2.0 (m, 1H), 2.2–2.6 (m, 6H), 2.8 (m, 1H), 3.25 (m, 1H), 7.0–7.3 (m, 4H).

MS (thermospray): M/Z [MH$^+$] 395.3; C$_{22}$H$_{38}$N$_2$O$_2$S+H requires 395.3.

Example 14

(±)-4-(3-Cyclohexanesulfonylaminophenyl)-N-hexyl-trans-3,4-dimethylpiperidine

To a solution of (±)-4-(3-aminophenyl)-N-hexyl-trans-3,4-dimethylpiperidine (Preparation 5, 30 mg, 0.10 mmol) in pyridine (0.6 ml) under an atmosphere of nitrogen was added cyclohexanesulfonyl chloride (M. S. Kharasch and A. T. Read, J. Am. Chem. Soc., 1939, 61 3089.), (30 mg, 0.16 mmol), and the resultant mixture was stirred for 18 h before hydrolysing with ice (5 g). The reaction mixture was concentrated in vacuo at 80° C. and the residue was taken up in dichloromethane (20 ml), washed with saturated aqueous sodium hydrogen carbonate solution (10 ml) dried (Na$_2$SO$_4$), filtered and concentrated in vacuo to give the crude product. This was purified by silica (6 g) column chromatography eluting with ethyl acetate:0.880 ammonia (99.8:0.2) to give the title compound as a pale yellow oil (13 mg, 29%).

NMR (CDCl$_3$, selected data for the free base): 0.9 (m, 6H), 1.85 (m, 2H), 2.9–3.0 (m, 3H), 7.0–7.3 (m, 4H).

MS (thermospray): M/Z [MH$^+$] 435.3; C$_{25}$H$_{42}$N$_2$O$_2$S+H requires 435.3.

Example 15

(±)-N-Hexyl-trans-3,4-dimethyl-4-(3-trifluoromethanesulfonylaminophenyl)piperidine To a solution of (±)-4-(3-aminophenyl)-N-hexyl-trans-3,4-dimethylpiperidine (Preparation 5, 40.4 mg, 0.14 mmol)

in pyridine (0.6 ml) under an atmosphere of nitrogen was added trifluoromethanesulfonyl chloride (23 ml, 0.21 mmol) dropwise, and the resultant mixture was stirred for 3 days. Ice (5 g) was added and, after 1 h, the reaction mixture was extracted with dichloromethane (2×10 ml). The combined extracts were washed with water (5 ml), dried ($Na_2SO_4$), filtered and concentrated in vacuo at 80° C to give the crude product which was purified by silica (6 g) column chromatography eluting with methanol:dichloromethane:0.880 ammonia (5:95:1) to give the title compound as a cream solid (5 mg, 8%).

MS (thermospray): M/Z [$MH^+$] 421.0; $C_{20}H_{31}F_3N_2O_2S+H$ requires 421.2.

Example 16

(±)-N-Hexyl-trans-3,4-dimethyl-4-(3-(2,2,2-trifluoroethanesulfonylamino)phenyl)piperidine To a solution of (±)-4-(3-aminophenyl)-N-hexyl-trans-3,4-dimethylpiperidine (Preparation 5, 37.4 mg, 0.13 mmol) in pyridine (0.6 ml) under an atmosphere of nitrogen was added 2,2,2-trifluoroethanesulfonyl chloride (15 ml, 0.20 mmol) dropwise, and the resultant mixture was stirred for 3 days before hydrolysing with ice (5 g). The reaction mixture was extracted with dichloromethane (2×10 ml) and the combined extracts were dried ($Na_2SO_4$), filtered and concentrated in vacuo at 80° C. to give the crude product which was purified by silica (6 g) column chromatography eluting with ethyl acetate:hexane:0.880 ammonia (80:20:1) to give the title compound as a pale yellow oil (15 mg, 27%).

NMR ($CDCl_3$, selected data for the free base): 0.75 (d, 3H), 0.9 (m, 3H), 2.0 (m, 1H), 2.2–2.6 (m, 8H), 2.8 (m, 1H), 3.05 (m, 2H), 7.0–7.3 (m, 4H).

MS (thermospray): M/Z [$MH^+$] 435.4; $C_{21}H_{33}F_3N_2O_2S+H$ requires 435.2.

Example 17

(±)-N-Hexyl-trans-3,4-dimethyl-4-(3-(2-phthalimido-1-ethanesulfonylamino)phenyl)piperidine To a stirred solution of 2-phthalimidoethanesulfonyl chloride (R. Winterbottom et al, J. Am. Chem. Soc., 1947, 69, 1393), (200 mg, 0.73 mmol) in pyridine (1 ml) at room temperature was rapidly added (±)-4-(3-aminophenyl)-N-hexyl-trans-3,4-dimethylpiperidine (Preparation 5, 150 mg, 0.52 mmol) in dichloromethane (2 ml). The reaction mixture was stirred under nitrogen for 16 h, then concentrated in vacuo. The residue was pre-absorbed onto silica gel and purified by silica column chromatography eluting with ethyl acetate:0.880 ammonia (100:1) to give the title compound as a clear oil (230 mg, 84%).

NMR ($CDCl_3$, selected data for free base): 0.77 (d, 3H), 0.90 (t, 3H), 1.22–1.64 (m, 12H), 1.98 (m, 1H), 2.20–2.60 (m, 6H), 2.80 (m, 1H), 3.42 (t, 2H), 4.08 (t, 2H), 7.10 (m, 2H), 7.23 (m, 2H), 7.70 (m, 2H), 7.85 (m, 2H).

MS (thermospray): M/Z [$M+H^+$] 526.6; $C_{29}H_{39}N_3O_4S+H$ requires 526.3.

Example 18

(±)-4-(3-(2-Amino-1-ethanesulfonylamino)phenyl)-N-hexyl-trans-3,4-dimethylpiperidine To a stirred solution of (±)-N-hexyl-trans-3,4-dimethyl-4-(3-(2-phthalimido-1-ethane)sulfonylaminophenyl)piperidine (Example 17, 200 mg, 0.38 mmol) in absolute ethanol (3 ml) was added hydrazine monohydrate (19 mg, 0.38 mmol) in absolute ethanol (1 ml) and the mixture was heated under reflux for 2 h 30 min. The mixture was allowed to cool and the precipitate was removed by filtration and thoroughly washed with ethanol. The filtrate was concentrated in vacuo and the residue was purified by silica column chromatography eluting with ethyl acetate:methanol:0.880 ammonia (80:20:1) to give the title compound as a white solid (80 mg, 53%).

NMR ($CDCl_3$, selected data for free base): 0.78 (d, 3H), 0.88 (t, 3H), 1.22–1.64 (m, 12H), 2.00 (m, 1H), 2.20–2.62 (m, 6H), 2.82 (m, 1H), 3.10–3.24 (m, 4H), 3.50 (s broad, 2H), 7.10 (m, 2H), 7.18 (s, 1H), 7.26 (t, 1H).

MS (thermospray): M/Z [$M+H^+$] 396.5; $C_{21}H_{37}N_3O_2S+H$ requires 396.3.

Example 19

(±)-N-Hexyl-4-(3-(2-methoxy-1-ethanesulfonylamino)phenyl)-trans-3,4-dimethylpiperidine To a stirred solution of (±)-4-(3-aminophenyl)-N-hexyl-trans-3,4-dimethylpiperidine (Preparation 5, 151 mg, 0.53 mmol) in dichloromethane (3 ml) at room temperature was added pyridine (83 mg, 1.05 mmol) in dichloromethane (1 ml) and 2-methoxy-ethanesulfonyl chloride (J. F. King, J. Y. L. Lam and S. Skonieczny, J. Am. Chem. Soc., 1992, 114, 1743), (116 mg, 0.74 mmol) in dichloromethane (1 ml). The reaction mixture was stirred under nitrogen for 16 h, then concentrated in vacuo. The residue was pre-absorbed onto silica gel and purified by silica column chromatography eluting with ethyl acetate:hexane (1:1) and then with ethyl acetate:hexane:ammonium hydroxide (90:10:1) to give the title compound as a clear oil (180 mg, 84%).

NMR ($CDCl_3$, selected data for free base): 0.79 (d, 3H), 0.90 (t, 3H), 3.21 (t, 2H), 3.41 (s, 3H), 3.82 (t, 2H), 7.06 (d, 1H), 7.15 (d, 1H), 7.20 (s, 1H), 7.28 (t, 1H).

MS (thermospray): M/Z [$M+H^+$] 411.4; $C_{22}H_{38}N_2O_3S+H$ requires 411.3.

Example 20

(±)-N-Hexyl-4-(3-(2-hydroxy-1-ethanesulfonylamino)phenyl)-trans-3,4-dimethylpiperidine To a stirred solution of (±)-N-hexyl-4-(3-(2-methoxy-1-ethane)sulfonylaminophenyl)-trans-3,4-dimethylpiperidine (Example 19, 50 mg, 0.12 mmol) was added 48% aqueous hydrobromic acid (3 ml) and the mixture was stirred at room temperature for 16 h, and then heated under reflux for 6 h. The reaction mixture-was allowed to cool to room temperature and the pH was cautiously adjusted to 13 using solid sodium hydroxide. The basic aqueous solution was extracted with diethyl ether (3×5 ml). The combined extracts were dried ($MgSO_4$), filtered and concentrated in vacuo to give the crude product which was purified by silica column chromatography eluting with ethyl acetate:ammonium hydroxide (100:1) to give the title compound as a clear oil (12 mg, 25%).

NMR (CDCl$_3$, selected data for free base): 0.78 (d, 3H), 0.90 (t, 3H), 1.26–1.37 (m, 9H), 1.40–1.56 (m, 2H), 1.60 (m, 1H), 1.99 (m, 1H), 2.20–2.60 (m, 6H), 2.81 (m, 1H), 3.27 (t, 2H), 4.10 (t, 2H), 7.06 (d, 1H), 7.17 (d, 1H), 7.19 (s, 1H), 7.28 (t, 1H).

MS (thermospray): M/Z [M+H$^+$] 397.4; C$_{21}$H$_{36}$N$_2$O$_3$S+H requires 397.3.

Example 21

(±)-4-(Ethoxycarbonylmethylsulfonylaminophenyl)-N-hexyl-trans-3,4-dimethylpiperidine To a stirred solution of ethyl 2-(chlorosulfonyl)acetate (J. E. Oliver and A. B. DeMilo, Synthesis, 1975, 321–322), (36 mg, 0.19 mmol) in dichloromethane (1 ml) at room temperature was added triethylamine (26 mg, 0.26 mmol) and then (±)-4-(3-aminophenyl)-N-hexyl-trans-3,4-dimethylpiperidine (Preparation 5, 50 mg, 0.175 mmol) in dichloromethane (1 ml). The reaction mixture was stirred under nitrogen for 16 h, then concentrated in vacuo. The residue was pre-absorbed onto silica gel and purified by silica column chromatography eluting with ethyl acetate:hexane (1:2) to give the title compound as a clear oil (41 mg, 54%).

NMR (CDCl$_3$, selected data for the free base): 0.76 (d, 3H), 0.90 (t, 3H), 1.20–1.39 (m, 12H), 1.43–1.54 (m, 2H), 1.61 (m, 1H), 2.00 (m, 1H), 2.20–2.60 (m, 6H), 2.82 (m, 1H), 3.90 (s, 2H), 4.28 (q, 2H), 7.10–7.20 (m, 2H), 7.24–7.30 (m, 2H).

MS (thermospray): M/Z [MH$^+$] 439.4; C$_{23}$H$_{38}$N$_2$O$_4$S+H requires 439.3.

Example 22

(±)-4-(3-(Aminocarbonylmethanesulfonylamino) phenyl)-N-hexyl-trans-3,4-dimethylpiperidine To a solution of ammonia in methanol (2.5 ml, 2.0 M) was added (±)-4-(ethoxycarbonylethylsulfonylaminophenyl)-N-hexyl-trans-3,4-dimethylpiperidine (Example 21, 66 mg, 0.15 mmol) in methanol (1 ml) and the vessel was sealed and heated at 50° C. for 16 h. The mixture was allowed to cool to room temperature and then concentrated in vacuo. The residue was purified by silica column chromatography eluting with ethyl acetate:methanol:0.880 ammonia (94:6:1) to give the title compound as a glassy solid (42 mg, 68%).

NMR (CDCl$_3$, selected data for the free base): 0.77 (d, 3H), 0.95 (t, 3H), 1.22–1.65 (m, 12H), 1.98 (m, 1H), 2.20–2.60 (m, 6H), 2.81 (m, 1H), 3.85 (s, 2H), 6.01 (s, 1H), 6.40 (s, 1H), 7.18 (m, 2H), 7.30 (m, 2H).

MS (APCI): M/Z [M+H$^+$] 410.4; C$_{21}$H$_{35}$N$_3$O$_3$S+H requires 410.2.

Example 23

(±)-N-Hexyl-trans-3,4-dimethyl-4-(3-a-toluenesulfonylaminophenyl)piperidine

To a solution of (±)-4-(3-aminophenyl)-N-hexyl-trans-3,4-dimethylpiperidine (Preparation 5, 34.6 mg, 0.12 mmol) in pyridine (0.6 ml) under an atmosphere of nitrogen was added a-toluenesulfonyl chloride (34 mg, 0.18 mmol), and the resultant mixture was stirred overnight. Ice (2 g) was added and, after 1 h, the reaction mixture was extracted with dichloromethane (2×10 ml). The combined extracts were washed with water (2 ml), dried (Na$_2$SO$_4$) and concentrated in vacuo at 80° C. to give the crude product which was purified by silica (6 g) column chromatography eluting with ethyl acetate:hexane:0.880 ammonia (40:60:1) to give the title compound as a pale yellow oil (52 mg, 98%).

NMR (CDCl$_3$, selected data for the free base): 0.8 (d, 3H), 0.9 (m, 3H), 2.0 (m, 1H), 2.1–2.6 (m, 6H), 2.8 (m, 1H), 4.35 (s, 2H), 7.0–7.4 (m, 9H).

MS (thermospray): M/Z [MH$^+$] 443.2; C$_{26}$H$_{38}$N$_2$O$_2$S+H requires 443.3.

Example 24

(±)-4-(3-Benzenesulfonylaminophenyl)-N-hexyl-trans-3,4-dimethylpiperidine

To a solution of (±)-4-(3-aminophenyl)-N-hexyl-trans-3,4-dimethylpiperidine (Preparation 5, 35.6 mg, 0.124 mmol) in pyridine (0.6 ml) under an atmosphere of nitrogen was added benzenesulfonyl chloride (24 ml, 0.186 mmol) dropwise, and the resultant mixture was stirred overnight. Ice (2 g) was added and, after 1 h, the reaction mixture was extracted with dichloromethane (2×10 ml). The combined extracts were washed with water (2 ml), dried (Na$_2$SO$_4$) and concentrated in vacuo at 80° C. to give the crude product which was purified by silica (6 g) column chromatography eluting with ethyl acetate:hexane:0.880 ammonia (40:60:1) to give the title compound as a pale yellow oil (50 mg, 95%).

NMR (CDCl$_3$, selected data for the free base): 0.6 (d, 3H), 0.9 (m, 3H), 1.85 (m, 1H), 2.15–2.55 (m, 6H), 2.75 (m, 1H), 6.85–7.75 (m, 9H).

MS (thermospray): M/Z [MH$^+$] 429.3; C$_{25}$H$_{36}$N$_2$O$_2$S+H requires 429.3.

Example 25

(±)-N-Hexyl-trans-3,4-dimethyl-4-(3-(2-methylbenzenesulfonylamino)phenyl)piperidine To a stirred solution of (±)-4-(3-aminophenyl)-N-hexyl-trans-3,4-dimethylpiperidine (Preparation 5, 54 mg, 0.19 mmol) and pyridine (29 mg, 0.37 mmol) in dichloromethane (2 ml) at 0° C. was added 2-methylbenzenesulfonyl chloride (58 mg, 0.28 mmol). The reaction mixture was stirred at room temperature for 64 h, then concentrated in vacuo. The residue was purified by silica (5 g) column chromatography eluting initially with hexane, then hexane:ethyl acetate:0.880 ammonia (50:50:1) to give the title compound as a yellow oil (49 mg, 60%).

NMR (CDCl$_3$, selected data for the free base): 0.6 (m, 3H), 0.9 (m, 3H), 1.2 (m, 3H), 1.5 (br. s, 3H), 1.85 (m, 1H), 2.6 (s, 3H), 2.75 (m, 1H), 6.8–7.3 (m, 8H).

MS (APCI): M/Z [MH$^+$] 443.4; C$_{26}$H$_{38}$N$_2$O$_2$S+H requires 443.3.

Example 26

(±)-N-Hexyl-trans-3,4-dimethyl-4-(3-(3-methylbenzenesulfonylamino)phenyl)piperidine To a stirred solution of (±)-4-(3-aminophenyl)-N-hexyl-trans-3,4-dimethylpiperidine (Preparation 5, 54 mg, 0.19 mmol) and pyridine (29 mg, 0.37 mmol) in dichloromethane (2 ml) at 0° C. was added 3-methylbenzenesulfonyl chloride (58 mg, 0.28 mmol). The reaction mixture was stirred at room temperature for 64 h, then concentrated in vacuo. The residue was purified by silica (5 g) column chromatography eluting initially with hexane, then hexane:ethyl acetate:0.880 ammonia (50:50:1) to give the title compound as a yellow oil (70 mg, 85%)

NMR (CDCl$_3$, selected data for the free base): 0.64 (d, 3H), 0.88 (m, 3H), 1.23 (s, 3H), 1.30 (m, 6H), 1.50 (m, 3H), 1.90 (m, 1H), 2.12–2.40 (m, 7H), 2.40–2.56 (m, 2H), 2.74 (m, 1H), 6.86 (d, 1H), 6.96 (s, 1H), 7.05 (d, 1H), 7.18 (t, 1H), 7.29 (m, 2H), 7.53 (s, 2H).

MS (APCI): M/Z [MH$^+$] 443.4; C$_{26}$H$_{38}$N$_2$O$_2$S+H requires 443.3.

Example 27

(±)-N-Hexyl-trans-3,4-dimethyl-4-(3-(4-methylbenzenesulfonylamino)phenyl)piperidine To a stirred solution of (±)-4-(3-aminophenyl)-N-hexyl-trans-3,4-dimethylpiperidine (Preparation 5, 54 mg, 0.19 mmol) and pyridine (29 mg, 0.37 mmol) in dichloromethane (2 ml) at 0° C. was added 4-methylbenzenesulfonyl chloride (58 mg, 0.28 mmol). The reaction mixture was stirred at room temperature for 64 h, then concentrated in vacuo. The residue was purified by silica (5 g) column chromatography eluting initially with hexane, then hexane:ethyl acetate:0.880 ammonia (50:50:1) to give the title compound as a yellow oil (70 mg, 84%).

NMR (CDCl$_3$, selected data for the free base) 0.62 (d, 3H), 0.90 (m, 3H), 1.22 (s, 3H), 1.24 (m, 6H), 1.48 (m, 3H), 1.88 (m, 1H), 2.12–2.55 (m, 9H), 2.75 (m, 1H), 6.88 (d, 1H), 6.95 (s, 1H), 7.03 (d, 1H), 7.17 (m, 3H), 7.64 (d, 2H).

Example 28

(±)-N-Hexyl-4-(3-(4-methoxybenzenesulfonylamino)phenyl)-trans-3,4-dimethylpiperidine To a stirred solution of (±)-4-(3-aminophenyl)-N-hexyl-trans-3,4-dimethylpiperidine (Preparation 5, 54 mg, 0.19 mmol) and pyridine (29 mg, 0.37 mmol) in dichloromethane (2 ml) at 0° C. was added 4-methoxybenzenesulfonyl chloride (62 mg, 0.28 mmol). The reaction mixture was stirred at room temperature for 64 h, then concentrated in vacuo. The residue was purified by silica (5 g) column chromatography eluting initially with hexane, then hexane:ethyl acetate:0.880 ammonia (50:50:1) to give the title compound as a yellow oil (35 mg, 41%).

NMR (CDCl$_3$, selected data for the free base): 0.64 (d, 3H), 0.88 (m, 3H), 1.23 (s, 3H), 1.30 (m, 6H), 1.50 (m, 3H), 1.90 (m, 1H), 2.14–2.57 (m, 6H), 2.78 (m, 1H), 3.82 (s, 3H), 6.80–7.18 (m, 6H), 7.66 (d, 2H).

Example 29

(±)4-(3-(2-Chlorobenzenesulfonylamino)phenyl)-N-hexyl-trans-3,4-dimethylpiperidine To a stirred solution of (±)-4-(3-aminophenyl)-N-hexyl-trans-3,4-dimethylpiperidine (Preparation 5, 54 mg, 0.19 mmol) and pyridine (29 mg, 0.37 mmol) in dichloromethane (2 ml) at 0° C. was added 2-chlorobenzenesulfonyl chloride (59 mg, 0.28 mmol). The reaction mixture was stirred at room temperature for 64 h, then concentrated in vacuo. The residue was purified by silica (5 g) column chromatography eluting initially with hexane, then hexane:ethyl acetate:0.880 ammonia (50:50:1) to give the title compound as a yellow oil (71 mg, 82%).

NMR (CDCl$_3$, selected data for the free base): 0.5 (d, 3H), 0.9 (m, 3H), 1.2 (s, 3H), 1.4–1.5 (m, 3H), 1.85 (m, 1H), 2.1–2.55 (m, 6H), 2.75 (m, 1H), 6.9–7.45 (m, 7H), 7.95 (d, 1H).

MS (APCI): M/Z [MH$^+$] 463.0; C$_{25}$H$_{35}$ClN$_2$O$_2$S+H requires 463.2.

Example 30

(±)-4-(3-(3-Chlorobenzenesulfonylamino)phenyl)-N-hexyl-trans-3,4-dimethylpiperidine To a stirred solution of (±) 4-(3-aminophenyl)-N-hexyl-trans-3,4-dimethylpiperidine (Preparation 5, 54 mg, 0.19 mmol) and pyridine (29 mg, 0.37 mmol) in dichloromethane (2 ml) at 0° C. was added 3-chlorobenzenesulfonylchloride (59 mg, 0.28 mmol). The reaction mixture was stirred at room temperature for 64 h, then concentrated in vacuo. The residue was purified by silica (5 g) column chromatography eluting initially with hexane, then hexane:ethyl acetate:0.880 ammonia (50:50:1) to give the title compound as a yellow oil (37 mg, 43%).

NMR (CDCl$_3$, selected data for the free base): 0.65 (d, 3H), 0.90 (m, 3H), 1.24 (s, 3H), 1.30 (m, 6H), 1.50 (m, 3H), 1.90 (m, 1H), 2.12–2.60 (m, 6H), 2.76 (m, 1H), 6.91 (m, 1H), 6.99 (s, 1H), 7.09 (m, 1H), 7.20 (t, 1H), 7.34 (t, 1H), 7.48 (d, 1H), 7.62 (d, 1H), 7.74 (s, 1H).

Example 31

(±)-4-(3-(4-Chlorobenzenesulfonylamino)phenyl)-N-hexyl-trans-3,4-dimethylpiperidine To a solution of (±)-4-(3-aminophenyl)-N-hexyl-trans-3,4-dimethylpiperidine (Preparation 5, 38.4 mg, 0.133 mmol) in pyridine (0.6 ml) under an atmosphere of nitrogen was added 4-chlorobenzenesulfonyl chloride (42 mg, 0.2 mmol), and the resultant mixture was stirred overnight. Ice (2 g) was added and, after 1 h, the reaction mixture was extracted with dichloromethane (2×10 ml). The combined extracts were washed with water (2 ml), dried (Na$_2$SO$_4$) and concentrated in vacuo at 80° C. to give the crude product which was purified by silica (6 g) column chromatography eluting with ethyl acetate:hexane:0.880 ammonia (40:60:1) to give the title compound as a pale yellow oil (57 mg, 92%).

NMR (CDCl$_3$, selected data for the free base): 0.6 (d, 3H), 0.9 (m, 3H), 1.9 (m, 1H), 2.15–2.55 (m, 6H), 2.75 (m, 1H), 6.85–7.7 (m, 8H).

MS (thermospray): M/Z [M$^+$] 463.2; C$_{25}$H$_{35}$ClN$_2$O$_2$S requires 463.2.

Example 32

(±)-N-Hexyl-trans-3,4-dimethyl-4-(3-(3-pyridinesulfonylamino)phenyl)piperidine

To a solution of (±)-4-(3-aminophenyl)-N-hexyl-trans-3,4-dimethylpiperidine (Preparation 5, 50 mg, 0.174 mmol) in pyridine (1 ml) under an atmosphere of nitrogen was added 3-pyridinesulfonyl chloride (G. Machek, Monatsh. Chem., 1939, 72, 77), (62 mg, 0.348 mmol), and the resultant mixture was stirred for 18 h before hydrolysing with ice (1 g). The reaction mixture was concentrated in vacuo at 80° C. and the residue was taken up in dichloromethane (20 ml), washed with saturated aqueous sodium hydrogen carbonate solution (10 ml), dried (Na$_2$SO$_4$), filtered and concentrated in vacuo. The residue was purified by silica (5 g) column chromatography eluting with dichloromethane then dichloromethane:methanol:0.880 ammonia (90:10:1). The residue further was purified by silica (5 g) column chromatography eluting with ethyl acetate then ethyl acetate:2N ammonia in methanol (90:10) to give a yellow solid. This was dissolved in dichloromethane, diethyl ether was added and the resulting precipitate was filtered to afford the title compound as a pale yellow solid (28 mg, 38%).

NMR (CDCl$_3$, selected data for the free base): 0.85 (d, 3H), 1.35 (s, 3H), 6.9–7.4 (m, 4H), 8.1 (m, 1H), 8.3 (m, 1H), 8.9 (m, 1H), 9.1 (m, 1H).

MS (thermospray): M/Z [MH$^+$] 430.6; C$_{24}$H$_{35}$N$_3$O$_2$S+H requires 430.3.

Example 33

(±)-N-Hexyl-trans-3,4-dimethyl-4-(3-(8-quinolinesulfonylamino)phenyl)piperidine

To a stirred solution of (±)-4-(3-aminophenyl)-N-hexyl-trans-3,4-dimethylpiperidine (Preparation 5, 36 mg, 0.125 mmol) in dichloromethane (1 ml) at room temperature was added pyridine (0.2 ml, 1.0 M solution in dichloromethane) and 8-quinolinesulfonyl chloride (47 mg, 0.2 mmol) in dichloromethane (0.5 ml). The reaction mixture was stirred under nitrogen for 16 h, then concentrated in vacuo. The residue was pre-absorbed onto silica gel and purified by silica column chromatography eluting with ethyl acetate::hexane:ammonium hydroxide (90:10:1) then with ethyl acetate:methanol:ammonium hydroxide (96:4:1) to give the title compound as a clear oil (36 mg, 60%).

NMR (CDCl$_3$, selected data for the free base): 0.4 (d, 3H), 0.85 (m, 3H), 1.1 (s, 3H), 2.0 (m, 1H), 2.6 (m, 1H), 6.8–7.05 (m, 4H), 7.5–7.65 (m, 2H), 8.0 (d, 1H), 8.2–8.3 (m, 2H), 9.2 (d, 1H).

MS (electrospray): M/Z [MH$^+$] 480.3; C$_{28}$H$_{37}$N$_3$SO$_2$+H requires 480.3.

Example 34

(±)-N-Hexyl-4-(3-(5-isoquinolinesulfonylamino)phenyl)-trans-3,4-dimethylpiperidine To a stirred solution of (±)-4-(3-aminophenyl)-N-hexyl-trans-3,4-dimethylpiperidine (Preparation 5, 36 mg, 0.125 mmol) in dichloromethane (1 ml) at room temperature was added pyridine (0.2 ml, 1.0 M solution in dichloromethane) and 5-isoquinolinesulfonyl chloride (47 mg, 0.2 mmol) in dichloromethane (0.5 ml). The reaction mixture was stirred under nitrogen for 16 h, then concentrated in vacuo. The residue was then pre-absorbed onto silica and purified by silica column chromatography eluting with ethyl acetate and then with ethyl acetate:methanol:ammonium hydroxide (95:5:1) to give the title compound as a clear oil (21 mg, 35%).

NMR (CDCl$_3$, selected data for the free base): 0.5 (d, 3H), 0.9 (m, 3H), 1.1 (s, 3H), 2.1 (m, 1H), 2.7 (m, 1H), 6.7–7.1 (m, 4H), 7.6 (m, 1H), 8.1 (d, 1H), 8.3–8.4 (m, 2H), 8.65 (d, 1H), 9.3 (d, 1H).

MS (thermospray): M/Z [MH$^+$] 480.2; C$_{28}$H$_{37}$N$_3$SO$_2$+H requires 480.3.

Example 35

(±)-N-Hexyl-trans-3,4-dimethyl-4-(3-(1-methyl-1H-imidazole-4-sulfonylamino)phenyl)piperidine To a solution of (±)-4-(3-aminophenyl)-N-hexyl-trans-3,4-dimethylpiperidine (Preparation 5, 34 mg, 0.12 mmol) in pyridine (0.5 ml) under an atmosphere of nitrogen was added 1-methyl-1H-imidazole-4-sulfonyl chloride (32 mg, 0.18 mmol), and the resultant mixture was stirred for 3 d. The reaction mixture was diluted with 0.5N aqueous sodium hydroxide solution (10 ml) and extracted with dichloromethane (2×10 ml). The combined extracts were washed with water (10 ml) and brine (10 ml), dried (Na$_2$SO$_4$), filtered and concentrated in vacuo at 80° C. to give the crude product. This was purified by silica (6 g) column chromatography eluting with methanol:dichloromethane:0.880 ammonia (10:90:1) to give the title compound as a cream solid (38 mg, 74%).

NMR (CDCl$_3$, selected data for the free base): 0.6 (d, 3H), 0.85 (m, 3H), 1.9 (m, 1H), 2.2–2.6 (m, 6H), 2.8 (m, 1H), 3.6 (s, 3H), 7.0–7.45 (m, 6H).

Example 36

(±)-N-Hexyl-trans-3,4-dimethyl-4-(3-(3,5-dimethyl-4-isoxazolesulfonylamino)phenyl)piperidine To a stirred solution of (±)-4-(3-aminophenyl)-N-hexyl-trans-3,4-dimethylpiperidine (Preparation 5, 36 mg, 0.125 mmol) in dichloromethane (1 ml) at room temperature was added pyridine (0.2 ml, 1.0 M solution in dichloromethane) and 3,5-dimethyl-4-isoxazolesulfonyl chloride (41 mg, 0.2 mmol) in dichloromethane (0.5 ml). The reaction mixture was stirred under nitrogen for 16 h, then concentrated in vacuo. The residue was pre-absorbed onto silica gel and purified by silica column chromatography on eluting with ethyl acetate:hexane (1:2) and then with ethyl acetate:hexane (1:1) to give the title compound as a yellow oil (42 mg, 75%).

NMR (CDCl$_3$, selected data for the free base): 0.7 (d, 3H), 0.9 (m, 3H), 1.40–1.60 (m, 3H), 1.95 (m, 1H), 2.25 (s, 3H), 2.4 (s, 3H), 2.8 (m, 1H), 6.9–7.3 (m, 4H).

MS (APCI): M/Z [MH$^+$] 448.3; C$_{24}$H$_{37}$N$_3$SO$_3$+H requires 448.3.

Example 37

(±)-4-(3-(5-Chloro-1,3-dimethyl-1H-pyrazole-4-sulfonylamino)phenyl)-N-hexyl-trans-3,4-dimethylpiperidine To a stirred solution of (±)-4-(3-aminophenyl)-N-hexyl-trans-3,4-dimethylpiperidine (Preparation 5, 36 mg, 0.125 mmol) in dichloromethane (1.0 ml) at room temperature was added pyridine (0.2 ml, 1.0 M solution in dichloromethane) and 5-chloro-1,3-dimethyl-1H-pyrazole-4-sulfonyl chloride (48 mg, 0.2 mmol) in dichloromethane (0.5 ml). The reaction mixture was stirred under nitrogen for 16 h, then concentrated in vacuo. The residue was pre-absorbed onto silica gel and purified by silica column chromatography on eluting with ethyl acetate:hexane (1:2) and then with ethyl acetate:hexane (1:1) to give the title compound as a yellow oil (32 mg, 53%).

NMR (CDCl$_3$, selected data for the free base): 0.65 (d, 3H), 0.9 (t, 3H), 1.95 (m, 1H), 2.25 (s, 3H), 2.8 (m, 1H), 3.7 (s, 3H), 6.85–7.2 (m, 4H).

MS (APCI): M/Z [MH$^+$] 481.2; C$_{24}$H$_{37}$N$_4$SO$_2$Cl+H requires 481.2.

Example 38

(±)-4-(3-(2,1,3-Benzoxadiazolesulfonylamino)phenyl)-N-hexyl-trans-3,4-dimethylpiperidine To a stirred solution of (±)-4-(3-aminophenyl)-N-hexyl-trans-3,4-dimethylpiperidine (Preparation 5, 36 mg, 0.125 mmol) in dichloromethane (1.0 ml) at room temperature was added pyridine (0.2 ml, 1.0 M solution in dichloromethane) and 2,1,3-benzoxadiazole-4-sulfonyl chloride (45 mg, 0.2 mmol) in dichloromethane (0.5 ml). The reaction was stirred under nitrogen for 16 h, then concentrated in vacuo. The residue was then pre-absorbed onto silica gel and purified by silica column chromatography eluting with ethyl acetate:hexane (1:2) to give the title compound as a yellow oil (29 mg, 49%).

NMR (CDCl$_3$, selected data for free base): 0.45 (d, 3H), 0.9 (t, 3H), 1.15 (s, 3H), 1.75 (m, 1H), 2.70 (m, 1H), 6.85–7.1 (m, 4H), 7.4 (m, 1H), 7.9–8.05 (m, 2H).

MS (APCI): M/Z [M+H$^+$]471.3; C$_{25}$H$_{34}$N$_4$O$_3$S requires 471.2.

Example 39

(±)-N-Hexyl-trans-3,4-dimethyl-4-(3-sulfamoylaminophenyl)piperidine

To a solution of chlorosulfonamide (R. Graf, Chem. Ber., 1959, 92, 509), (Caution: Air sensitive, 20 mg, 0.174 mmol) in anhydrous toluene (0.5 ml) under nitrogen was added a solution of (±)-4-(3-aminophenyl)-N-hexyl-trans-3,4-dimethylpiperidine (Preparation 5, 50 mg, 0.173 mmol) in toluene (0.5 ml) dropwise over 0.5 min. After 30 min, a further aliquot of chlorosulfonamide (20 mg, 0.174 mmol) in toluene (0.5 ml) was added and the resultant mixture was stirred for a further 30 min. The pH of the mixture was adjusted to 14 using 2N aqueous sodium hydroxide solution, and the mixture was extracted with dichloromethane (2×5 ml). The combined extracts were washed with water (5 ml), dried (Na$_2$SO$_4$) and concentrated in vacuo at 80° C. to give the crude product which was purified by silica column chromatography eluting with a gradient of ethyl acetate:hexane:0.880 ammonia (50:50:1 to 90:10:1) to give the title compound as an oil (9 mg, 15%).

NMR (CDCl$_3$, selected data for the free base): 0.75 (d, 3H), 0.9 (m, 3H), 1.5 (br. s 1H), 1.6 (m, 1H), 2.0 (m, 1H), 2.2–2.6 (m, 6H), 2.8 (m, 1H), 7.0–7.35 (m, 4H).

MS (thermospray): M/Z [MH$^+$] 368.4; C$_{19}$H$_{33}$N$_3$O$_2$S+H requires 368.2.

Example 40

(±)-N-Hexyl-trans-3,4-dimethyl-4-(3-N-isopropylsulfamoylaminophenyl)piperidine

To a stirred solution of (±)-4-(3-aminophenyl)-N-hexyl-trans-3,4-dimethylpiperidine (Preparation 5, 150 mg, 0.52 mmol) in dichloromethane (2 ml) at room temperature was added pyridine (82 mg, 1.04 mmol) and isopropylsulfamoyl chloride (J. A. Kloek and K. L. Leschinsky, J. Org. Chem., 1976, 41, 4028), (115 mg, 0.73 mmol) in dichloromethane (2 ml). The reaction mixture was stirred under nitrogen for 3 h, then concentrated in vacuo. The residue was pre-absorbed onto silica gel and purified by silica column chromatography eluting with ethyl acetate:hexane (1:1) to give the title compound as a white solid (100 mg, 47%).

NMR (CDCl$_3$, selected data for free base): 0.8 (d, 3H), 0.9 (m, 3H), 1.2–1.6 (m, 12H), 2.0 (m, 1H), 2.2–2.6 (m, 6H), 2.8 (m, 1H), 3.55 (m, 1H), 4.35 (d, 1H), 7.0–7.25 (m, 4H).

MS (thermospray): M/Z [MH$^+$] 410.5; C$_{22}$H$_{39}$N$_3$SO$_2$+H requires 410.3.

Example 41

(±)-N-Hexyl-trans-3,4-dimethyl-4-(3-(N,N-dimethylsulfamoylamino)phenyl)piperidine To a solution of (±)-4-(3-aminophenyl)-N-hexyl-trans-3,4-dimethylpiperidine (Preparation 5, 38.1 mg, 0.132 mmol) in pyridine (0.6 ml) under an atmosphere of nitrogen was added N,N-dimethylsulfamoyl chloride (22 ml, 0.2 mmol) dropwise, and the resultant mixture was stirred overnight. Ice (2 g) was added and, after 1 h, the reaction mixture was extracted with dichloromethane (2×10 ml). The combined extracts were washed with water (2 ml), dried (Na$_2$SO$_4$) and concentrated in vacuo at 80° C. to give the crude product which was purified by silica (6 g) column chromatography eluting with ethyl acetate:hexane:0.880 ammonia (40:60:1) to give the title compound as a yellow oil (40 mg, 77%).

NMR (CDCl$_3$, selected data for the free base): 0.75 (d, 3H), 0.9 (m, 3H), 2.0 (m, 1H), 2.2–2.6 (m, 6H), 2.75 (br. s, 1H), 2.8 (m, 1H), 3.75 (m, 2H), 7.05–7.3 (m, 4H).

MS (thermospray): M/Z [MH$^+$] 396.3; C$_{21}$H$_{37}$N$_3$O$_2$S+H requires 396.3.

Example 42

(±)-N-Benzyl-4-(3-(2-hydroxy-2-methylpropanoylamino)phenyl)-trans-3,4-dimethylpiperidine To a solution of (±)-N-benzyl-4-(3-(1-carbamoyl-1-methylethoxy)phenyl)-trans-3,4-dimethylpiperidine (Preparation 8, 12.77 g, 33.6 mmol) in N,N-dimethylformamide (330 ml) under an atmosphere of nitrogen was added solid sodium hydride (1.65 g, 69 mmol) in four portions over 30 min. The resultant mixture was stirred for 1 h and then heated under reflux overnight. The reaction mixture was cooled, carefully treated with water (200 ml) and stirred for 1 h. It was then further diluted with water (300 ml) and extracted with diethyl ether (3×500 ml). The combined extracts were washed with water (300 ml) and brine (300 ml), dried (Na$_2$SO$_4$) and concentrated in vacuo to give a yellow foam (14.25 g) which was purified by silica (500 g) column chromatography eluting with a gradient of ethyl acetate:hexane:0.880 ammonia (25:75:1 to 30:70:1 to 40:60:1) to give the title compound as a cream solid (10.16 g, 80%).

NMR (CDCl$_3$, selected data for the free base): 0.8 (d, 3H), 1.35 (s, 3H), 1.55 (m, 6H), 2.0 (m, 1H), 2.1–2.9 (m, 6H), 3.4–3.65 (m, 2H), 7.0–7.55 (m, 9H), 8.65 (br.s, 1H).

MS (thermospray): M/Z [MH$^+$] 381.2; C$_{24}$H$_{32}$N$_2$O$_2$+H requires 381.3.

Example 43

(±)-N-Benzyl-4-(3-methanesulfonylaminophenyl)-trans-3,4-dimethylpiperidine

To a solution of (±)-4-(3-aminophenyl)-N-benzyl-trans-3,4-dimethylpiperidine (Preparation 9, 6.1 g, 20.7 mmol) in pyridine (50 ml) at 0° C. under an atmosphere of nitrogen was added methanesulfonyl chloride (2.4 ml, 31.0 mmol) dropwise, and the resultant mixture was stirred overnight. Ice (200 g) was added and, after 1 h, the reaction mixture was extracted with diethyl ether (3×150 ml). The combined extracts were dried (Na$_2$SO$_4$) and concentrated in vacuo at 80° C. to give the crude product which was purified by silica (200 g) column chromatography, eluting with ethyl acetate:hexane:0.880 ammonia (40:60:1) to give the title compound as a pale brown oil (6.63 g, 87%).

NMR (CDCl$_3$, selected data for the free base): 0.8 (d, 3H), 1.35 (s, 3H), 1.95 (m, 1H), 2.35 (m, 2H), 2.55 (m, 2H), 2.85 (m, 1H), 3.0 (s, 3H), 3.55 (m, 2H), 7.0–7.4 (m, 9H).

MS (thermospray): M/Z [MH$^+$] 373.5; C$_{21}$H$_{28}$N$_2$O$_2$S+H requires 373.2.

Example 44

(±)-4-(3-Methanesulfonylaminophenyl)-trans-3,4-dimethyl-N-(5-methylhexyl)piperidine To a stirred solution of (±)-4-(3-methanesulfonylaminophenyl)-trans-3,4-dimethylpiperidine (Preparation 10, 25 mg, 0.088 mmol) in N,N-dimethylformamide (2 ml) was added sodium hydrogen carbonate (11 mg, 0.13 mmol) and 1-bromo-5-methylhexane (20 mg, 0.11 mmol). The reaction was heated to 90° C. for 24 h and then cooled to room temperature. The reaction mixture was diluted with water (40 ml) and extracted with diethyl ether (2×20 ml). The combined extracts were dried ($MgSO_4$), filtered and concentrated in vacuo to give the crude product. This was purified by silica (5 g) column chromatography eluting with ethyl acetate:hexane (4:1) to give the title compound as a light brown gum (11 mg, 32%).

NMR ($CDCl_3$, selected data for the free base): 0.75 (d, 3H), 0.8 (m, 6H), 1.2 (m, 3H), 2.55 (m, 2H), 3.0 (s, 3H), 7.0–7.4 (m, 4H).

MS (thermospray): M/Z [$MH^+$] 381.3; $C_{21}H_{36}N_2O_2S+H$ requires 381.3.

Example 45

(±)-N-(3-Hydroxypropyl)-4-(3-methanesulfonylaminophenyl)-trans-3,4-dimethylpiperidine To a stirred solution of (±)-4-(3-methanesulfonylaminophenyl)-trans-3,4-dimethylpiperidine (Preparation 10, 500 mg, 1.77 mmol) in N,N-dimethylformamide (4 ml) was added sodium hydrogen carbonate (165 mg, 1.96 mmol) and 3-bromo-1-propanol (175 ml, 1.94 mmol). The stirred reaction mixture was heated under reflux for 45 min, then concentrated in vacuo to give the crude product as a brown oil which was purified by silica (46 g) column chromatography eluting with dichloromethane:methanol:0.880 ammonia (150:8:1) to give the title compound as a yellow oil (450 mg, 75%).

NMR ($CDCl_3$, selected data for the free base): 0.7 (d, 3H), 1.3 (s, 3H), 1.55–1.85 (m, 3H), 2.0 (m, 1H), 2.3 (m, 2H), 2.5–2.75 (m, 4H), 2.95 (s, 3H), 3.0 (m, 1H), 3.8 (t, 2H), 7.0–7.3 (m, 4H).

MS (thermospray): M/Z [$MH^+$] 341.2; $C_{17}H_{28}N_2O_3S+H$ requires 341.2.

Example 46

(±)-N-((S)-3-Cyclohexyl-3-hydroxypropyl)-4-(3-methanesulfonylaminophenyl)-trans-3,4-dimethylpiperidine To a stirred solution of (+)-4-(3-methanesulfonylaminophenyl)-trans-3,4-dimethylpiperidine (Preparation 10, 100 mg, 0.354 mmol) in dimethoxyethane (30 ml) was added sodium hydrogen carbonate (45 mg, 0.53 mmol) and (S)-3-cyclohexyl-3-hydroxypropyl 4-bromobenzenesulfonate (J. A. Werner et al, J. Org. Chem., 1996, 61, 587), (147 mg, 0.37 mmol). The reaction mixture was heated under reflux for 8 h, then it was concentrated in vacuo. The residue was purified by silica (5 g) column chromatography eluting with methanol:dichloromethane:triethylamine (5:95:0.2) to give the title compound as a yellow oil and as a mixture of diastereomers (143 mg, 95%).

NMR ($CDCl_3$, selected data for the free base): 0.75 (d, 3H), 1.35 (s, 3H), 3.0 (s, 3H), 3.5 (m, 2H), 7.0–7.8 (m, 4H).

MS (APCI): M/Z[$MH^+$] 423.1; $C_{23}H_{38}N_2O_3S+H$ requires 423.3.

Example 47

(±)-N-(4-Cyanobutyl)-4-(3-methanesulfonylaminophenyl)-trans-3,4-dimethylpiperidine To a stirred solution of (±)-4-(3-methanesulfonylaminophenyl)-trans-3,4-dimethylpiperidine (Preparation 10, 100 mg, 0.35 mmol) in N,N-dimethylformamide (2 ml) was added sodium hydrogen carbonate (33 mg, 0.39 mmol) and 5-bromovaleronitrile (45 ml, 0.39 mmol). The stirred reaction mixture was heated under reflux for 45 min, then concentrated in vacuo to give the crude product which was purified by silica (10 g) column chromatography eluting with a gradient of dichloromethane:methanol:0.880 ammonia (300:8:1 to 200:8:1) to give the title compound as a beige oil (101 mg, 79%).

NMR ($CDCl_3$, selected data for the free base): 0.75 (d, 3H), 1.3 (s, 3H), 1.7 (m, 5H), 2.0 (m, 1H), 2.2–2.6 (m, 8H), 2.8 (m, 1H), 3.0 (s, 3H), 7.0–7.35 (m, 4H).

MS (thermospray): M/Z [$MH^+$] 364.2; $C_{19}H_{29}N_3O_2S+H$ requires 364.2.

Example 48

(±)-N-(5-Cyanopentyl)-4-(3-methanesulfonylaminophenyl)-trans-3,4-dimethylpiperidine To a stirred solution of (±)-4-(3-methanesulfonylaminophenyl)-trans-3,4-dimethylpiperidine (Preparation 10, 44 mg, 0.157 mmol) in N,N-dimethylformamide (1.5 ml) was added sodium hydrogen carbonate (26 mg, 0.314 mmol) and 6-bromocapronitrile (23 ml, 0.172 mmol). The stirred reaction mixture was heated under reflux for 3 h, then quenched with water (5 ml) and extracted with dichloromethane (3×10 ml). The organic fractions were washed with saturated brine (10 ml), dried ($Na_2SO_4$), filtered and concentrated in vacuo to give the crude product which was purified by silica (5 g) column chromatography eluting with dichloromethane:methanol:0.880 ammonia (98:2:1) to give the title compound as a clear oil (22 mg, 37%).

NMR ($CDCl_3$, selected data for the free base): 0.75 (d, 3H), 1.3 (s, 3H), 2.0 (m, 1H), 2.2–2.4 (m, 6H), 2.8, (m, 1H), 3.0 (s, 3H), 7.0–7.35 (m, 4H).

MS (thermospray): M/Z [$MH^+$] 378.3; $C_{20}H_{31}N_3O_2S+H$ requires 378.2.

Example 49

(±)-N-(3,3,4,4,5,5,6,6,6-Nonafluorohexyl)-4-(3-methanesulfonylaminophenyl)-trans-3,4-dimethylpiperidine To a stirred solution of (±)-4-(3-methanesulfonylaminophenyl)-trans-3,4-dimethylpiperidine (Preparation 10, 25 mg, 0.088 mmol) in N,N-dimethylformamide (2 ml) was added sodium hydrogen carbonate (11 mg, 0.13 mmol) and 3,3,4,4,5,5,6,6,6-nonafluorohexyl iodide (34.5 mg, 0.092 mmol). The reaction was then heated to 90° C. for 5 h and then left to cool to room temperature and stirred for a further 16 h. The reaction mixture was then diluted with water (50 ml) and extracted with diethyl ether (50 ml). The organic fraction was dried (MgSO$_4$), filtered and concentrated in vacuo. The residue was purified by silica (5 g) column chromatography eluting with ethyl acetate:hexane (4:1) to give the title compound as a clear oil (5 mg, 16%).

NMR (CDCl$_3$, selected data for the free base): 0.8 (d, 3H), 1.3 (s, 3H), 2.6–2.8 (m, 2H), 3.0 (s, 3H), 6.25 (br.s, 1H), 7.0–7.3 (m, 4H).

MS (thermospray): M/Z [MH$^+$] 529.4; C$_{20}$H$_{25}$F$_9$N$_2$O$_2$S+H requires 529.2.

Example 50

(±)-N-(N-Cyclohexylaminocarbonylmethyl)-4-(3-methanesulfonylaminophenyl)-trans-3,4-dimethylpiperidine To a solution of (±)-4-(3-methanesulfonylaminophenyl)-trans-3,4-dimethylpiperidine (Preparation 10, 50 mg, 0.177 mmol) in N,N-dimethylformamide (2 ml) was added sodium hydrogen carbonate (25 mg, 0.3 mmol) and 2-chloro-N-cyclohexylacetamide (31 mg, 0.18 mmol) and the reaction mixture was heated at 80° C. for 3 h. Water (50 ml) was added and the mixture was extracted with ethyl acetate (50 ml). The extract was dried (MgSO$_4$), filtered and concentrated in vacuo to afford the crude product. The residue was purified by silica (5 g) column chromatography eluting with ethyl acetate:hexane (3:1) to afford the title compound.

NMR (CDCl$_3$, selected data for the free base): 0.8 (d, 3H), 1.35 (s, 3H), 2.05 (m, 1H), 2.35 (m, 1H), 2.55 (m, 2H), 3.8 (m, 1H), 7.0–7.35 (m, 4H).

MS (APCI): M/Z [MH$^+$] 422.5; C$_{22}$H$_{35}$N$_2$O$_3$S+H requires 422.2.

Example 51

(±)-N-(2-(N-Cyclohexylamino)ethyl)-4-(3-methanesulfonylaminophenyl)-trans-3,4-dimethylpiperidine To a solution of (±)-N-(N-cyclohexylaminocarbonylmethyl)-4-(3-methanesulfonylaminophenyl)-trans-3,4-dimethylpiperidine (Example 50, 16 mg, 0.04 mmol) in tetrahydrofuran (1 ml) was added lithium aluminium hydride (1.0 M solution in diethyl ether, 0.1 ml, 0.1 mmol) and the mixture was allowed to stand overnight. The reaction was quenched with aqueous Rochelle's salt and the mixture was extracted with ethyl acetate. The combined extracts were washed with brine, dried (MgSO$_4$), filtered and concentrated in vacuo to give the crude product which was purified by silica column chromatography eluting with a gradient of dichloromethane:methanol (100:0 to 0:100) to give the title compound as a gum (6 mg, 39%).

NMR (CDCl$_3$, selected data for the free base): 0.75 (d, 3H), 1.55–1.8 (m, 4H), 1.85 (m, 2H), 2.0 (m, 1H), 3.0 (s, 3H), 7.0–7.35 (m, 4H).

MS (thermospray): M/Z [MH$^+$] 408.3; C$_{22}$H$_{37}$N$_3$O$_2$S+H requires 408.3.

Example 52

(±)-N-(3-Cyclohexyl-3-oxopropyl)-4-(3-methanesulfonylaminophenyl)-trans-3,4-dimethylpiperidine To a solution of (±)-4-(3-methanesulfonylaminophenyl)-trans-3,4-dimethylpiperidine (Preparation 10, 30 mg, 0.11 mmol) in dimethoxyethane (5 ml) was added sodium hydrogen carbonate (17 mg, 0.15 mmol) and 3-cyclohexyl-3-oxopropyl 4-bromobenzenesulfonate (Preparation 31, 40 mg, 0.11 mmol) and the reaction mixture was heated at 100° C. for 24 h. Water (10 ml) was added and the mixture was extracted with ethyl acetate (20 ml). The extract was dried (MgSO$_4$), filtered and concentrated in vacuo to afford the crude product. The residue was purified by silica (5 g) column chromatography eluting with ethyl acetate hexane (2:1) to afford the title compound.

NMR (CDCl$_3$, selected data for the free base) 0.75 (d, 3H), 2.0 (m, 1H), 2.8 (m, 1H), 3.0 (s, 3H), 7.0–7.35 (m, 4H).

MS (APCI): M/Z [MH$^+$] 421.6; C$_{23}$H$_{36}$N$_2$O$_3$S+H requires 421.3.

Example 53

(±)-N-(3-(Ethoxycarbonyl)-3-cyclohexylpropyl)-4-(3-methanesulfonylaminophenyl)-trans-3,4-dimethylpiperidine To a stirred solution of (±)-4-(3-methanesulfonylaminophenyl)-trans-3,4-dimethylpiperidine (Preparation 10, 25 mg, 0.09 mmol) in N,N-dimethylformamide was added sodium hydrogen carbonate (17 mg, 0.2 mmol) and (±) ethyl 4-chloro-2-cyclohexylbutanoate (prepared according to the method described in EP 506478-A1, 23 mg, 0.1 mmol) and the mixture was heated at 90° C. for 3 h. The mixture was allowed to cool to room temperature and diluted with water. The mixture was extracted with ethyl acetate and the combined extracts were washed with brine, dried (MgSO$_4$), filtered and concentrated in vacuo to give the crude product. This was purified by silica column chromatography eluting with ethyl acetate:hexane (1:1) to give a 1:1 mixture of diastereomers of the title compound as a tan gum (7 mg, 16%).

NMR (CDCl$_3$, selected data for the free base): 0.85 (m, 3H), 2.0 (m, 1H), 2.4–2.6 (m, 2H), 2.8 (m, 1H), 3.0 (s, 3H), 4.25 (m, 2H), 7.0–7.35 (m, 4H).

MS (thermospray): M/Z [MH$^+$] 479.2; C$_{26}$H$_{42}$N$_2$O$_4$S+H requires 479.3.

Example 54

(±)-N-(3-Cyclopentylpropyl)-4-(3-methanesulfonylaminophenyl)-trans-3,4-dimethylpiperidine To a stirred solution of (±)-4-(3-methanesulfonylaminophenyl)-trans-3,4-dimethylpiperidine (Preparation 10, 25 mg, 0.088 mmol) in N,N-dimethylformamide (1 ml) was added sodium hydrogen carbonate (11 mg, 0.13 mmol) and 3-cyclopentyl-1-iodopropane (Preparation 12, 21 mg, 0.088 mmol) and the reaction mixture was stirred at room temperature for 2 days. The reaction mixture was diluted with water (50 ml) and extracted with diethyl ether (50 ml). The extract was dried (MgSO$_4$), filtered and concentrated in vacuo to give the crude product. This was purified by silica (5 g) column chromatography eluting with ethyl acetate:hexane (4:1) to give the title compound as a white foam (8 mg, 23%).

NMR (CDCl$_3$, selected data for the free base): 0.8 (d, 3H), 1.3 (s, 3H), 2.5 (dd, 2H), 3.0 (s, 3H), 7.0–7.3 (m, 4H).

MS (thermospray): M/Z [MH$^+$] 393.2; C$_{22}$H$_{36}$N$_2$O$_2$S+H requires 393.3.

Example 55

(±)-N-(3-Cyclohexylpropyl)-4-(3-methanesulfonylaminophenyl)-trans-3,4-dimethylpiperidine To a stirred solution of (±)-4-(3-methanesulfonylaminophenyl)-trans-3,4- dimethylpiperidine (Preparation 10, 100 mg, 0.354 mmol) in N,N-dimethylformamide (3 ml) was added sodium hydrogen carbonate (37 mg, 0.44 mmol) sodium iodide (3 mg, 0.02 mmol) and 1-chloro-3-cyclohexylpropane (63 ml, 0.39 mmol). The reaction mixture was heated under reflux for 1 h, then it was concentrated in vacuo. The residue was purified by silica (5 g) column chromatography eluting with methanol:dichloromethane:triethylamine (5:95:0.2) to give the title compound as a yellow oil (57 mg, 40%).

NMR (CDCl$_3$, selected data for the free base): 0.85 (d, 3H), 1.05–1.35 (m, 11H), 1.45 (s, 3H), 3.0 (s, 3H), 7.0–7.4 (m, 4H).

MS (APCI): M/Z [MH$^+$] 407.6; $C_{23}H_{38}N_2O_2S+H$ requires 407.3.

Example 56

(±)-N-4-(3-Methanesulfonylaminophenyl)-trans-3,4-dimethyl-(3-(4,4-dimethylcyclohexyl)propyl)piperidine To a solution of (±)-4-(3-methanesulfonylaminophenyl)-trans-3,4-dimethylpiperidine (Preparation 10, 50 mg, 0.176 mmol) in N,N-dimethylformamide (4 ml) was added sodium hydrogen carbonate (23 mg, 0.27 mmol) and 1-iodo-2-(4,4-dimethylcyclohexyl)ethane (Preparation 17, 53 mg, 0.19 mmol) respectively. The stirred reaction mixture was heated at 80° C. for 24 h, then quenched with water (10 ml) and extracted with ethyl acetate (10, 5 ml). The combined extracts were concentrated by a steady stream of nitrogen gas over a hot plate at 50° C. to give the crude product. The residue was purified by preparative HPLC on a Phenomenex Magellan™ column, 15 cm×2.1 cm; flow 10.0 ml min$^{-1}$; employing UV detection at 230 nm; eluant gradient of acetonitrile:0.1M aqueous ammonium acetate solution (50:50 to 95:5) to afford the title compound as its acetate salt.

NMR (CDCl$_3$, selected data for the acetate salt): 0.8–0.9 (m, 9H), 1.35 (s, 3H), 1.75 (m, 1H), 2.0 (s, 3H), 2.4 (m, 1H), 3.0 (s, 3H), 3.1 (m, 1H), 7.05–7.3 (m, 4H).

MS (APCI): M/Z [MH$^+$] 421.1; $C_{24}H_{40}N_2O_2S+H$ requires 421.3.

Example 57

(±)-N-(2-Cyclohexyloxyethyl)-4-(3-methanesulfonylaminophenyl)-trans-3,4-dimethylpiperidine To a stirred solution of (±)-4-(3-methanesulfonylaminophenyl)-trans-3,4-dimethylpiperidine (Preparation 10, 25 mg, 0.088 mmol) in N,N-dimethylformamide (2 ml) was added sodium hydrogen carbonate (11 mg, 0.13 mmol) and 2-cyclohexyloxy-1-iodoethane (Preparation 19, 20 mg, 0.11 mmol). The reaction mixture was heated to 90° C. for 2 h and then cooled to room temperature. The reaction mixture was diluted with water (40 ml) and extracted with ether (2×20 ml). The combined extracts were dried (MgSO$_4$), filtered and concentrated in vacuo to give the crude product. This was purified by silica (5 g) column chromatography eluting with ethyl acetate:hexane (4:1) to give the title compound as a light brown gum (6 mg, 16%).

NMR (CDCl$_3$, selected data for the free base): 0.75 (d, 3H), 1.35 (s, 3H), 3.0 (s, 3H), 3.6 (t, 2H), 7.0–7.4 (m, 4H).

MS (APCI): M/Z [MH$^+$] 409.3; $C_{22}H_{36}N_2O_3S+H$ requires 409.3.

Example 58

(±)-4-(3-Methanesulfonylaminophenyl)-trans-3,4-dimethyl-N-(2-phenylethyl)piperidine To a solution of (±)-4-(3-methanesulfonylaminophenyl)-trans-3,4-dimethylpiperidine (Preparation 10, 25 mg, 0.088 mmol) in N,N-dimethylformamide (5 ml) was added sodium hydrogen carbonate (11 mg, 0.135 mmol) and 1-(2-bromoethyl)benzene (14.7 mg, 0.08 mmol), and the reaction mixture was heated at 100° C. for 24 h. Water (10 ml) was added and the mixture was extracted with ethyl acetate (3×5 ml). The combined extracts were dried (MgSO$_4$), filtered and concentrated in vacuo to give the crude product. This was purified by silica (10 g) column chromatography eluting with ethyl acetate:hexane (1:1) to give the title compound.

NMR (CDCl$_3$, selected data for the free base): 0.8 (d, 3H), 1.35 (s, 3H), 1.6 (m, 2H), 2.05 (m, 1H), 3.0 (s, 3H), 3.6 (t, 2H), 7.0–7.35 (m, 9H).

MS (APCI): M/Z [MH$^{30}$ ] 387.5; $C_{22}H_{30}N_2O_2S+H$ requires 387.2.

Example 59

(±)-4-(3-Methanesulfonylaminophenyl)-trans-3,4-dimethyl-N-(3-phenylpropyl)piperidine To a stirred solution of (±)-4-(3-methanesulfonylaminophenyl)-trans-3,4-dimethylpiperidine (Preparation 10, 26 mg, 0.092 mmol) in N,N-dimethylformamide (2 ml) was added sodium hydrogen carbonate (12 mg, 0.15 mmol) and 1-bromo-3-phenylpropane (19 mg, 0.1 mmol). The stirred reaction mixture was heated at 100° C. for 4 h, then quenched with water (50 ml) and extracted with diethyl ether (50 ml). The organic fraction was dried (MgSO$_4$), filtered and concentrated in vacuo to give the crude product which was purified by silica (5 g) column chromatography, eluting with ethyl acetate:hexane (4:1), to give the title compound as a clear oil (8 mg, 22%).

NMR (CDCl$_3$, selected data for the free base): 0.8 (d, 3H), 1.3 (s, 3H), 2.0 (m, 1H), 2.8 (m, 1H), 3.0 (s, 3H), 7.0–7.4 (m, 9H).

MS (thermospray): M/Z [MH$^+$] 401.4; $C_{23}H_{32}N_2O_2S+H$ requires 401.2.

Example 60

(±)-N-(2-Cycloheyxlideneethyl)-4-(3-methanesulfonylaminophenyl)-trans-3,4-dimethylpiperidine To a solution of (±)-4-(3-methanesulfonylaminophenyl)-trans-3,4-dimethylpiperidine (Preparation 10, 350 mg, 1.24 mmol) in N,N-dimethylformamide (10 ml) was added sodium hydrogen carbonate (156 mg, 1.86 mmol) and 2-cycloheyxlideneethyl bromide (M. Ohki et al, Agr. Biol. Chem., 1972, 36, 979) (235 mg, 1.24 mmol). The stirred reaction mixture was heated at 60° C. for overnight, then it was concentrated in vacuo. Water (20 ml) was added, and the mixture was extracted with ethyl acetate (2×25 ml). The combined extracts were dried (MgSO$_4$), filtered and concentrated in vacuo to give the crude product which was purified by silica (10 g) column chromatography, eluting with a gradient of ethyl acetate:hexane (0:100 to 100:0), to give the title compound as a clear oil (55 mg, 11%). The oil was dissolved in dry diethyl ether (10 ml) and 1.1 mol equivalents of 1N ethereal hydrogen chloride solution was added to provide a precipitate which was collected by filtration and dried in a vacuum oven to yield the title compound as a white hygroscopic solid (32 mg).

NMR (CD$_3$OD selected data for the hydrochloride salt): 0.8 (br. s, 3H), 1.45 (s, 3H), 1.55–1.75 (m, 4H), 2.35–2.45 (m, 4H), 2.95 (s, 3H), 5.6 (br. s, 1H), 7.05–7.4 (m, 4H).

MS (thermospray): M/Z [MH$^+$] 391.4; C$_{22}$H$_{34}$N$_2$O$_2$S+H requires 391.2.

Example 61

(±)-4-(3-Methanesulfonylaminophenyl)-trans-3,4-dimethyl-N-(3,3-diphenylpropyl)piperidine To a solution of (±)-4-(3-methanesulfonylaminophenyl)-trans-3,4-dimethylpiperidine (Preparation 10, 350 mg, 1.24 mmol) in N,N-dimethylformamide (10 ml) was added sodium hydrogen carbonate (156 mg, 1.86 mmol) and 3,3-diphenylpropyl bromide (341 mg, 1.24 mmol). The stirred reaction mixture was heated at 60° C. for overnight, then it was concentrated in vacuo. Water (20 ml) was added, and the mixture was extracted with ethyl acetate (2×25 ml). The combined extracts were dried (MgSO$_4$), filtered and concentrated in vacuo to give the crude product which was purified by silica (15 g) column chromatography, eluting with a gradient of ethyl acetate:hexane (0:100 to 100:0) to give the title compound as a clear oil (300 mg, 51%). The oil was dissolved in dry diethyl ether (25 ml) and 1.1 mol equivalents of 1N ethereal hydrogen chloride solution was added to provide a precipitate which was collected by filtration and dried in a vacuum oven to yield the title compound as a white hygroscopic solid (257 mg).

NMR (CD$_3$OD, selected data for the hydrochloride salt): 0.9 (d, 3H), 1.25 (s, 3H), 1.95 (m, 1H), 2.9 (s, 3H), 4.05 (m, 1H), 7.05–7.4 (m, 14H).

MS (thermospray): M/Z [MH$^+$] 477.3; C$_{29}$H$_{36}$N$_2$O$_2$S+H requires 477.2.

Example 62

(±)-4-(3-Methanesulfonylaminophenyl)-trans-3,4-dimethyl-N-(3-(2-methylphenyl)propyl)piperidine To a solution of (±)-4-(3-methanesulfonylaminophenyl)-trans-3,4-dimethylpiperidine (Preparation 10, 50 mg, 0.177 mmol) in N,N-dimethylformamide (5 ml) was added sodium hydrogen carbonate (25 mg, 0.3 mmol) and 1-(3-iodopropyl)-2-methylbenzene (prepared according to the method described in EP 279681 A2), (46 mg, 0.177 mmol) and the reaction mixture was heated at 80° C. for 3 h. Water (50 ml) was added and the mixture was extracted with ethyl acetate (50 ml). The organic fraction was dried (MgSO$_4$), filtered and concentrated in vacuo to give the crude product which was purified by silica (5 g) column chromatography, eluting with ethyl acetate:hexane (2:1), to afford the title compound as the free base. The oil was dissolved in dry diethyl ether (2 ml) and 1.1 mol equivalents of 1N ethereal hydrogen chloride solution was added. The suspension was concentrated in vacuo to afford title compound as a white hygroscopic solid (14 mg, 19%).

NMR (CDCl$_3$, selected data for the free base): 0.8 (d, 3H), 1.35 (s, 3H), 2.3 (s, 3H), 3.0 (s, 3H), 7.05–7.4 (m, 8H).

MS (APCI): M/Z [MH$^+$] 415.1; C$_{24}$H$_{34}$N$_2$O$_2$S+H requires 415.2.

Example 63

(±)-4-(3-Methanesulfonylaminophenyl)-trans-3,4-dimethyl-N-(1-(4-ethylphenyl)methyl)piperidine To a solution of (±)-4-(3-methanesulfonylaminophenyl)-trans-3,4-dimethylpiperidine (Preparation 10, 50 mg, 0.177 mmol) in N,N-dimethylformamide (2 ml) was added sodium hydrogen carbonate (25 mg, 0.3 mmol) and 1-(chloromethyl)-4-ethylbenzene (28 mg, 0.18 mmol). The reaction mixture was heated at 80° C. for 4 h, and then stirred at room temperature for 48 h. Water (100 ml) was added and the mixture was extracted with ethyl acetate (100 ml). The extract was dried (MgSO$_4$), filtered and concentrated in vacuo to afford the crude product. The residue was purified by silica (5 g) column chromatography eluting with ethyl acetate:hexane (1:1) to afford the title compound as a pale yellow oil (34 mg, 45%).

NMR (CDCl$_3$, selected data for the free base): 0.75 (d, 3H), 1.15 (t, 3H), 1.3 (s, 3H), 2.65 (q, 2H), 3.0 (s, 3H), 3.5 (m, 2H), 7.05–7.4 (m, 8H).

MS (APCI): M/Z [MH$^+$] 401.1; C$_{23}$H$_{32}$N$_2$O$_2$S+H requires 401.2.

Example 64

(±)-N-(2-(3-Ethylphenyl)ethyl)-4-(3-methanesulfonylaminophenyl)-trans-3,4-dimethylpiperidine To a solution of (±)-4-(3-methanesulfonylaminophenyl)-trans-3,4-dimethyipiperidine (Preparation 10, 50 mg, 0.177 mmol) in N,N-dimethylformamide (2 ml) was added sodium hydrogen carbonate (30 mg, 0.354 mmol) and 1-(2-bromoethyl)-3-ethylbenzene (Preparation 21, 40 mg, 0.186 mmol) and the reaction mixture was heated at 80° C. for 5 h. The mixture was concentrated in vacuo, and the residue was dissolved in dichloromethane (10 ml), filtered and concentrated in vacuo to afford the crude product. The residue was purified by silica (5 g) column chromatography eluting with a gradient of ethyl acetate:hexane (2:98 to 100:0) to afford the title compound as a colourless oil (19 mg, 25%).

NMR (CDCl$_3$, selected data for the free base): 0.8 (d, 3H), 1.2–1.3 (m, 6H), 1.35 (s, 3H), 1.6 (m, 2H), 2.0–2.05 (m, 3H), 3.0 (s, 3H), 4.05 (q, 2H), 7.0–7.35 (m, 8H).

MS (APCI): M/Z [MH$^+$] 415.2; C$_{24}$H$_{34}$N$_2$O$_2$S+H requires 415.2.

Example 65

(±)-4-(3-Methanesulfonylaminophenyl)-N-(2-(3-methoxyphenyl)-ethyl)-trans-3,4-dimethylpiperidine To a solution of (±)-4-(3-methanesulfonylaminophenyl)-trans-3,4-dimethylpiperidine (Preparation 10, 50 mg, 0.088 mmol) in N,N-dimethylformamide (2 ml) was added sodium hydrogen carbonate (23 mg, 0.27 mmol) and 3-methoxyphenethyl 4-bromobenzenesulfonate (Preparation 22, 59 mg, 0.16 mmol) and the reaction mixture was heated at 100° C. for 4 h. Water (10 ml) was added and the mixture was extracted with ethyl acetate (3×5 ml). The combined extracts were dried (MgSO$_4$), filtered and concentrated in vacuo to afford the crude product. The residue was purified by silica (10 g) column chromatography eluting with ethyl acetate:hexane (1:1) to afford the title compound as a pale yellow oil (7 mg, 10%).

NMR (CDCl$_3$, selected data for the free base): 0.8 (d, 3H), 1.3 (s, 3H), 3.0 (s, 3H), 3.8 (s, 3H), 6.7–6.9 (m, 3H), 7.05–7.35 (m, 5H).

MS (APCI): M/Z [MH$^+$] 417.3; C$_{23}$H$_{32}$N$_2$O$_3$S+H requires 417.2.

Example 66

(±)-4-(3-Methanesulfonylaminophenyl)-trans-3,4-dimethyl-N-(2-(3-trifluoromethylphenyl)ethyl) piperidine To a solution of (±)-4-(3-methanesulfonylaminophenyl)-trans-3,4-dimethylpiperidine (Preparation 10, 80 mg, 0.28 mmol) in N,N-dimethylformamide (2 ml) was added sodium hydrogen carbonate (35 mg, 0.42 mmol) and 3-(trifluoromethyl)phenethyl 4-bromobenzenesulfonate (Preparation 23, 80 mg, 0.19 mmol) and the reaction mixture was heated at 100° C. for 4 h. Water (10 ml) was added and the mixture was extracted with ethyl acetate (3×5 ml). The combined extracts were dried (MgSO$_4$), filtered and concentrated in vacuo to afford the crude product. The residue was purified by silica (10 g) column chromatography eluting with ethyl acetate:hexane (1:1) to afford the title compound as a pale yellow oil (17 mg, 14%).

NMR (CDCl$_3$, selected data for the free base): 0.8 (d, 3H), 1.35 (s, 3H), 3.0 (s, 3H), 7.05–7.5 (m, 8H).

MS (APCI): M/Z [MH$^+$] 445.3; $C_{23}H_{30}F_3N_2O_2S$+H requires 455.2.

Example 67

(±)-4-(3-Methanesulfonylaminophenyl)-trans-3,4-dimethyl-N-(1-naphthylethyl)piperidine To a solution of (±)-4-(3-methanesulfonylaminophenyl)-trans-3,4-dimethylpiperidine (Preparation 10, 30 mg, 0.11 mmol) in N,N-dimethylformamide (2 ml) was added sodium hydrogen carbonate (14 mg, 0.17 mmol) and 1-naphthylethyl 4-bromobenzenesulfonate (Preparation 24, 41 mg, 0.11 mmol) and the reaction mixture was heated at 80° C. for 18 h. Water (10 ml) was added and the mixture was extracted with ethyl acetate (3×5 ml). The combined extracts were dried (MgSO$_4$), filtered and concentrated in vacuo to afford the crude product. The residue was purified by silica (10 g) column chromatography eluting with ethyl acetate:hexane (1:1) to afford the title compound as a pale yellow oil (5 mg, 1:1%).

NMR (CDCl$_3$, selected data for the free base): 0.8 (d, 3H), 1.35 (s, 3H), 3.0 (s, 3H), 3.25 (m, 2H), 7.05–7.6 (m, 8H), 7.7–8.1 (m, 3H).

MS (thermospray): M/Z [MH$^+$] 437.3; $C_{26}H_{32}N_2O_2S$+H requires 437.2.

Example 68

(±)-4-(3-Methanesulfonylaminophenyl)-trans-3,4-dimethyl-N-(2-phenoxyethyl)piperidine To a solution of (±)-4-(3-methanesulfonylaminophenyl)-trans-3,4-dimethylpiperidine (Preparation 10, 100 mg, 0.354 mmol) in N,N-dimethylformamide (3 ml) was added sodium hydrogen carbonate (60 mg, 0.71 mmol) and 2-phenoxyethyl bromide (75 mg, 0.37 mmol). The reaction mixture was heated under reflux for 3 h and then it was concentrated in vacuo. The residue was purified by silica (5 g) column chromatography eluting with methanol:dichloromethane:triethylamine (5:95:0.2) to give the title compound as a yellow oil (118 mg, 83%).

NMR (CDCl$_3$, selected data for the free base): 0.8 (d, 3H), 1.3 (s, 3H), 2.0 (m, 1H), 3.0 (s, 3H), 4.05 (m, 2H), 6.8–7.4 (m, 9H).

MS (APCI): M/Z[MH$^+$] 403.1; $C_{22}H_{30}N_2O_3S$+H requires 403.2.

Example 69

(±)-N-(2-(2,6-Dichlorophenoxy)ethyl)-4-(3-(N-(2-(2,6-dichlorophenoxy)ethyl)-methanesulfonylamino)phenyl)-trans-3,4-dimethylpiperidine To a solution of (±)-4-(3-methanesulfonylaminophenyl)-trans-3,4-dimethylpiperidine (Preparation 10, 50 mg, 0.176 mmol) in N,N-dimethylformamide (3 ml) was added sodium hydrogen carbonate (30 mg, 0.357 mmol) and 1-bromoethyl-2,6-dichlorobenzene (prepared by the method described in U.S. Pat. No. 3,474,134) (77 mg, 0.2 mmol), and the reaction mixture was heated at 100° C. for 16 h. Water (10 ml) was added and the mixture was extracted with ethyl acetate (2×10 ml). The combined extracts were dried (MgSO$_4$), filtered and concentrated by a steady stream of nitrogen gas over a hot plate at 50° C. to afford the crude product. The residue was purified by silica (10 g) column chromatography eluting with dichloromethane:methanol (30:1) to afford the title compound as a colourless oil (8 mg, 10%).

NMR (CDCl$_3$, selected data for the free base): 0.75 (d, 3H), 1.6 (m, 2H), 2.0 (m, 1H), 2.35 (m, 1H), 2.55 (m, 1H), 3.05 (s, 3H), 4.1–4.2 (m, 4H), 6.95 (m, 1H), 7.2–7.4 (m, 5H).

MS (thermospray): M/Z[MH$^+$] 659.2; $C_{30}H_{34}C_{14}N_2O_4S$+H requires 659.1.

Example 70

(±)-N-(2-(2,6-Dichlorophenoxy)ethyl)-4-(3-methanesulfonylaminophenyl)-trans-3,4-dimethylpiperidine Further elution as described in Example 69 provided the title compound as a colourless oil (10 mg, 12%).

NMR (CDCl$_3$, selected data for the free base): 0.75 (d, 3H), 1.35 (m, 3H), 1.6 (m, 2H), 2.0 (m, 1H), 2.35 (m, 1H), 2.55 (m, 1H), 3.0 (s, 3H), 4.1–4.2 (m, 2H), 7.0–7.3 (m, 3H).

MS (thermospray): M/Z[MH$^+$] 471.0; $C_{22}H_{29}C_{12}N_2O_3S$+H requires 471.1.

Example 71

(±)-4-(3-Methanesulfonylaminophenyl)-trans-3,4-dimethyl-N-(3-(1-tetrazolyl)propyl)piperidine A stirred mixture of (±)-N-(3-hydroxypropyl)-4-(3-methanesulfonylaminophenyl)-trans-3,4-dimethylpiperidine (Example 45, 393 mg, 1.15 mmol) and 1H-tetrazole (81 mg, 1.16 mmol) in dry dichloromethane (4 ml) was cooled in an ice bath and treated with triphenylphosphine (304 mg, 1.16 mmol) followed by diethyl azodicarboxylate (0.18 ml, 1.16 mmol) dropwise. The resultant mixture was allowed to warm to room temperature and stirred over the weekend. The solvent was removed in vacuo to give a foam which was purified by silica (50 g) column chromatography, eluting with dichloromethane:ethanol:0.880 ammonia (300:8:1) to give the title compound as an opaque oil (160 mg, 35%).

NMR (CDCl$_3$, selected data for the free base): 0.75 (d, 3H), 1.35 (s, 3H), 1.6 (m, 1H), 2.0 (m, 1H), 2.1–2.5 (m, 6H), 2.55 (m, 2H), 2.8 (m, 1H), 3.0 (s, 3H), 4.75 (t, 2H), 6.45 (br. s, 1H), 7.0–7.35 (m, 4H), 8.5 (s, 1H).

MS (thermospray): M/Z [MH$^+$] 393.5; $C_{18}H_{28}N_6O_2S$+H requires 393.2.

Example 72

(±)-4-(3-Methanesulfonylaminophenyl)-trans-3,4-dimethyl-N-(3-(tetrahydropyran-2-yl)propyl)piperidine A solution of (±)-4-(3-methanesulfonylaminophenyl)-trans-3,4-dimethyl-N-(3-(tetrahydropyran-2-yl)propanoyl)piperidine (Preparation 27, 156 mg, 0.37 mmol) in anhydrous tetrahydrofuran (2 ml) under nitrogen was treated dropwise with lithium aluminium hydride (1.0 M solution in diethyl ether, 0.74 ml, 0.74 mmol). The reaction mixture was stirred overnight, diluted with ammonium chloride solution (10 ml) and extracted with ethyl acetate (4×10 ml). The combined extracts were dried ($Na_2SO_4$) and concentrated in vacuo to give a clear oil which was purified by silica (7 g) column chromatography eluting with dichloromethane:ethanol:0.880 ammonia (200:8:1) to give the title compound as a diastereomeric mixture (96 mg, 63%).

NMR ($CDCl_3$, selected data for the free base): 0.8 (d, 3H), 1.25 (m, 2H), 1.3 (s, 3H), 1.35–1.9 (m, 9H), 2.0 (m, 1H), 2.2–2.9 (m, 7H), 3.0 (s, 3H), 3.2–4.0 (m, 4H), 7.0–7.35 (m, 4H).

MS (thermospray): M/Z [$MH^+$] 409.0; $C_{22}H_{36}N_2O_3S$+H requires 409.3.

Example 73

(±)-N-(2-(1,3-Dioxan-2-yl)ethyl)-4-(3-methanesulfonylamino-phenyl)-trans-3,4-dimethylpiperidine To a stirred solution of (±)-4-(3-methanesulfonylaminophenyl)-trans-3,4-dimethylpiperidine (Preparation 10, 53 mg, 0.187 mmol) in N,N-dimethylformamide (2 ml) was added sodium hydrogen carbonate (32 mg, 0.374 mmol) and 2-(2-bromoethyl)-1,3-dioxan (27 ml, 0.196 mmol). The stirred reaction mixture was heated under reflux for 1 h 30 min, then quenched with water (10 ml) and extracted with dichloromethane (3×15 ml). The organic fractions were washed with saturated brine (10 ml), dried ($Na_2SO_4$), filtered and concentrated in vacuo to give the crude product which was purified by silica (5 g) column chromatography, eluting with dichloromethane:methanol:0.880 ammonia (95:5:1) to give the title compound as a clear oil (59 mg, 79%). The oil was dissolved in dry ether (2 ml) and 1.1 mol equivalents of 1N ethereal hydrogen chloride solution was added to provide a precipitate which was collected by filtration and dried in a vacuum oven to yield the title compound as a hygroscopic solid.

NMR ($CDCl_3$, selected data for the hydrochloride salt): 0.95 (d, 3H), 3.0 (s, 3H), 3.7 (m, 2H), 4.1 (m, 2H), 7.0–7.3 (m, 4H), 10.8 and 11.9 (2×bs, 1H).

MS (thermospray): M/Z [$MH^+$] 397.3; $C_{20}H_{32}N_2O_4S$+H requires 397.2.

Example 74

(±)-N-(2-(1-Adamantyl)ethyl)-4-(3-methanesulfonylaminophenyl)-trans-3,4-dimethylpiperidine To a stirred solution of (±)-4-(3-methanesulfonylaminophenyl)-trans-3,4-dimethylpiperidine (Preparation 10, 25 mg, 0.088 mmol) in N,N-dimethylformamide (2 ml) was added sodium hydrogen carbonate (11 mg, 0.13 mmol) and 1-adamantane-2-iodoethane (Preparation 29, 36 mg, 0.09 mmol). The reaction mixture was heated to 85° C. for 2 h and then cooled to room temperature. The reaction mixture was diluted with water (40 ml) and extracted with ether (2×20 ml). The combined extracts were dried ($MgSO_4$) and concentrated in vacuo to give the crude product. This was purified by silica (5 g) column chromatography eluting with ethyl acetate:hexane (4:1) to give the title compound as a light brown gum (6 mg, 15%).

NMR ($CDCl_3$, selected data for the free base): 0.8 (d, 3H), 1.35 (s, 3H), 2.55 (m, 2H), 3.0 (s, 3H), 7.0–7.4 (4H, m).

MS (thermospray): M/Z [$MH^+$] 445.3; $C_{26}H_{40}N_2O_2S$+H requires 445.3.

Example 75

(±)-4-(3-Methanesulfonylaminophenyl)-trans-3,4-dimethyl-N-[(E)-6,6-dimethyl-2-hepten-4-ynyl] piperidine To a solution of (±)-4-(3-methanesulfonylaminophenyl)-trans-3,4-dimethylpiperidine (Preparation 10, 50 mg, 0.176 mmol) in N,N-dimethylformamide (3 ml) was added sodium hydrogen carbonate (30 mg, 0.357 mmol) and a 3:1 mixture E:Z isomers 1-bromo-6,6-dimethyl-2-heptene-4-yne (A. St ütz and G. Petranyi, J. Med. Chem., 1984, 27, 1539) (63 mg, 0.2 mmol), and the stirred reaction mixture was heated at 100° C. for 16 h. Water (10 ml) was added and the mixture was extracted with ethyl acetate (2×10 ml). The combined extracts were dried ($MgSO_4$), filtered and concentrated by a steady stream of nitrogen gas over a hot plate at 50° C. to afford the crude product. The residue was purified by preparative HPLC on a Phenomenex Magellan™ column, 15 cm×2.1 cm; flow 10.0 ml min$^{-1}$; employing U.V. detection at 230 nm; eluant gradient of acetonitrile:0.1M aqueous ammonium acetate solution (50:50 to 95:5). Fractions were analysed by LCMS, combined and evaporated by a steady stream of nitrogen gas over a hot plate at 50° C. to afford the title compound as its acetate as a pale yellow solid (7 mg, 10%).

NMR ($CDCl_3$, selected data for the acetate salt): 0.8 (d, 3H), 1.25 (s, 9H), 1.35 (s, 3H), 1.7 (m, 1H), 2.4 (m, 1H), 3.0 (s, 3H), 3.4 (d, 2H), 5.65 (m, 1H), 5.95 (m, 1H), 7.0–7.35 (m, 4H).

MS (electrospray): M/Z [$MH^+$] 403.2; $C_{23}H_{34}N_2O_2S$+H requires 403.2.

Example 76

(±)-4-(3-Methanesulfonylaminophenyl)-trans-3,4-dimethyl-N-[(Z)-6,6-dimethyl-2-hepten-4-ynyl] piperidine Further elution and concentration of the appropriate fractions as described in Example 75 provided the title compound as its acetate salt as a pale yellow solid (2 mg, 3%).

NMR ($CDCl_3$, selected data for the acetate salt): 0.8 (d, 3H), 1.25 (s, 9H), 1.35 (s, 3H), 1.65 (m, 1H), 3.0 (s, 3H), 5.65 (m, 1H), 6.05 (m, 1H), 7.0–7.35 (m, 4H).

MS (electrospray): M/Z [$MH^+$] 403.2; $C_{23}H_{34}N_2O_2S$+H requires 403.2.

Example 77

(±)-N-((E)-3-Cyclohexylprop-2-enyl)-4-(3-methanesulfonylaminophenyl)-trans-3,4-dimethylpiperidine To a stirred solution of (±)-4-(3-methanesulfonylaminophenyl)-trans-3,4-dimethylpiperidine (Preparation 10, 25 mg, 0.088 mmol) in N,N-dimethylformamide (2 ml) was added sodium hydrogen carbonate (11 mg, 0.13 mmol) and (E)-1-bromo-3-cyclohexylprop-2-ene (Preparation 30, 20 mg, 0.10 mmol). The reaction mixture was heated to 70° C. for 3 h and then cooled to room temperature. The reaction mixture was diluted with water (50 ml) and extracted with ether (3×20 ml). The combined extracts were dried ($MgSO_4$), filtered and concentrated in vacuo to give the crude product. This was purified by silica (5 g) column chromatography eluting with ethyl acetate:hexane (4:1) to give the title compound as a light brown gum (7 mg, 20%).

NMR (CDCl$_3$, selected data for the free base): 0.8 (d, 3H), 1.3 (s, 3H), 2.7–2.95 (m, 2H), 3.0 (s, 3H), 5.35–5.6 (m, 2H), 7.15–7.3 (m, 4H).

MS (thermospray): M/Z [MH$^+$] 405.4; $C_{23}H_{36}N_2O_2S$+H requires 405.3.

Example 78

(±)-N-Cinnamyl-4-(3-(N-cinnamyl-methanesulfonylamino)phenyl)-trans-3,4-dimethylpiperidine To a stirred solution of (±)-4-(3-methanesulfonylaminophenyl)-trans-3,4-dimethylpiperidine (Preparation 10, 25 mg, 0.088 mmol) in N,N-dimethylformamide (1 ml) was added sodium hydrogen carbonate (17 mg, 0.20 mmol) and cinnamyl bromide (20 mg, 0.10 mmol). The reaction mixture was heated under reflux for 20 min, then it was diluted with saturated aqueous ammonium chloride solution (20 ml) and extracted with ethyl acetate (2×20 ml). The combined extracts were dried (MgSO$_4$), filtered and concentrated in vacuo. The residue was purified by silica (5 g) column chromatography using a gradient elution of methanol:dichloromethane (2:98 to 6:94) to give the title compound as a tan gum (13 mg, 37%).

NMR (CDCl$_3$, selected data for the free base): 0.8 (d, 3H), 1.35 (s, 3H), 1.65 (m, 1H), 2.0 (m, 1H), 2.2–2.5 (m, 2H), 2.55–2.7 (m, 2H), 2.9 (m, 1H), 3.0 (s, 3H), 3.15 (dd, 1H), 3.2 (dd, 1H), 6.3 (m, 1H), 6.55 (d, 1H), 7.0–7.4 (m, 9H).

MS (APCI): M/Z [MH$^+$] 399.4; $C_{23}H_{30}N_2O_2S$+H requires 399.2.

Example 79

(±)-N-Cinnamyl-4-(3-methanesulfonylaminophenyl)-trans-3,4-dimethylpiperidine

Further elution as described in Example 78 provided the title compound as a tan gum (14 mg, 29%).

NMR (CDCl$_3$, selected data for the free base): 0.8 (d, 3H), 1.35 (s, 3H), 1.65 (m, 1H), 2.0 (m, 1H), 2.2-2.5 (m, 2H), 2.5-2.65 (m, 2H), 2.85-3.0 (m, 4H), 3.0-3.3 (m, 2H), 4.4 (d, 2H), 6.2 (m, 2H), 6.4 (d, 1H), 6.5 (d, 1H), 7.0-7.4 (m, 14H).

MS (APCI): M/Z [MH$^+$] 515.6; $C_{32}H_{38}N_2O_2S$+H requires 515.3.

Example 80

(±)-N-(2-Hexynyl)-4-(3-methanesulfonylaminophenyl)-3,4-trans-dimethylpiperidine

To a stirred solution of (±)-4-(3-methanesulfonylaminophenyl)-trans-3,4-dimethylpiperidine (Preparation 10, 25 mg, 0.088 mmol) in N,N-dimethylformamide (2 ml) was added sodium hydrogen carbonate (11 mg, 0.13 mmol) and 1-bromo-2-hexyne (16 mg, 0.10 mmol). The reaction mixture was heated to 70° C. for 3 h and then cooled to room temperature. The mixture was diluted with water (10 ml) and extracted with diethyl ether (3×10 ml). The combined extracts were dried (MgSO$_4$), filtered and concentrated in vacuo to give the crude product. This was purified by silica (5 g) column chromatography eluting with ethyl acetate:hexane (4:1) to give the title compound as a light brown gum (5 mg, 16%).

NMR (CDCl$_3$, selected data for the free base): 0.8 (d, 3H), 1.35 (s, 3H), 3.0 (s, 3H), 3.3 (s, 2H), 7.0-7.4 (m, 4H).

MS (thermospray): M/Z [MH$^+$] 363.3; $C_{20}H_{30}N_2O_2S$+H requires 363.2.

Example 81

(±)-4-(3-Methanesulfonylaminophenyl)-trans-3,4-dimethyl-N-(3-phenylprop-2-ynyl)piperidine To a stirred solution of (±)-4-(3-methanesulfonylaminophenyl)-trans-3,4-dimethylpiperidine (Preparation 10, 25 mg, 0.088 mmol) in N,N-dimethylformamide (2 ml) was added sodium hydrogen carbonate (11 mg, 0.13 mmol) and 1-bromo-3-phenyl-2-propyne (P. Place, C. Vernière and J. Goré, Tetrahedron, 1981, 37, 1359) (19 mg, 0.10 mmol). The reaction was then heated to 100° C. for 4 h and then cooled to room temperature. The reaction mixture was diluted with water (50 ml) and extracted with diethyl ether (50 ml). The extract was dried (MgSO$_4$), filtered and concentrated in vacuo. The residue was purified by silica (5 g) column chromatography eluting with ethyl acetate:hexane (4:1) to give the title compound as a colourless gum (9 mg, 26%).

NMR (CDCl$_3$, selected data for the free base): 0.8 (d, 3H), 1.3 (s, 3H), 2.65 (m, 2H), 3.0 (s, 3H), 3.6 (s, 2H), 6.6 (br.s, 1H), 7.0–7.5(m, 9H).

MS (thermospray): M/Z [MH$^+$] 397.0; $C_{23}H_{28}N_2O_2S$+H requires 397.2.

Examples 82–141 (see Table)

The following N-alkyl (±)-4-(3-methanesulfonylaminophenyl)-trans-3,4-dimethyl piperidines were prepared by employing one each of the following methods for synthesis and purification. In each case, the alkyl bromide employed was either commercially available or prepared via the specific literature preparation referenced at the end of the table unless otherwise stated.

Synthetic Method A

To a solution of (±)-4-(3-methanesulfonylaminophenyl)-trans-3,4-dimethylpiperidine (Preparation 10, 50 mg, 0.176 mmol) in N,N-dimethylformamide (3 ml) was added sodium hydrogen carbonate (30 mg, 0.357 mmol) and the appropriate alkyl bromide (0.2 mmol), and the reaction mixture was heated at 100° C. for 16 h. Water (10 ml) was added and the mixture was extracted with ethyl acetate (2×10 ml). The combined extracts were dried (MgSO$_4$), filtered and concentrated by a steady stream of nitrogen gas over a hot plate at 50° C. to give the crude product.

Synthetic Method B

To a solution of (±)-4-(3-methanesulfonylaminophenyl)-trans-3,4-dimethylpiperidine (Preparation 10, 50 mg, 0.176 mmol) in N,N-dimethylformamide (4 ml) was added sodium hydrogen carbonate (23 mg, 0.27 mmol) and the appropriate alkyl bromide (0.19 mmol), and the reaction mixture was heated at 100° C. for 24 h. Water (10 ml) was added and the mixture was extracted with ethyl acetate (3×10 ml). The combined extracts were washed with water (10 ml), dried (MgSO$_4$), filtered and concentrated by a steady stream of nitrogen gas over a hot plate at 50° C. to give the crude product.

Synthetic Method C

To a solution of (±)-4-(3-methanesulfonylaminophenyl)-trans-3,4-dimethylpiperidine (Preparation 10, 50 mg, 0.176 mmol) in N,N-dimethylformamide (4 ml) was added sodium hydrogen carbonate (23 mg, 0.27 mmol) and the appropriate alkyl bromide (0.19 mmol), and the reaction mixture was heated at 80° C. for 24 h. Water (10 ml) was added and the mixture was extracted with ethyl acetate (2×10 ml). The combined extracts were dried (MgSO$_4$), filtered and concentrated by a steady stream of nitrogen gas over a hot plate at 50° C. to give the crude product.

Synthetic Method D

To a solution of (±)-4-(3-methanesulfonylaminophenyl)-trans-3,4-dimethylpiperidine (Preparation 10, 50 mg, 0.176 mmol) in N,N-dimethylformamide (4 ml) was added sodium hydrogen carbonate (23 mg, 0.27 mmol) and the appropriate alkyl bromide (0.19 mmol), and the reaction mixture was heated at 80° C. for 24 h. Water (10 ml) was added and the mixture was extracted with ethyl acetate (1×10 ml, 1×5 ml). The combined extracts were dried (MgSO$_4$), filtered and concentrated by a steady stream of nitrogen gas over a hot plate at 50° C. to give the crude product.

Synthetic Method E

To a solution of (+)-4-(3-methanesulfonylaminophenyl)-trans-3,4-dimethylpiperidine (Preparation 10, 40 mg, 0.141 mmol) in N,N-dimethylformamide (4 ml) was added sodium hydrogen carbonate (30 mg, 0.357 mmol) and the appropriate alkyl bromide (0.18 mmol), and the reaction mixture was heated at 100° C. for 24 h. Water (10 ml) was added and the mixture was extracted with ethyl acetate (1×10 ml, 1×5 ml). The combined extracts were dried (MgSO$_4$), filtered and concentrated by a steady stream of nitrogen gas over a hot plate at 50° C. to give the crude product.

Purification Method A

Autopurification was performed by preparative HPLC on a Phenomenex Magellan™ column, 15 cm×2.1 cm; flow 10.0 ml min$^{-1}$; employing U.V. detection at 230 nm; eluant gradient of acetonitrile:0.1M aqueous ammonium acetate solution (50:50 to 95:5).

Purification Method B

The residue was purified by silica (5 g) column chromatography eluting with dichloromethane:methanol:ammonia (100:2:1) to afford the desired product as the free base.

Purification Method C

The residue was purified by silica (10 g) column chromatography eluting with dichloromethane:methanol (30:1) to afford the desired product as the free base.

Purification Method D

The residue was purified by silica (5 g) column chromatography eluting with ethyl acetate:hexane (1:1) to afford the desired product as the free base.

Purification Method E

The residue was purified by silica (5 g) column chromatography eluting with ethyl acetate:hexane (2:1) to afford the desired product as the free base.

Purification Method F

The residue was purified by silica (5 g) column chromatography eluting with a gradient of ethyl acetate:hexane:ammonia (100:0:1 to 50:50:1) to afford the desired product as the free base.

| Example No. | Side-chain | Synthetic Method | Purification Method | Analyticals Methods | Literature Reference | Preparation No. |
|---|---|---|---|---|---|---|
| 82 | 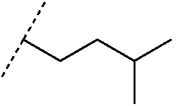 | D | A | MS (ESP): M/Z [MH+] = 353.1<br>HPLC: 16.8 mins. | | |
| 83 | 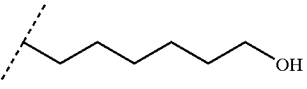 | D | A | MS (ESP): M/Z [MH+] = 383.3<br>HPLC: 1.8 mins.* | | |
| 84 | 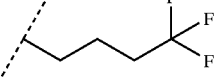 | A | A | MS (APCI): M/Z [MH+] = 393.3<br>HPLC 3.9 mins. | | |
| 85 | 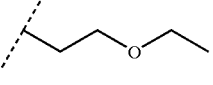 | D | A | MS (APCI): M/Z [MH+] = 355.2<br>HPLC: 14.1 mins. | | |
| 86 | 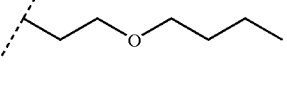 | C | A | MS (APCI): M/Z [MH+] = 383.2<br>HPLC: 17.3 mins, | | |
| 87 | 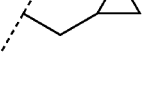 | D | A | MS (APCI): M/Z [MH+] = 337.4<br>HPLC: 2.2 mins.* | | |
| 88 | 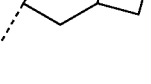 | D | A | MS (ESP): M/Z [MH+] 351.3<br>HPLC: 17.0 mins. | | |

-continued

| Example No. | Side-chain | Synthetic Method | Purification Method | Analyticals Methods | Literature Reference | Preparation No. |
|---|---|---|---|---|---|---|
| 89 | (2,3-dichlorobenzyl) | C | E | NMR (CDCl3, selected data): 7.35 (1H, d), 7.10–7.40 (5H, m) 7.05 (1H, d), 6.55 (1H br. s), 3.65 (2H, s), 3.00 (3H, s), 1.35 (3H, s), 0.80 (3H, d)<br>HPLC: 30.1 mins | 1 | |
| 90 | (4-cyanomethylbenzyl) | C | F | MS (APCI): M/Z [MH+] = 412.2<br>NMR (CDCl3, selected data): 7.00–7.20 (8H, m), 3.75 (2H, s), 3.50 (2H, q), 3.00 (3H, s), 1.30 (3H, s), 0.75 (3H, d) | 2 | |
| 91 | (naphthalen-2-ylmethyl) | A | F | MS (TSP): M/Z [MH+] = 423.2<br>HPLC: 23.9 mins. | | |
| 92 | (4-carbamoylbenzyl) | B | A | MS (ESP): M/Z [MH+] = 416.0<br>NMR (CDCl3, selected data): 7.80 (2H, d), 7.35 (2H, d), 7.00–7.35 (4H, m), 6.10 (2H, br. s), 3.60 (2H, q), 3.00 (3H, s), 1.35 (3H, s), 0.80 (3H, d) | | 32 |
| 93 | (2-(4-fluorophenyl)ethyl) | C | A | MS (ESP): M/Z [MH+] = 405.1<br>HPLC: 16.2 mins. | 3 | |
| 94 | (2-(4-cyanophenyl)ethyl) | D | A | MS (ESP): M/Z [MH+] = 412.1<br>HPLC: 15.6 mins | 4 | |
| 95 | (2-(4-methylphenyl)ethyl) | D | A | MS (APCI): M/Z [MH+] = 401.1<br>HPLC: 17.5 mins. | 5 | |
| 96 | (2-(3-chlorophenyl)ethyl) | D | A | MS (ESP): M/Z [MH+] = 421.0<br>HPLC: 18.4 mins. | 6 | |
| 97 | (2-(2-methylphenyl)ethyl) | D | A | MS (ESP): M/Z [MH+] = 401.1<br>HPLC: 19.5 mins. | 5 | |
| 98 | (2-(4-acetylphenyl)ethyl) | A | D | MS (TSP): M/Z [MH+] = 429.0<br>NMR (CDCl3, selected data): 7.90 (2H, d), 7.00–7.40 (6H, m), 3.00 (3H, s), 2.55 (3H, s) 1.30 (3H, s), 0.80 (3H, d) | | |

-continued

| Example No. | Side-chain | Synthetic Method | Purification Method | Analyticals Methods | Literature Reference | Preparation No. |
|---|---|---|---|---|---|---|
| 99 | 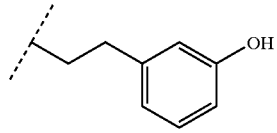 | B | A | MS (APCI): M/Z [MH+] 403.3<br>HPLC: 15.0 mins. | 7 | |
| 100 | 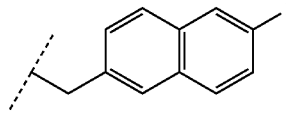 | E | A | MS (APCI): M/Z [MH+] = 441.4<br>HPLC: 28.5 mins. | 8 | |
| 101 | 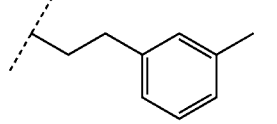 | D | A | MS (APCI): M/Z [MH+] = 401.2<br>HPLC: 21.9 mins. | 9 | |
| 102 | 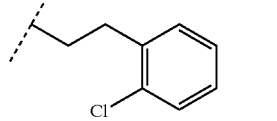 | A | A | MS (APCI): M/Z [MH+] = 421.4<br>HPLC: 5.1 mins.* | 10 | |
| 103 | 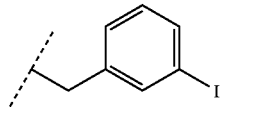 | A | A | MS (APCI): M/Z [MH+] = 499.4<br>HPLC: 29.3 mins. | | |
| 104 | 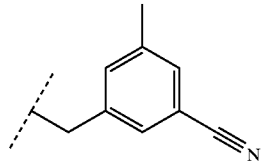 | A | A | MS (APCI): M/Z [MH+] = 412.5<br>HPLC: 27.6 mins. | 11 | |
| 105 | 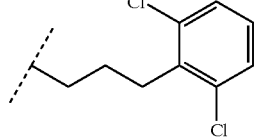 | C | D | MS (APCI): M/Z [MH+] = 469.4<br>HPLC: 32.0 mins. | 12 | |
| 106 | 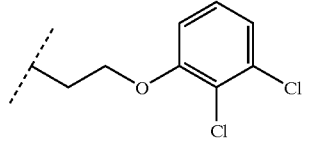 | A | A | MS (APCI): M/Z [MH+] = 471.1<br>HPLC: 5.3 mins.* | | 33 |
| 107 | 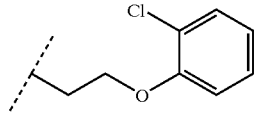 | A | A | MS (APCI): M/Z [MH+] = 437.1<br>HPLC: 3.7 mins.* | 13 | |
| 108 | 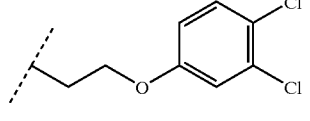 | A | A | MS (APCI): M/Z [MH+] = 471.1<br>HPLC: 5.4 mins.* | 14 | |

-continued

| Example No. | Side-chain | Synthetic Method | Purification Method | Analyticals Methods | Literature Reference | Preparation No. |
|---|---|---|---|---|---|---|
| 109 | 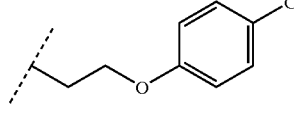 | D | A | MS (ESP): M/Z [MH+] = 437.1<br>HPLC: 2.9 mins.* | | |
| 110 | 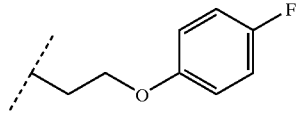 | D | A | MS (ESP): M/Z [MH+] = 421.2<br>HPLC: 2.6 mins.* | | |
| 111 | 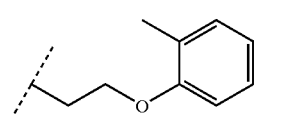 | A | A | MS (APCI): M/Z [MH+] = 417.4<br>HPLC: 24.6 mins. | | |
| 112 | 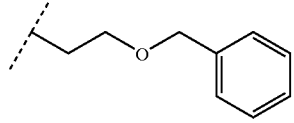 | D | A | MS (ESP): M/Z [MH+] = 417.1<br>HPLC: 18.3 mins. | 15 | |
| 113 | 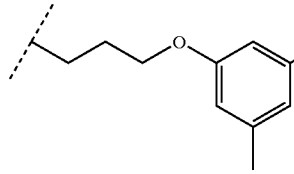 | A | C | MS (APCI): M/Z [MH+] = 445.1<br>HPLC: 25.0 mins. | 16 | |
| 114 | 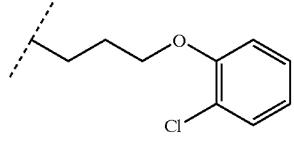 | B | A | MS (APCI): M/Z [MH+] = 451.3<br>HPLC: 24.5 mins. | 17 | |
| 115 | 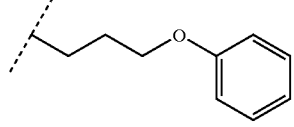 | D | E | MS (APCI): M/Z [MH+] = 417.3<br>HPLC: 18.0 mins. | | |
| 116 | 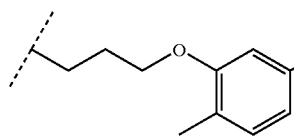 | A | A | MS (ESP): M/Z [MH+] = 445.2<br>HPLC: 25.2 mins. | | |
| 117 | 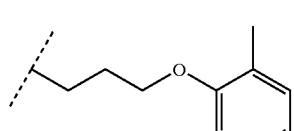 | A | A | MS (ESP): M/Z [MH+] = 445.3<br>HPLC: 27.4 mins. | 17 | |
| 118 | 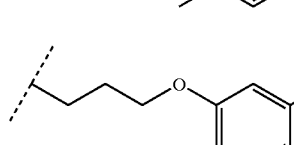 | A | A | MS (ESP): M/Z [MH+] = 431.3<br>HPLC: 26.0 mins. | 17 | |

-continued

| Example No. | Side-chain | Synthetic Method | Purification Method | Analyticals Methods | Literature Reference | Preparation No. |
|---|---|---|---|---|---|---|
| 119 | 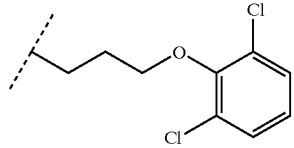 | B | F | MS (APCI): M/Z [MH+] = 485.2<br>NMR (CDCl3, selected data):<br>7.10–7.40 (5H, m), 7.05 (1H, d), 6.95<br>1H, t), 4.10 (2H, t), 3.00 (3H, s),<br>1.30 (3H, s), 0.75 (3H, d) | | 34 |
| 120 | 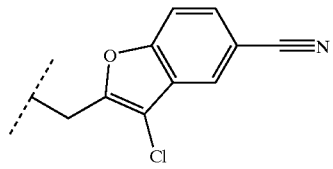 | B | F | MS (APCI): M/Z [MH+] = 472.0<br>NMR (CDCl3, selected data): 7.90<br>(1H, s), 7.50–7.70 (2H, m), 7.30<br>(1H, t), 7.00–7.15 (3H, m), 6.70<br>(1H, br. s), 3.80 (2H, s), 3.00 (3H, s),<br>1.30 (3H, s), 0.75 (3H, d) | 18 | |
| 121 | 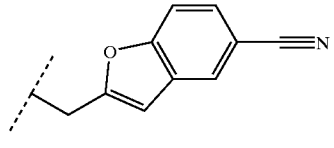 | B | F | MS (TSP): M/Z [MH+] = 437.9<br>NMR (CDCl3, selected data): 7.90<br>(1H, s), 7.50 (2H, s), 7.00–7.30<br>(4H, m) 6.70 (1H, s), 3.75 (2H, q),<br>3.00 (3H, s), 1.30 (3H, s), 0.80 (3H, d) | 18 | |
| 122 | 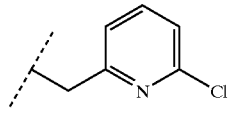 | B | B | MS (TSP): M/Z [MH+] = 408.0<br>NMR (CDCl3, selected data): 7.75<br>(1H, t), 7.50 (1H, d), 7.00–7.30<br>(5H, m), 3.75 (2H, q), 3.00 (3H, s),<br>1.30 (3H, s), 0.80 (3H, d) | 19 | |
| 123 | 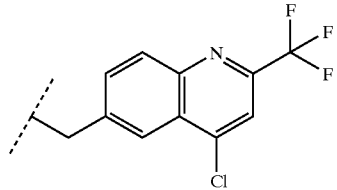 | D | C | MS (APCI): M/Z [MH+] = 526.0<br>HPLC: 31.5 mins. | | |
| 124 | 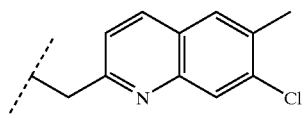 | B | C | MS (APCI): M/Z [MH+] = 472.4<br>HPLC: 11.7 mins | 20 | |
| 125 | 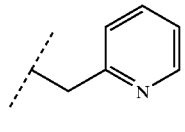 | D | A | MS (ESP): M/Z [MH+] = 374.1<br>HPLC: 16.3 mins. | | 35 |
| 126 | 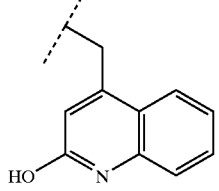 | A | D | NMR (CDCl3, selected data): 7.95<br>(1H, d), 7.50 (1H, t), 7.00–7.40<br>(6H, m) 6.80 (1H, s), 3.80 (2H, s), 3.00<br>(3H, s), 1.30 (3H, s), 0.80<br>3H, d)<br>HPLC: 20.0 mins. | | |
| 127 | 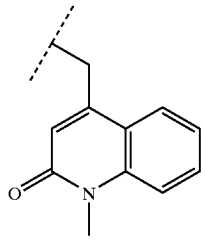 | A | E | NMR (CDCl3, selected data): 8.05<br>(1H, d), 7.55 (1H, t), 7.00–7.40<br>(6H, m) 6.80 (1H, s), 6.60 (1H br. s),<br>3.75 (3H, s), 3.60 (3H, s), 3.00<br>(3H, s), 1.30 (3H, s), 0.75 (3H, d)<br>HPLC: 22.6 mins. | | 37 |

-continued

| Example No. | Side-chain | Synthetic Method | Purification Method | Analyticals Methods | Literature Reference | Preparation No. |
|---|---|---|---|---|---|---|
| 128 | 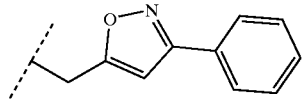 | E | A | MS (APCI): M/Z [MH+] = 440.2<br>HPLC: 24.6 mins. | | |
| 129 | 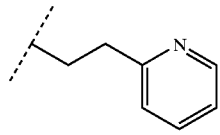 | C | A | MS (ESP): M/Z [MH+] = 388.2<br>HPLC: 13.8 mins. | 21 | |
| 130 |  | E | E | MS (APCI): M/Z [MH+] = 426.2<br>HPLC: 17.6 mins. | | |
| 131 | 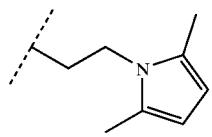 | A | D | MS (APCI): M/Z [MH+] = 404.5<br>HPLC: 25.2 mins. | | 38 |
| 132 | 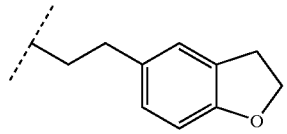 | B | A | MS (APCI): M/Z [MH+] = 429.2<br>HPLC: 19.4 mins. | 22 | |
| 133 | 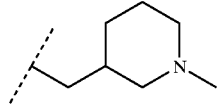 | D | A | MS (APCI): M/Z [MH+] = 394.2<br>HPLC: 17.1 mins. | | |
| 134 | 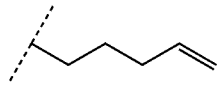 | D | A | MS (APCI): M/Z [MH+] = 351.1<br>HPLC: 16.5 mins. | | |
| 135 | 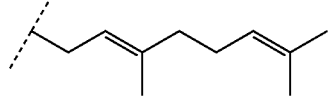 | A | A | MS (APCI): M/Z [MH+] = 419.3<br>HPLC: 4.2 mins.* | | |
| 136 | 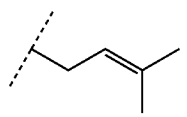 | D | A | MS (APCI): M/Z [MH+] = 351.4<br>HPLC: 2.3 mins.* | | |
| 137 | 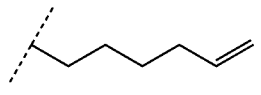 | D | A | MS (ESP): M/Z [MH+] = 365.3<br>HPLC: 18.3 mins. | | |
| 138 | 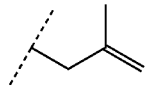 | D | A | MS (ESP): M/Z [MH+] = 337.3<br>HPLC: 16.9 mins. | | |

-continued

| Example No. | Side-chain | Synthetic Method | Purification Method | Analyticals Methods | Literature Reference | Preparation No. |
|---|---|---|---|---|---|---|
| 139 | | A | A | MS (APCI): M/Z [MH+] = 391.2<br>HPLC: 4.2 mins.* | | |
| 140 | | C | D | MS (APCI): M/Z [MH+] = 349.2<br>HPLC: 26.6 mins. | | |
| 141 | | A | A | MS (APCI): M/Z [MH+] = 444.1<br>HPLC: 16.4 mins. | | |

As indicated in the above table a number of literature preparations were used to prepare the starting alkyl bromides of Examples 89, 90, 93, 94, 95, 96, 97, 99, 100, 101, 102,104, 105, 107, 108, 112, 113, 114, 117, 118, 120, 121, 122, 124, 129 and 132.

The alkyl bromide of Example 89 was prepared via the preparation disclosed in D. C. Taylor et al, *Bioorg. Chem.*, 1987, 15, 335. The alkyl bromide of Example 90 was prepared via the preparation disclosed in E. Laurent, B. Marquet and R. Tardivel, *Tetrahedron*, 1991, 47, 3969. The alkyl bromide of Example 93 was prepared via the preparation disclosed in C. M. Suter and A. W. Weston, *J. Am. Chem. Soc.*, 1941, 63, 602. The alkyl bromide of Example 94 was prepared via the preparation disclosed in G. Wagner and H. Vieweg, *Pharmazie*, 1982, 37,13. The alkyl bromides of Example 95 and 97 were prepared via the preparation disclosed in J. H. Speer and A. J. Hill, *J. Org. Chem.*, 1937, 2, 139. The alkyl bromide of Example 96 was prepared via the preparation disclosed in M. Dukat et al, *J. Med. Chem.*, 1996, 39, 4017. The alkyl bromide of Example 97 was prepared via the preparation disclosed in B. Elpern, L. N. Gardner and L. Grumbach, *J. Am. Chem. Soc.*, 1957, 79, 1951. The alkyl bromide of Example 100 was prepared via the preparation disclosed in R. G. Jones et al, *J. Am. Chem. Soc.*, 1948, 70, 2843. The alkyl bromide of Example 101 was prepared via the preparation disclosed in A. Mitra and S. Ghoshe, *Ind. J. Chem., Sect. B* 1996, 35B, 785. The alkyl bromide of Example 102 was prepared via the preparation disclosed in R. A. Glennon et al, *J. Med. Chem.*, 1981, 24, 678. The alkyl bromide of Example 104 was prepared via the preparation disclosed in T. H. Fisher, S. M. Dershem and M. L. Prewitt, J. Org. Chem., 1990, 55, 1040. The alkyl bromide of Example 105 was prepared via the preparation disclosed in J. Augstein et al, *J. Med. Chem.*, 1967, 10, 391. The alkyl bromide of Example 107 was prepared via the preparation disclosed in J. D. Genzer, C. P. Huttrer and G. C. van Wessem, *J. Am. Chem. Soc.*, 1951, 73, 3159. The alkyl bromide of Example 108 was prepared via the preparation disclosed in C. J. Paterson-Jones, A. le Roux and T. A. Modro, *S. Afr. J. Chem.*, 1984, 37,161. The alkyl bromide of Example 112 was prepared via the preparation disclosed in A. J. Blake et al, *J. Chem. Soc., Dalton Trans.*, 1996, 23, 4379. The alkyl bromide of Example 113 was prepared via the preparation disclosed in J. Augstein et at, *J. Med. Chem.*, 1965, 8, 356. The alkyl bromides of Examples 114, 117 and 118 were prepared via the preparation disclosed in E. Reinholz et al, *Synthesis,* 1990, 1069. The alkyl bromides of Examples 120 and 121 were prepared via the preparation disclosed in P. E. Cross et al, *J. Med. Chem.*, 1986, 29, 1643. The alkyl bromide of Example 122 was prepared via the preparation disclosed in P. T. Sullivan and S. J. Norton, *J. Med. Chem.*, 1971, 14, 557. The alkyl bromide of Example 124 was prepared via the preparation disclosed in C. A. R. Baxter and H. C. Richards, *J. Med. Chem.*, 1971, 14, 1033. The alkyl bromide of Example 129 was prepared via the preparation disclosed in F. C. Nelson and G. A. Schiehser in U.S. Pat. No. 5,385,908. The alkyl bromide of Example 132 was prepared via the preparation disclosed in D. Alker et al, in EP-A-365093.

Example 142

(±)-N-Benzyl-4-(3-ethanesulfonylaminophenyl)-trans-3,4-dimethylpiperidine

To a solution of (±)-4-(3-aminophenyl)-N-benzyl-trans-3,4-dimethylpiperidine (Preparation 9, 516 mg, 1.75 mmol) in pyridine (5 ml) under nitrogen at 0° C. was added ethanesulfonyl chloride (338 mg, 2.63 mmol) dropwise, then the mixture was stirred for 64 h at room temperature. Ice water (50 ml) was added, then the mixture was extracted with diethyl ether (3×50 ml). The combined extracts were washed with brine (50 ml), dried ($Na_2SO_4$), filtered and concentrated in vacuo to give the title compound as a red oil which was used without further purification (585 mg, 86%).

NMR ($CDCl_3$, selected data for the free base): 0.8 (d, 3H), 1.3 (s, 3H), 1.35 (t, 3H), 1.6 (m, 1H), 1.95 (m, 1H), 2.25–2.55 (m, 4H), 2.85 (m, 1H), 3.1 (q, 2H), 3.45 (d, 1H), 3.6 (d, 1H) 6.25 (s, 1H), 7.05–7.4 (m, 9H).

MS (thermospray): M/Z [$MH^+$] 386.9; $C_{22}H_{30}N_2O_2S+H$ requires 387.1.

Example 143

(±)-N-Benzyl-trans-3,4-dimethyl-4-(3-n-propanesulfonylaminophenyl)piperidine

To a solution of (±)-4-(3-aminophenyl)-N-benzyl-trans-3,4-dimethylpiperidine (Preparation 9, 300 mg, 1.02 mmol)

in pyridine (5 ml) under nitrogen at 0° C., was added n-propanesulfonyl chloride (218 mg, 1.53 mmol) dropwise, and the resultant mixture was stirred for 2 d at room temperature before hydrolysing with ice (30 g). The reaction mixture was then further diluted with saturated aqueous sodium hydrogen carbonate solution (30 ml) and extracted with diethyl ether (3×50 ml). The combined extracts were washed with brine (50 ml), dried ($Na_2SO_4$), filtered and concentrated in vacuo to give a residue which was purified by silica (5 g) column chromatography eluting with ethyl acetate to afford the title compound as a light brown foam (410 mg, 99%).

NMR ($CDCl_3$, selected data for the free base): 0.8 (d, 3H), 1.0 (t, 3H), 1.3 (s, 3H), 1.6 (d, 1H), 1.85 (q, 2H), 2.0 (m, 1H), 2.4 (m, 2H), 2.85 (m, 1H), 3.05 (m, 2H), 3.55 (d, 2H), 6.35 (s, 1H), 7.0–7.4 (m, 9H).

MS (APCI): M/Z [$MH^+$] 401.2; $C_{23}H_{32}N_2O_2S+H$ required 401.2.

Example 144

(±)-N-Benzyl-trans-3,4-dimethyl-4-(3-(1-methyl-1H-imidazole-4-sulfonylamino)phenyl)piperidine To a solution of (±)4-(3-aminophenyl)-N-benzyl-trans-3,4-dimethylpiperidine (Preparation 9, 500 mg, 1.706 mmol) in pyridine (7 ml) under nitrogen was added 1-methyl-1H-imidazole-4-sulfonyl chloride (462 mg, 2.56 mmol), and the resultant mixture was stirred for 52 h before hydrolysing with ice (10 g). The reaction mixture was concentrated in vacuo at 80° C. and the residue was taken up in dichloromethane (200 ml), washed with saturated aqueous sodium hydrogen carbonate solution (70 ml), dried ($Na_2SO_4$), filtered and concentrated in vacuo to give the crude product. This was purified by silica (10 g) column chromatography eluting with ethyl acetate:triethylamine (99:1) to give the title compound as a white solid (640 mg, 86%).

NMR ($CDCl_3$, selected data for the free base): 0.5 (d, 3H), 1.1 (s, 3H), 3.6 (s, 3H), 6.8–7.4 (m, 11H).

MS (thermospray): M/Z [$MH^+$] 439.1; $C_{24}H_{30}N_4O_2S+H$ requires 439.2.

Example 145

(±)-4-(3-Ethanesulfonylaminophenyl)-trans-3,4-dimethyl-N-(5-methylhexyl)piperidine To a stirred solution of (±)4-(3-ethanesulfonylaminophenyl)-trans-3,4-dimethylpiperidine (Preparation 39, 120 mg, 0.4 mmol) in N,N-dimethylformamide (7 ml) was added sodium hydrogen carbonate (68 mg, 0.8 mmol) and 1-bromo-5-methylhexane (80 mg, 0.44 mmol). The stirred reaction mixture was heated to 100° C. for 16 h, then allowed to cool. Water (50 ml) was added and the mixture was extracted with diethyl ether (3×50 ml). The combined extracts were washed with brine (50 ml), dried ($Na_2SO_4$), filtered and concentrated in vacuo. The residue was purified by silica (5 g) column chromatography eluting initially with hexane, then hexane:ethyl acetate:0.880 ammonia (50:50:1) to give a yellow oil (15 mg). The residue was further purified by preparative HPLC on a Phenomenex Magellan™ column, 15 cm×2.1 cm; flow 10.0 ml min$^{-1}$; employing U.V. detection at 235 nm; eluant acetonitrile:0.1M aqueous ammonium acetate solution:methanol (25:35:40) to afford the title compound as its acetate salt as a yellow oil (10 mg, 6%).

NMR ($CDCl_3$, selected data for the acetate salt): 0.8 (d, 3H), 1.8 (m, 1H), 2.4 (m, 1H), 2.85 (m, 1H), 3.1 (q, 2H), 7.05–7.3 (m, 4H).

MS (APCI): M/Z [$MH^+$] 395.2; $C_{22}H_{38}N_2O_2S+H$ requires 395.3.

Example 146

(±)-4-(3-Ethanesulfonylaminophenyl)-trans-3,4-dimethyl-N-(3-phenylpropyl)piperidine To a solution of (±) 4-(3-ethanesulfonylaminophenyl)-trans-3,4-dimethylpiperidine (Preparation 39, 120 mg, 0.4 mmol) in N,N-dimethylformamide (7 ml) was added sodium hydrogen carbonate (68 mg, 0.81 mmol) and 1-bromo-3-phenylpropane (68 ml, 0.44 mmol). The stirred reaction mixture was heated to 100° C. for 16 h, then allowed to cool. Water (50 ml) was added and the mixture was extracted with diethyl ether (3×50 ml). The combined extracts were washed with brine (50 ml), dried ($Na_2SO_4$), filtered and concentrated in vacuo. The residue was purified by silica (5 g) column chromatography eluting initially with hexane, then hexane:ethyl acetate:0.880 ammonia (50:50:1) to give a yellow oil. The residue was purified by preparative HPLC on a Phenomenex Magellan™ column, 15 cm×2.1 cm; flow 10.0 ml min$^{-1}$; employing U.V. detection at 235 nm; eluant acetonitrile:0.05M aqueous ammonium acetate solution:methanol (25:35:40). The residue was diluted with water (10 ml) and extracted with diethyl ether (3×10 ml). The combined extracts were washed with brine (10 ml), dried ($Na_2SO_4$), filtered and concentrated in vacuo to give the title compound as a yellow oil (14 mg, 8%).

NMR ($CDCl_3$, selected data for the acetate salt): 0.85 (d, 3H), 1.35 (t, 3H), 1.7 (m, 1H), 1.9 (m, 2H), 2.1 (m, 1H), 2.2 (s, 3H), 2.4 (m, 1H), 2.75 (m, 2H), 3.0 (m, 1H), 3.1 (q, 2H), 7.0–7.35 (m, 9H).

MS (APCI): M/Z [$MH^+$] 415.0; $C_{24}H_{34}N_2OS+H$ requires 415.2.

Example 147

(±)-4-(3-Ethanesulfonylaminophenyl)-trans-3,4-N-(2-(3-methylphenyl)ethyl)dimethylpiperidine To a solution of (±) 4-(3-ethanesulfonylaminophenyl)-trans-3,4-dimethylpiperidine (Preparation 39, 197 mg, 0.67 mmol) and 1-(bromoethyl)-3-methylbenzene (159 mg, 0.8 mmol) in N,N-dimethylformamide (20 ml) was added sodium hydrogen carbonate (88 mg, 1.0 mmol) and the resultant mixture was heated at 80° C. under an atmosphere of nitrogen for 2 d. The reaction mixture was poured onto water (30 ml) and extracted with ethyl acetate (3×25 ml). The combined extracts were washed with water (30 ml), dried ($MgSO_4$), filtered and concentrated in vacuo to give the crude product which was purified by silica (60 g) chromatography using a gradient solvent system eluting with hexane:ethyl acetate (2:1) to afford the title compound as a pale yellow oil (95 mg, 34%).

NMR ($CDCl_3$, selected data for the free base): 0.8 (d, 3H), 1.35 (t, 3H), 2.0 (m, 1H), 2.3 (s, 3H), 2.9 (m, 1H), 3.1 (q, 2H), 7.0–7.3 (m, 8H).

MS (APCI): M/Z [$MH^+$] 415.2; $C_{24}H_{34}N_2O_2S+H$ requires 415.2.

Example 148

(±)-trans-3,4-Dimethyl-N-(5-methylhexyl)-4-(3-n-propanesulfonylaminophenyl)piperidine To a solution of (±)-trans-3,4-dimethyl-4-(3-n-propanesulfonylaminophenyl)piperidine (Preparation 40, 220 mg, 0.71 mmol) and 1-bromo-5-methylhexane (140 mg, 0.78 mmol) in N,N-dimethylformamide (7 ml) was added sodium hydrogen carbonate (120 mg, 1.42 mmol) and the resultant mixture was heated overnight at 100° C. The reaction mixture was poured onto water (50 ml) and extracted with diethyl ether (3×50 ml). The combined extracts were washed with brine (50 ml), dried (MgSO$_4$), filtered and concentrated in vacuo to give the crude product which was purified by silica (5 g) chromatography using a gradient solvent system eluting initially with hexane:0.880 ammonia (100:1) then ethyl acetate:hexane:0.880 ammonia (50:50:1) to afford the title compound as a pale yellow oil (77 mg, 27%).

NMR (CDCl$_3$, selected data for the free base): 0.75 (d, 3H), 0.9 (d, 6H), 1.0 (t, 3H), 1.2 (t, 2H), 1.25 (m, 2H), 1.3 (s, 3H), 1.4–1.65 (m, 5H), 1.8 (m, 2H), 2.0 (m, 1H), 2.5 (q, 2H), 2.8 (m, 1H), 3.05 (m, 2H), 7.0–7.3 (m, 4H).

MS (APCI): M/Z [MH$^+$] 409.3; C$_{23}$H$_{40}$N$_2$O$_2$S+H requires 409.3.

Example 149

(±)-N-(3-Cyclohexylpropyl)-trans-3,4-dimethyl-4-(3-n-propanesulfonylaminophenyl)piperidine To a solution of (±)-trans-3,4-dimethyl-4-(3-n-propanesulfonylaminophenyl)piperidine (Preparation 40, 220 mg, 0.71 mmol) in N,N-dimethylformamide (7 ml) was added sodium hydrogen carbonate (66 mg, 0.78 mmol) and 1-chloro-3-cyclohexylpropane (126 ml, 0.78 mmol). The stirred reaction mixture was heated at 100° C. for 12 h, then concentrated in vacuo to give a non-volatile residue. The residue was purified by silica (10 g) column chromatography eluting with dichloromethane then dichloromethane:methanol (9:1). The residue was further purified by silica (10 g) column chromatography eluting with dichloromethane:isopropanol (19:1) to give the title compound as an oil (10 mg, 3%).

NMR (CDCl$_3$, selected data for the free base): 0.75 (m, 3H), 0.85 (m, 3H), 1.0 (t, 2H), 1.85 (m, 2H), 3.05 (t, 2H), 7.0–7.35 (m, 4H).

Example 150

(±)-trans-3,4-Dimethyl-N-(3-phenylpropyl)-4-(3-propanesulfonylaminophenyl)piperidine To a solution of (±)-trans-3,4-dimethyl-4-(3-propanesulfonylaminophenyl)piperidine (Preparation 40, 220 mg, 0.71 mmol) in N,N-dimethylformamide (7 ml) was added sodium hydrogen carbonate (120 mg, 1.4 mmol) and 1-bromo-3-phenylpropane (0.12 ml, 156 mg, 0.78 mmol). The mixture was heated to 100° C. for 16 h and then allowed to cool. Water (50 ml) was added and the mixture was extracted with diethyl ether (3×50 ml). The combined extracts were washed with brine (50 ml), dried (Na$_2$SO$_4$), filtered and concentrated in vacuo. The residue was purified by silica (5 g) column chromatography eluting initially with hexane, then hexane:ethyl acetate:0.880 ammonia (50:50:1) to give a yellow oil. The residue was purified by preparative HPLC on a Phenomenex Magellan™ column, 15 cm×2.1 cm; flow 10.0 ml min$^{-1}$; employing U.V. detection at 235 nm; eluant acetonitrile:0.05M aqueous ammonium acetate solution:methanol (25:35:40). The residue was diluted with water (50 ml) and extracted with diethyl ether (2×50 ml). The combined extracts were washed with brine (30 ml), dried (MgSO$_4$), filtered and concentrated in vacuo to give the title compound as its acetate salt as a yellow oil (9 mg, 3%).

NMR (CDCl$_3$, selected data for the acetate salt): 0.8 (d, 3H), 1.0 (t, 3H), 1.3 (m, 2H), 1.6 (m, 1H), 2.0 (m, 1H), 2.8 (m, 1H), 3.05 (t, 2H), 7.0–7.35 (m, 9H).

MS (thermospray): M/Z [MH$^+$] 429.1; C$_{25}$H$_{36}$N$_2$O$_2$S+H requires 429.2.

Example 151

(±)-trans-3,4-Dimethyl-N-(5-methylhexyl)-4-(3-(1-methyl-1H-imidazole-4-sulfonylamino)phenyl)piperidine To a solution of (±)-trans-3,4-dimethyl-4-(3-(1-methyl-1H-imidazole-4-sulfonylamino)phenyl)piperidine (Preparation 41, 80 mg, 0.23 mmol) in N,N-dimethylformamide (3 ml) was added sodium hydrogen carbonate (21 mg, 0.25 mmol) and 1-bromo-5-methylhexane (43 mg, 0.24 mmol). The stirred reaction mixture was heated at 100° C. for 5 h, then concentrated in vacuo at 80° C. The residue was taken up in dichloromethane and purified by silica column chromatography, eluting with ethyl acetate:isopropanol (95:5) to give the title compound as a white solid (34 mg, 33

NMR (CDCl$_3$, selected data for the free base): 0.6 (d, 3H), 0.85 (m, 6H), 1.25 (s, 3H), 3.6 (s, 3H), 7.0–7.25 (s, 5H), 7.45 (s, 1H).

MS (thermospray): M/Z [MH$^+$] 447.3; C$_{24}$H$_{38}$N$_4$O$_2$S+H requires 447.3.

Example 152

(±)-N-(3-Cyclohexylpropyl)-trans-3,4-dimethyl-4-(3-(1-methyl-1H-imidazole-4-sulfonylamino)phenyl)piperidine To a solution of (+)-trans-3,4-dimethyl-4-(3-(l1-methyl-1H-imidazole-4-sulfonylamino)phenyl)piperidine (Preparation 41, 190 mg, 0.55 mmol) in N,N-dimethylformamide (6 ml) was added sodium hydrogen carbonate (50 mg, 0.60 mmol) and 1-chloro-3-cyclohexylpropane (97 ml, 0.60 mmol). The stirred reaction mixture was heated at 100° C. for 12 h, then concentrated in vacuo to give a non-volatile residue. The residue was purified by silica (10 g) column chromatography eluting with dichloromethane then dichloromethane:methanol (9:1). The residue was further purified by silica (10 g) column chromatography eluting with ethyl acetate:isopropanol (19:1). The residue was further purified by silica (10 g) column chromatography eluting with dichloromethane:isopropanol:triethylamine (19:1:0.1) to give the title compound (43 mg, 17%).

NMR (CDCl$_3$, selected data for the free base): 0.6 (d, 3H), 0.95 (m, 3H), 3.6 (s, 3H), 7.0–7.25 (m, 5H), 7.5 (s, 1H).

MS (APCI): M/Z [MH$^+$] 473.5; C$_{26}$H$_{40}$N$_4$O$_2$S+H requires 473.3.

Example 153

(±)-trans-3,4-Dimethyl-4-(3-(1-methyl-1H-imidazole-4-sulfonylamino)phenyl)-N-(3-phenylpropyl)piperidine To a solution of (±)-trans-3,4-dimethyl-4-(3-(1-methyl-1H-imidazole-4-sulfonylamino)phenyl)piperidine (Preparation 41, 80 mg, 0.23 mmol) in N,N-dimethylformamide (3 ml) was added sodium hydrogen carbonate (21 mg, 0.25 mmol) and 1-bromo-3-phenylpropane (37 ml, 0.24 mmol). The stirred reaction mixture was heated at 100° C. for 5 h, then concentrated in vacuo to give a non-volatile residue. The residue was purified by silica (10 g) column chromatography eluting with dichloromethane then dichloromethane:methanol (9:1). The residue was further purified by silica (10 g) column chromatography eluting with dichloromethane:isopropanol (19:1) to give the title compound as an off white solid (29 mg, 27%).

NMR (CDCl$_3$, selected data for the free base): 0.6 (d, 3H), 1.25 (m, 3H), 2.65 (t, 2H), 3.6 (s, 3H), 7.0–7.35 (m, 10H), 7.45 (s, 1H).

MS (APCI): M/Z [MH$^+$] 467.5; $C_{26}H_{34}N_4O_2S$+H requires 467.2.

Example 154

(±)-N-Hexyl-trans-3,4-dimethyl-4-(3-(N-methyl-methanesulfonylamino)phenyl)piperidine To a solution of (±)-N-hexyl-trans-3,4-dimethyl-4-(3-N-methylaminophenyl)piperidine (Preparation 42, 70 mg, 0.23 mmol) in pyridine (2 ml) at 0° C. was added methanesulfonyl chloride (0.3 ml). The solution was stirred at room temperature under nitrogen for seven days. The mixture was partitioned between dichloromethane (5 ml) and water (5 ml). The organic layer was separated and the aqueous layer was extracted with dichloromethane (2×5 ml). The combined extracts were dried (Na$_2$SO$_4$), filtered and concentrated in vacuo to give the crude product which was purified by silica (5 g) column chromatography eluting with ethyl acetate:hexane:0.880 ammonia (40:60:1) to give the title compound as a clear oil (40 mg, 43%).

NMR (CDCl$_3$, selected data for the free base): 0.75 (d, 3H), 0.9 (m, 3H), 1.25 (m, 8H), 1.4–1.65 (m, 4H), 2.0 (m, 1H), 2.2–2.55 (m, 7H), 2.8 (s, 3H), 3.25 (s, 3H), 7.1–7.4 (m, 4H).

MS (thermospray): M/Z [MH$^+$] 381.2; $C_{21}H_{36}N_2O_2S$+H requires 381.3.

Example 155

(±)-4-(4-Chloro-3-(methanesulfonylamino)phenyl)-N-hexyl-trans-3,4-dimethylpiperidine To a stirred solution of (±)-N-hexyl-4-(3-methanesulfonylaminophenyl)-trans-3,4-dimethylpiperidine (Example 4, 71 mg, 0.176 mmol) in dichloromethane (5 ml) at 0 C. was added a 0.38M solution of chlorine in acetic acid (0.67 ml, 0.25 mmol) dropwise over 4 h. Hplc analysis indicated complete consumption of starting material. The reaction mixture was basified to pH 8 using saturated aqueous sodium hydrogen carbonate solution, then it was extracted with dichloromethane (2×20 ml). The combined extracts were dried (MgSO$_4$), filtered and concentrated in vacuo to give the crude product which was purified by silica (5 g) column chromatography eluting with ethanol:dichloromethane:0.880 ammonia (4:100:1) to give the title compound as a clear oil (31 mg, 44%).

NMR (CDCl$_3$, selected data for the free base): 0.75 (d, 3H), 0.9 (m, 3H), 2.0 (m, 1H), 2.2–2.55 (m, 6H), 2.8 (m, 1H), 2.95 (s, 3H), 7.0–7.6 (m, 3H).

MS (thermospray): M/Z [MH$^+$] 401.3; $C_{20}H_{33}ClN_2O_2S$+H requires 401.2.

Example 156

(±)-4-(6-Chloro-3-(methanesulfonylamino)phenyl)-N-hexyl-trans-3,4-dimethylpiperidine Further elution as described in Example 155 provided the title compound as a colourless oil (29 mg, 41%).

NMR (CDCl$_3$, selected data for the free base): 0.75 (d, 3H), 0.9 (m, 3H), 2.2–2.4 (m, 5H), 2.6 (d, 1H), 2.9 (m, 1H), 3.0 (s, 3H), 7.0–7.35 (m, 3H).

MS (thermospray): M/Z [MH$^+$] 401.3; $C_{20}H_{33}ClN_2O_2S$+H requires 401.2.

Example 157

(±)-4-(4,6-Dichloro-3-(methanesulfonylamino)phenyl)-N-hexyl-trans-3,4-dimethylpiperidine To a stirred solution of (±)-N-hexyl-4-(3-methanesulfonylaminophenyl)-trans-3,4-dimethylpiperidine (Example 4, 70 mg, 0.2 mmol) in dichloromethane (5 ml) at 0° C. was added a 1.08M solution of chlorine in acetic acid (0.48 ml, 0.52 mmol) dropwise and the solution was stirred at 0° C. for 2 h. A further addition of a 1.08M solution of chlorine in acetic acid (0.48 ml, 0.52 mmol) was made and the solution was allowed to warm to room temperature and stirred overnight. The reaction mixture was basified to pH 8 using saturated aqueous sodium hydrogen carbonate solution, then it was extracted with dichloromethane (3×10 ml). The combined extracts were dried (Na$_2$SO$_4$), filtered and concentrated in vacuo to give the crude product which was purified by silica (5 g) column chromatography eluting with ethanol:dichloromethane:0.880 ammonia (5:94:1) to give the title compound as a clear oil (26 mg, 30%).

NMR (CDCl$_3$, selected data for the free base): 0.85 (d, 3H), 0.9 (m, 3H), 2.2–2.55 (m, 6H), 2.6 (m, 1H), 2.95 (m, 2H), 3.0 (s, 3H), 7.15 (s, 1H), 7.80 (s, 1H).

MS (APCI): M/Z [MH$^+$] 435.1; $C_{20}H_{33}Cl_2N_2O_2S$+H requires 435.2.

Example 158

N-Hexyl-4-(3-(2-hydroxy-2-methylpropanoylamino)phenyl)piperidine

To a solution of 4-(3-(1-carbamoyl-1-methylethoxy)phenyl)-N-hexylpiperidine (Preparation 49, 390 mg, 1.13 mmol) in N-methylpyrrolidinone (5 ml) under an atmosphere of nitrogen was added sodium hydride (60% dispersion in mineral oil, 93 mg, 2.32 mmol). The resultant mixture was stirred for 30 min and then heated under reflux overnight. The reaction mixture was cooled, carefully poured onto water (10 ml) and extracted with ethyl acetate (3×15 ml). The combined extracts were dried (MgSO$_4$) and concentrated in vacuo to give the title compound as an orange oil which was not purified further.

NMR (CDCl$_3$, selected data for the free base): 0.85 (m, 3H), 7.0–7.5 (m, 4H), 8.65 (br.s, 1H).

Example 159

N-Hexyl-4-(3-methanesulfonylaminophenyl)piperidine

To a solution of 4-(3-aminophenyl)-N-hexylpiperidine (Preparation 50, 178 mg, 0.68 mmol) in pyridine (5 ml) at room temperature under an atmosphere of nitrogen was added methanesulfonyl chloride (79 ml, 1.03 mmol) over 10 min. The resultant mixture was stirred overnight, poured onto water (10 ml) and extracted with ethyl acetate (3×10 ml). The combined extracts were dried (MgSO$_4$) and concentrated in vacuo at 80° C. to give the crude product which was purified by silica column chromatography, eluting with ethyl acetate:hexane:0.880 ammonia (90:9:1) to give the title compound as a pale brown oil (150 mg, 65%).

NMR (CDCl$_3$, selected data for the free base): 0.85 (m, 3H), 1.3 (m, 6H), 1.6 (m, 2H), 2.4–2.6 (m, 2H), 3.0 (s, 3H), 3.2 (m, 2H), 7.0–7.3 (m, 4H).

MS (thermospray): M/Z [MH$^+$] 339.5; C$_{18}$H$_{30}$N$_2$O$_2$S+H requires 339.2.

Example 160

N-Hexyl-4-(3-methanesulfonylaminophenyl)-4-methylpiperidine

To 4-(3-aminophenyl)-N-hexyl-4-methylpiperidine (Preparation 56, 70.0 mg, 0.27 mmol) in dichloromethane (3 ml) was added methanesulfonyl chloride (61 mg, 0.53 mmol) in dichloromethane (0.5 ml) and pyridine (42 mg, 0.53 mmol) in dichloromethane (0.5 ml) at room temperature. The solution was stirred at room temperature for 16 h, then it was concentrated in vacuo to give the crude product. This was purified by silica column chromatography eluting with a gradient of ethyl acetate:hexane:0.88 ammonia (90:10:1 to 98:2:1) to give the title compound as a colourless oil (65 mg, 72%).

NMR (CDCl$_3$, selected data for the free base): 0.85 (m, 3H), 1.65 (m, 2H), 2.0 (m, 2H), 2.3 (m, 2H), 2.6–2.95 (m, 6H), 3.0 (s, 3H), 7.1–7.4 (m, 4H).

MS (APCI): M/Z [MH$^+$] 353.3; C$_{19}$H$_{32}$N$_2$O$_2$S+H requires 353.2.

Example 161

4-(3-Ethanesulfonylaminophenyl)-N-hexyl-4-methylpiperidine

To 4-(3-aminophenyl)-N-hexyl-4-methylpiperidine (Preparation 56, 50.0 mg, 0.18 mmol) in dichloromethane (1 ml) was added ethanesulfonyl chloride (47 mg, 0.37 mmol) in dichloromethane (1 ml) and pyridine (30 mg, 0.37 mmol) in dichloromethane (1 ml) at room temperature. The solution was stirred at room temperature for 20 h, then it was concentrated in vacuo to give the crude product. This was purified by silica column chromatography eluting with ethyl acetate:hexane:0.880 ammonia (98:2:1) to give the title compound as a colourless oil (55 mg, 82%).

NMR (CDCl$_3$, selected data for the free base): 0.85 (m, 3H), 1.2 (s, 3H), 1.3 (m, 6H), 1.4 (t, 3H), 1.45 (m, 2H), 1.8 (m, 2H), 2.1 (m, 2H), 2.3 (m, 2H), 2.4–2.6 (m, 4H), 3.1 (q, 2H), 7.05–7.2 (m, 3H), 7.3 (m, 1H).

MS (thermospray): M/Z [MH$^+$] 366.9; C$_{20}$H$_{34}$N$_2$O$_2$S+H requires 367.2.

Example 162

N-Hexyl-4-methyl-4-(3-n-propanesulfonylaminophenyl)piperidine

To 4-(3-aminophenyl)-N-hexyl-4-methylpiperidine (Preparation 56, 72.0 mg, 0.26 mmol) in dichloromethane (1 ml) was added n-propanesulfonyl chloride (75 mg, 0.53 mmol) in dichloromethane (1 ml) and pyridine (42 mg, 0.53 mmol) in dichloromethane (1 ml) at room temperature. The solution was stirred at room temperature for 20 h, then it was concentrated in vacuo to give the crude product. This was purified by silica column chromatography eluting with ethyl acetate:0.880 ammonia (100:1) to give the title compound as a colourless oil (80 mg, 80%).

NMR (CDCl$_3$, selected data for the free base): 0.85 (m, 3H), 1.0 (t, 3H), 1.2 (s, 3H), 1.3 (m, 6H), 1.45 (m, 2H), 1.75–1.95 (m, 4H), 2.1 (m, 2H), 2.3 (m, 2H), 2.4–2.6 (m, 4H), 3.1 (m, 2H), 3.05 (q, 2H), 7.05–7.2 (m, 3H), 7.30 (m, 1H).

MS (thermospray): M/Z [MH$^+$] 381.5; C$_{21}$H$_{36}$N$_2$O$_2$S+H requires 381.3.

Example 163

4-Ethyl-N-hexyl-4-(3-methanesulfonylaminophenyl)piperidine

To 4-(3-aminophenyl)-4-ethyl-N-hexylpiperidine (Preparation 64, 50.0 mg, 0.174 mmol) in anhydrous pyridine (4 ml) under nitrogen at 0° C. was added methanesulfonyl chloride (0.2 ml, 1.18 mmol). The solution was stirred at room temperature for 48 h. Ice (5 g) was added and, after 30 min, the reaction mixture was extracted with dichloromethane (10 ml). The organic extract was dried (Na$_2$SO$_4$), filtered and concentrated in vacuo to give the crude product which was purified by silica (5 g) column chromatography, eluting with ethyl acetate:hexane:0.880 ammonia (40:60:1), then ethyl acetate:0.880 ammonia (100:1) and then methanol:ethyl acetate:0.880 ammonia (10:89:1) to give the title compound as an oil (20 mg, 29%).

NMR (CDCl$_3$, selected data for free base): 0.55 (t, 3H), 0.85 (m, 3H), 1.9 (m, 2H), 2.0 (s, 3H), 2.7 (m, 2H), 3.0 (s, 3H), 7.05–7.35 (m, 4H).

MS (thermospray): M/Z [MH$^+$] 367.4; C$_{20}$H$_{34}$N$_2$O$_2$S+H requires 367.2.

Example 164

4-(3-Ethanesulfonylaminophenyl)-4-ethyl-N-hexylpiperidine

To 4-(3-aminophenyl)-4-ethyl-N-hexylpiperidine (Preparation 64, 50.0 mg, 0.174 mmol) in anhydrous pyridine (4 ml) under nitrogen at 0° C. was added ethanesulfonyl chloride (0.2 ml, 1.15 mmol). The solution was stirred at room temperature for 48 h. Ice (5 g) was added and, after 30 min, the reaction mixture was extracted with dichloromethane (10 ml). The organic extract was dried (Na$_2$SO$_4$), filtered and concentrated in vacuo to give the crude product which was purified by silica (5 g) column chromatography, eluting with ethyl acetate:hexane:0.880 ammonia (50:50:1) and then methanol:ethyl acetate:0.880 ammonia (10:89:1) to give the title compound as an oil (22 mg, 30%).

NMR (CDCl$_3$, selected data for the free base): 0.6 (t, 3H), 0.85 (m, 3H), 1.4 (t, 3H), 1.95 (m, 1H), 2.8 (m, 1H), 3.1 (q, 2H), 7.0–7.35 (m, 4H).

MS (thermospray): M/Z [MH$^+$] 381.2; C$_{21}$H$_{36}$N$_2$O$_2$S+H requires 381.3.

Example 165

N-Hexyl-4-(3-methanesulfonylaminophenyl)-4-n-propylpiperidine

To a solution of 4-(3-aminophenyl)-N-hexyl-4-n-propylpiperidine (Preparation 70, 25 mg, 0.08 mmol) in pyridine (0.5 ml) under nitrogen was added methanesulfonyl chloride (10 ml, 0.124 mmol) and the resultant mixture was stirred overnight. Ice (2 g) was added and, after 15 min, dichloromethane (3 ml) was added and the biphasic mixture was left to stir for 15 min. The layers were separated and the aqueous layer was extracted with dichloromethane (3 ml). The combined extracts were dried (Na$_2$SO$_4$) and concentrated in vacuo to give the crude product. This was purified by silica (5 g) column chromatography eluting with ethyl acetate:hexane:0.880 ammonia (60:40:1 to 80:20:1) to give the title compound as a colourless oil (28 mg, 92%). The free base was dissolved in diethyl ether (3 ml) and 1.1 mol equivalents of 1N ethereal hydrogen chloride solution was added to provide a precipitate. The solvent was decanted and the solid dried in vacuo to yield the title compound as a hygroscopic solid.

NMR (CDCl$_3$, selected data for the hydrochloride salt): 3.0 (s, 3H), 3.4 (m, 2H), 6.8–7.4 (m, 4H), 12.05 (br. m, 1H).

MS (thermospray): M/Z [M$^+$] 381.4; C$_{21}$H$_{36}$N$_2$O$_2$S+H requires 381.3.

Example 166

4-(3-Ethanesulfonylaminophenyl)-N-hexyl-4-n-propylpiperidine

To a solution of 4-(3-aminophenyl)-N-hexyl-4-n-propylpiperidine (Preparation 70, 34 mg, 0.11 mmol) in pyridine (0.5 ml) under nitrogen was added ethanesulfonyl chloride (16 ml, 0.17 mmol) and the resultant mixture was stirred overnight. Ice (2 g) was added and, after 15 min, dichloromethane (3 ml) was added and the biphasic mixture was left to stir for 15 min. The layers were separated and the aqueous layer was extracted with dichloromethane (3 ml). The combined extracts were dried (Na$_2$SO$_4$) and concentrated in vacuo to give the crude product. This was purified by silica (5 g) column chromatography eluting with ethyl acetate:hexane:0.880 ammonia (40:60:1 to 75:25:1) to give the title compound as a pale yellow oil (26 mg, 60%).

NMR (CDCl$_3$, selected data for the free base): 0.75 (t, 2H), 1.8 (m, 2H), 2.6 (m, 2H), 3.1 (q, 2H), 7.0–7.3 (m, 4H).

MS (thermospray): M/Z [M$^+$] 395.5; C$_{22}$H$_{38}$N$_2$O$_2$S+H requires 395.3.

Example 167

(±)-N-Hexyl-4-(3-methanesulfonylamino-4-methylphenyl)-trans-3,4-dimethylpiperidine To a solution of (±)-4-(3-amino-4-methylphenyl)-N-hexyl-trans-3,4-dimethylpiperidine (Preparation 75, 30.0 mg, 0.10 mmol) in dichloromethane (1.0 ml) was added a solution of pyridine (16 mg, 0.20 mmol) in dichloromethane (0.4 ml) and a solution of methanesulfonyl chloride (23 mg, 0.20 mmol) in dichloromethane (0.4 ml) at room temperature. The solution was stirred at room temperature for 16 h and then concentrated in vacuo to give the crude product. This was purified by silica column chromatography eluting with hexane:ethyl acetate:ammonia (50:50:1). Further purification was achieved by preparative HPLC on a Phenomenex Magellan™ column, 15 cm×2.1 cm; flow 10.0 ml min$^{-1}$; employing U.V. detection at 230 nm; eluant gradient of acetonitrile:0.1M aqueous ammonium acetate solution (40:60 to 95:5) to afford the title compound as its acetate salt. This was dissolved in 1N aqueous sodium hydroxide solution (1 ml) and extracted with dichloromethane (3×1 ml). The combined extracts were dried (MgSO$_4$), filtered and concentrated in vacuo to give the title compound as a colourless oil (3.0 mg, 8%).

NMR (CDCl$_3$, selected data for the free base): 0.8 (d, 3H), 0.9 (m, 3H), 1.45 (m, 2H), 1.6 (m, 1H), 2.25 (s, 3H), 2.55 (m, 2H), 2.8 (m, 1H), 3.0 (s, 3H), 7.05–7.4 (m, 4H).

MS (APCI): M/Z [MH$^+$] 381.2; C$_{21}$H$_{36}$N$_2$O$_2$S+H requires 381.3.

Example 168

(±)-N-Hexyl-4-(3-methanesulfonylaminophenyl)-trans-(3R,4R)-dimethylpiperidine (R)-N-oxide To a solution of (+)-N-hexyl-4-(3-methanesulfonylaminophenyl)-trans-3,4-dimethylpiperidine (Example 5, 230 mg, 0.625 mmol) in acetone (10 ml) was added 30% w:w aqueous hydrogen peroxide solution (2 ml) using a glass pipette, and the reaction mixture was stirred at room temperature overnight. Using a stream of nitrogen, the mixture was concentrated to approximately 3 ml in volume, and the more concentrated solution was stirred at room temperature for 3 d. Using a stream of nitrogen, the remaining acetone was removed, and the aqueous mixture was partitioned between water (5 ml) and dichloromethane (5 ml). The layers were separated, and the aqueous layer was extracted with dichloromethane (2×5 ml). The combined extracts were washed with water (5 ml), dried (Na$_2$SO$_4$), filtered and concentrated to afford an oil which was not purified further (225 mg, 94% crude yield). A sample (50 mg) of the diastereomeric N-oxides was separated by preparative HPLC on a Phenomenex Magellan™ column, 15 cm×2.1 cm; flow 10.0 ml min$^{-1}$; employing U.V. detection at 230 nm; eluant gradient of acetonitrile:0.1M aqueous ammonium acetate solution (50:50 to 95:5) to afford the title compound as a colourless oil (5.5 mg).

NMR (CDCl$_3$, selected data): 0.85–0.95 (m, 6H), 3.0 (s, 3H), 3.4–3.55 (m, 3H), 3.8 (m, 1H), 4.15 (m, 1H), 7.05 (m, 1H), 7.3–7.45 (m, 3H).

MS (electrospray): M/Z [MH$^+$] 383.1; C$_{20}$H$_{34}$N$_2$O$_3$S+H requires 383.2.

Example 169

(+)-N-Hexyl-4-(3-methanesulfonylaminophenyl)-trans-(3R,4R)-dimethylpiperidine (S)-N-oxide Further elution as described in Example 168 provided the title compound as a colourless oil (9.5 mg).

NMR (CDCl$_3$, selected data): 0.85 (m, 3H), 1.1 (d, 1H), 1.8 (m, 2H), 2.6 (m, 1H), 2.8 (m, 1H), 3.0 (s, 3H), 3.0–3.3 (m, 2H), 3.4–3.55 (m, 3H), 3.7 (m, 1H), 7.05–7.2 (m, 2H), 7.25–7.4 (m, 2H).

MS (electrospray): M/Z [MH$^+$] 383.1; C$_{20}$H$_{34}$N$_2$O$_3$S+H requires 383.2.

Example 170

(+)-N-Hexyl-4-(3-methanesulfonylaminophenyl)-trans-3,4-dimethylpiperidine

To a solution of crude (+)-4-(3-aminophenyl)-N-hexyl-trans-3,4-dimethylpiperidine (Preparation 84, 4.3 g, 14.9 mmol) in toluene (30 ml) at 0° C. under an atmosphere of nitrogen was added triethylamine (4.6 ml, 32.8 mmol), followed by methanesulfonyl chloride (2.54 ml, 32.8 mmol) added over a period of 15 min at such a rate that the internal temperature did not rise above 10° C. The resultant mixture was stirred at room temperature for 18 h after which time water (40 ml) was added. The resultant slurry was diluted with ethyl acetate (150 ml), and the phases were separated. The organic phase was concentrated in vacuo to give an orange gum which was dissolved in toluene (30 ml). Water (10 ml) and 2M aqueous sodium hydroxide solution (15 ml, 30 mmol) were added, and the resultant mixture was heated under reflux for 18 h. The reaction mixture was cooled to 0° C. and the pH was adjusted to 8 by the addition of concen trated hydrochloric acid. Saturated aqueous sodium hydrogen carbonate solution (20 ml) was added and the mixture was stirred for 15 min. The layers were separated and the aqueous phase was extracted with toluene (30 ml). The combined extracts were dried (MgSO$_4$), filtered and concentrated in vacuo to give the crude title compound (4.69 g). In the present synthetic route the crude product so formed was taken forward into the next step without any purification. However, purification, for example by silica column chromatography eluting with a gradient of diethyl ether:hexane:diethylamine (20:80:1 to 100:0:1) affords the analytically pure title compound.

NMR (CDCl$_3$, selected data for the free base): 0.8 (d, 3H), 0.9 (m, 3H), 1.1–1.7 (m, 13H), 1.9–2.05 (m, 1H), 2.2–2.45 (m, 4H), 2.45 (m, 1H), 2.6 (m, 1H), 2.85 (m, 1H), 3.00 (s, 3H), 7.0 (m, 1H), 7.1–7.4 (m, 3H).

Example 171

(+)-N-Hexyl-4-(3-methanesulfonylaminophenyl)-trans-3,4-dimethylpiperidine (1R)-(−)-10-camphorsulfonate salt To a solution of crude (+)-N-hexyl-4-(3-methanesulfonylaminophenyl)-trans-3,4-dimethylpiperidine (Example 170, 4.69 g, 12.8 mmol) in Industrial Methylated Spirits (60 ml) was added (1R)-(−)-10-camphorsulfonic acid (3.21 g, 12.8 mmol) and the resultant mixture was heated at 50° C. until a clear solution had formed. The solvent was removed in vacuo, and the residue was re-crystallised from butanone (55 ml). The resultant suspension was cooled to 0° C. and the solid was collected by filtration, washed with butanone (10 ml) and dried in vacuo to give the title compound as a white solid (4.83 g, 61%).

m.p. 180° C. Found C, 58.99; H, 8.25; N, 4.50. C$_{30}$H$_{50}$N$_2$O$_6$S$_2$·0.5 H$_2$O requires C, 59.2; H, 8.45; N, 4.63%.

Example 172

(+)-N-Hexyl-4-(3-methanesulfonylaminophenyl)-trans-3,4-dimethylpiperidine (1S)-(+)-10-camphorsulfonate salt To a solution of crude (+)-N-hexyl-4-(3-methanesulfonylaminophenyl)-trans-3,4-dimethylpiperidine (Example 170, 12.65 g, 34.5 mmol) in Industrial Methylated Spirits (150 ml) was added (1S)-(+)-10-camphorsulfonic acid (8.81 g, 35.2 mmol) and the resultant mixture was heated at 50° C. until a clear solution had formed. The solvent was removed in vacuo, and the residue was re-crystallised from butanone (110 ml). The resultant suspension was cooled to 0° C. and the solid was collected by filtration, washed with butanone (15 ml) and dried in vacuo to give the title compound as a white solid (13.9 g, 65%).

m.p. 175° C. Found C, 59.15; H, 8.41; N, 4.71. C$_{30}$H$_{50}$N$_2$O$_6$S$_2$·0.5 H$_2$O requires C, 59.2; H, 8.45; N, 4.63%.

Example 173

Formulation of (+)-N-Hexyl-4-(3-methanesulfonylaminophenyl)-trans-3,4-dimethylpiperidine A composition suitable for oral gavage administration is as follows:

| | |
|---|---|
| (+)-N-Hexyl-4-(3-methanesulfonylaminophenyl)-trans-3,4-dimethylpiperidine hydrochloride salt (Example 5a) | 220 mg |
| Propylene glycol | 200 ml |

Example 174

Formulation of (+)-N-Hexyl-4-(3-methanesulfonylaminophenyl)-trans3,4-dimethylpiperidine A composition suitable for oral gavage administration is as follows:

| | |
|---|---|
| (+)-N-Hexyl-4-(3-methanesulfonylaminophenyl)-trans-3,4-dimethylpiperidine hydrochloride salt (Example 5a) | 440 mg |
| Sesame oil | 400 ml |

Example 175

Formulation of (±)-N-Hexyl-4-(3-methanesulfonylaminophenyl)-trans-3,4-dimethylpiperidine A composition suitable for oral capsule administration is as follows:

| | |
|---|---|
| (±)-N-Hexyl-4-(3-methanesulfonylaminophenyl)-trans-3,4-dimethylpiperidine hydrochloride salt (Example 4) | 0.0966 g |
| Glycerol | 1.9030 g |

A suspension of (±)-N-Hexyl-4-(3-methanesulfonylaminophenyl)-trans-3,4-dimethylpiperidine hydrochloride salt (Example 4) in glycerol was sonicated for approximately 40 min at 35° C. until a clear, yellow solution was obtained. The solution was placed in a hard gelatin capsule shell, size 2, and the capsule lid was placed on the capsule body and sealed tight.

Example 176

Formulation of (±)-N-Hexyl-4-(3-methanesulfonylaminophenyl)-trans-3,4-dimethylpiperidine A composition suitable for parenteral administration is as follows:

| | |
|---|---|
| (±)-N-Hexyl-4-(3-methanesulfonylaminophenyl)-trans-3,4-dimethylpiperidine hydrochloride salt (Example 4) | 132 mg |

| | |
|---|---|
| -continued | |
| Dimethylsulfoxide | 5.4 ml |
| Water | 114.6 ml |

Example 177

Formulation of (±)-N-Hexyl-4-(3-methanesulfonylaminophenyl)-trans-3,4-dimethylpiperidine A composition suitable for parenteral administration is as follows:

| | |
|---|---|
| (±)-N-Hexyl-4-(3-methanesulfonylaminophenyl)-trans-3,4-dimethylpiperidine hydrochloride salt (Example 4) | 4.93 mg |
| 0.9% w: v Aqueous sodium chloride solution | 4.49 ml |

PREPARATIONS

Preparation 1

(±)-N-Hexyl-4-(3-hydroxyphenyl)-trans-3,4-dimethylpiperidine

To a stirred solution of (±)-4-(3-hydroxyphenyl)-trans-3,4-dimethylpiperidine (J. A. Werner et al, J. Org. Chem., 1996, 61, 587), (2.0 g, 9.8 mmol) in N,N-dimethylformamide (50 ml) was added sodium hydrogen carbonate (1.76 g, 20.95 mmol) and bromohexane (1.64 g, 9.9 mmol). The reaction mixture was heated under reflux for 3 h and then cooled to room temperature. The reaction mixture was diluted with water (100 ml) and extracted with dichloromethane (4×50 ml). The combined extracts were washed with brine (100 ml), dried (MgSO$_4$), filtered and concentrated in vacuo to give the crude product. This was purified by silica (50 g) column chromatography eluting with ethyl acetate:hexane:0.880 ammonia (30:70:1) to give the title compound as a light brown oil (2.68 g, 91%).

NMR (CDCl$_3$, selected data for the free base): 0.75 (d, 3H), 0.85 (t, 3H), 1.15–1.25 (m, 6H), 1.3 (s, 3H), 2.0 (m, 1H), 2.35 (m, 4H), 2.6 (m, 2H), 6.55–7.2 (m, 4H).

MS (thermospray): M/Z [MH$^+$] 290.2; C$_{19}$H$_{31}$NO+H requires 290.2.

Preparation 2

(±)-4-(3-(1-Carbamoyl-1-methylethoxy)phenyl)-N-hexyl-trans-3,4-dimethylpiperidine To a solution of (±)-N-hexyl-4-(3-hydroxyphenyl)-trans-3,4-dimethylpiperidine (Preparation 1, 20 g, 69.2 mmol) in 1,4-dioxan (250 ml) under an atmosphere of nitrogen was added caesium carbonate (32.5 g, 100 mmol) carefully followed by sodium hydride (60% dispersion in mineral oil, 4 g, 100 mmol) in four portions over 30 min. The resultant mixture was stirred for 30 min then 2-bromo-2-methyl-propionamide (I. G. C. Coutts and M. R. Southcott, J. Chem. Soc., Perkin 1, 1990, 767–771), (16.6 g, 100 mmol) was added and the mixture was heated under reflux overnight. The reaction mixture was cooled, filtered and concentrated in vacuo to give the crude product which was purified by silica (600 g) column chromatography, eluting with a gradient of ethyl acetate:hexane:0.880 ammonia (30:70:1 to 50:50:1) to give recovered starting phenol (5.9 g, 30%) followed by the title compound as a white solid (14.3 g, 55%).

NMR (CDCl$_3$, selected data for the free base): 0.75 (d, 3H), 0.85 (m, 3H), 2.0 (m, 1H), 2.3 (m, 4H), 2.5 (m, 2H), 2.8 (m, 1H), 5.45 (br. s, 1H), 6.65 (br. s, 1H), 6.75–7.2 (m, 4H).

MS (thermospray): M/Z [MH$^+$] 375.4; C$_{23}$H$_{38}$N$_2$O$_2$+H requires 375.3.

Preparation 3

(±)-N-Hexyl-trans-3,4-dimethyl-4-(3-trifluoromethanesulfonyloxyphenyl)piperidine To a solution of (±)-N-hexyl-4-(3-hydroxyphenyl)-trans-3,4-dimethylpiperidine (Preparation 1, 3.5 g, 12 mmol) in dichloromethane (15 ml) under nitrogen was added triethylamine (3 ml) and N-phenylbis(trifluoromethanesulfonimide) (6.1 g, 18 mmol). The mixture was stirred for 18 h at room temperature and then 2N aqueous sodium hydroxide solution (60 ml) was added. The two layers were separated and the aqueous layer was extracted with dichloromethane (2×30 ml). The combined extracts were dried (Na$_2$SO$_4$), filtered and concentrated in vacuo to give the crude product. This was purified by silica (150 g) column chromatography eluting with ethyl acetate::hexane:0.88 ammonia (33:66:1) to give the title compound as a yellow oil (4.22 g, 83%).

NMR (CDCl$_3$, selected data for the free base): 0.75 (d, 3H), 0.9 (m, 3H), 1.2–1.4 (m, 9H), 1.4–1.7 (m, 3H), 2.0 (m, 1H), 2.2–2.45 (m, 4H), 2.45–2.65 (m, 2H), 2.8 (m, 1H), 7.1 (d, 1H), 7.15 (s, 1H), 7.25–7.45 (m, 2H).

MS (thermospray): M/Z [MH$^+$] 422.3; C$_{20}$H$_{30}$F$_3$NO$_3$S+H requires 422.2.

Preparation 4

(±)-N-Hexyl-trans-3,4-dimethyl-4-(3-N-diphenylmethylideneaminophenyl)piperidine

To a solution of (±)-N-hexyl-trans-3,4-dimethyl-4-(3-trifluoromethanesulfonyloxyphenyl)piperidine (Preparation 3, 4.5 g, 10.66 mmol) in deoxygenated tetrahydrofuran (150 ml) at room temperature was added caesium carbonate (5.0 g, 15.4 mmol), palladium (II) acetate (74 mg, 0.33 mmol), 2,2-bis(diphenylphosphino)-1-1'-binaphthyl (311 mg, 0.5 mmol) and benzophenone imine (2.4 g, 2.22 ml, 13.25 mmol). The mixture was heated under reflux for 80 h, cooled and the solid was removed by filtration washing with diethyl ether. The filtrate was concentrated in vacuo to give the crude product. The residue was taken up in dichloromethane (150 ml) and washed with 1N aqueous hydrochloric acid (100, 50 ml). The organic layer was stirred with 1N aqueous sodium hydroxide solution for 15 min, and then the two layers were separated. The organic layer was dried (MgSO$_4$), filtered and concentrated in vacuo to give the title compound as a crude deep red oil (5.0 g) which was used without further purification.

NMR (CDCl$_3$, selected data for the free base): 0.55 (d, 3H), 0.9 (m, 3H), 1.15 (s, 3H), 1.7–1.9 (m, 2H), 2.7 (m, 1H), 6.55–6.65 (m, 2H), 6.8 (m, 1H), 7.1–7.8 (m, 11H).

Preparation 5

(±)-4-(3-Aminophenyl)-N-hexyl-trans-3,4-dimethylpiperidine

Method A: A solution of (±)-N-hexyl-4-(3-(2-hydroxy-2-methylpropanoylamino)phenyl)-trans-3,4-dimethylpiperidine (Example 1, 12.9 g, 34.3 mmol) in 1,4-dioxan:5N aqueous hydrochloric acid (1:1, 150 ml) was heated under reflux overnight. The reaction mixture was cooled, diluted with water (100 ml) and extracted with diethyl ether (3×200 ml). The pH of the aqueous layer was adjusted to 8–9 using 5N aqueous sodium hydroxide solution, and extracted with dichloromethane (5×200 ml). The combined extracts were washed with brine (100 ml), dried ($Na_2SO_4$) and concentrated in vacuo to give the crude product which was purified by silica (200 g) column chromatography, eluting with ethyl acetate:hexane:0.880 ammonia (40:60:1), to afford the title compound as a clear oil (8.8 g, 89%).

Method B: To a solution of crude (±)-N-hexyl-trans-3,4-dimethyl-4-(3-N-diphenylmethylideneaminophenyl)piperidine (Preparation 4, 5.0 g) in tetrahydrofuran (40 ml) was added 2N aqueous hydrochloric acid (10 ml) and the mixture was stirred at room temperature for 1 h. The mixture was diluted with 2N aqueous hydrochloric acid (40 ml), hexane (50 ml) was added and the mixture was stirred vigorously for 10 min. The layers were separated and the aqueous phase was basified to pH 9 with 10 N aqueous sodium hydroxide solution. The basic aqueous layer was extracted with dichloromethane (100, 50 ml), and the combined extracts were washed with water (50 ml), dried ($Na_2SO_4$), filtered and concentrated in vacuo to give the title compound which was used without further purification (3.3 g, 90% crude yield over two steps).

NMR ($CDCl_3$, selected data for the free base): 0.8 (d, 3H), 0.9 (m, 3H), 1.95 (m, 1H), 2.35 (m, 4H), 2.55 (m, 2H), 2.8 (m, 1H), 3.6 (s, 2H), 6.5–7.1 (m, 4H).

MS (thermospray): M/Z [MH$^+$] 289.5; $C_{19}H_{32}N_2$+H requires 289.3.

Preparation 6 n-Heptanesulfonyl Chloride

To phosphorous pentachloride (3.3 g, 16 mmol) was added solid heptanesulfonic acid, sodium salt monohydrate (1.75 g, 8 mmol) and the mixture was left to stir overnight under nitrogen. Phosphorous oxychloride was removed by distillation at 150° C. for 3 h. The residue was distilled under reduced pressure (ca. 5 mm Hg) at 135° C. to give ca. 1 g of material which was allowed to cool to room temperature. The precipitated free acid was removed by filtration to afford the title compound as an oil (500 mg, 31%) which was used without further purification.

NMR ($CDCl_3$, selected data): 0.90 (t, 3H), 2.05 (m, 2H), 3.65 (t, 2H).

Preparation 7

(±)-N-Benzyl-4-(3-hydroxyphenyl)-trans-3,4-dimethylpiperidine

To a stirred solution of (±)-4-(3-hydroxyphenyl)-trans-3,4-dimethylpiperidine (J. A. Werner et al, J. Org. Chem., 1996, 61, 587), (2.08 g, 10.15 mmol) in N,N-dimethylformamide (50 ml) was added sodium hydrogen carbonate (1.70 g, 20.3 mmol) and benzyl bromide (1.35 ml, 11.2 mmol). The reaction mixture was heated under reflux for 1 h 30 min. The reaction mixture was then diluted with water (75 ml) and extracted with dichloromethane (100, 50, 25 ml). The combined extracts were dried ($Na_2SO_4$), filtered and concentrated in vacuo to give the crude product. This was purified by silica (70 g) column chromatography eluting with ethyl acetate:hexane:0.880 ammonia (30:70:1) to give the title compound as a pale pink oil (2.66 g, 89%).

NMR ($CDCl_3$, selected data for the free base): 0.8 (d, 3H), 1.2 (s, 3H), 2.9 (d, 1H), 3.5 (d, 1H), 3.6 (d, 1H), 6.6–6.9 (m, 3H), 7.1–7.4 (m, 6H).

MS (thermospray): M/Z [MH$^+$] 296.4; $C_{20}H_{25}NO$+H requires 296.2.

Preparation 8

(±)-N-Benzyl-4-(3-(1-carbamoyl-1-methylethoxy)phenyl)-trans-3,4-dimethylpiperidine To a solution of (±)-N-benzyl-4-(3-hydroxyphenyl)-trans-3,4-dimethylpiperidine (Preparation 7, 12.57 g, 42.6 mmol) in 1,4-dioxan (250 ml) under an atmosphere of nitrogen was added caesium carbonate (49.5 g, 152 mmol) carefully followed by anhydrous sodium hydride (4 g, 168 mmol) in four portions over 30 min. The resultant mixture was stirred for 1 h then 2-bromo-2-methylpropionamide (I. G. C. Coutts and M. R. Southcott, J. Chem. Soc., Perkin 1, 1990, 767–771), (20.5 g, 124 mmol) was added and the mixture was heated under reflux overnight. The reaction mixture was cooled, filtered and concentrated in vacuo to give the crude product which was purified by silica (600 g) column chromatography, eluting with a gradient of ethyl acetate:hexane:0.880 ammonia (25:75:1 to 100:0:1) to give recovered starting phenol (1.44 g, 11%) followed by the title compound as a clear oil (12.8 g, 79%).

NMR ($CDCl_3$, selected data for the free base): 0.8 (d, 3H), 1.35 (s, 3H), 1.95 (m, 1H), 2.35 (m, 2H), 2.55 (m, 2H), 2.8 (m, 1H), 3.5 (m, 2H), 5.4 (br. s, 1H), 6.65 (br. s, 1H), 6.75–7.4 (m, 9H).

MS (thermospray): M/Z [MH$^+$] 381.2; $C_{24}H_{32}N_2O_2$+H requires 381.3.

Preparation 9

(±)-4-(3-Aminophenyl)-N-benzyl-trans-3,4-dimethylpiperidine

A solution of (±)-N-benzyl-4-(3-(2-hydroxy-2-methylpropanoylamino)phenyl)-trans-3,4-dimethylpiperidine (Example 42, 10.1 g, 26.5 mmol) in 1,4-dioxan:5N aqueous hydrochloric acid (1:1, 200 ml) was heated under reflux overnight. The reaction mixture was cooled and basified to pH 13 with 10 N aqueous sodium hydroxide solution. It was then diluted with water (300 ml) and extracted with diethyl ether (3×300 ml). The combined extracts were washed with water (300 ml) and brine (300 ml), dried ($Na_2SO_4$) and concentrated in vacuo to give a brown oil which was purified by silica (400 g) column chromatography, eluting with ethyl acetate:hexane:0.880 ammonia (25:75:1) to give the title compound as a golden oil (7.6 g, 96%).

NMR ($CDCl_3$, selected data for the free base): 0.8 (d, 3H), 1.3 (s, 3H), 1.55 (m, 1H), 1.95 (m, 1H), 2.25–2.6 (m, 4H), 2.85 (m, 1H), 3.4–3.7 (m, 2H), 6.45–7.4 (m, 9H).

MS (thermospray): M/Z [MH$^+$] 295.3; $C_{20}H_{26}N_2$+H requires 295.2.

Preparation 10

(±)-4-(3-Methanesulfonylaminophenyl)-trans-3,4-dimethylpiperidine

To a solution of (±)-N-benzyl-4-(3-methanesulfonylaminophenyl)-trans-3,4-dimethylpiperidine (Example 43, 6.63 g, 17.8 mmol) in methanol (150 ml) was added 10% debenzylation catalyst (Degussa type E101, 1.0 g). The reaction mixture was placed under an atmosphere of hydrogen and left overnight. The reaction mixture was filtered through a pad of Celite™ and concentrated in vacuo to give the title compound as an off-white foam (5.05 g, 100%).

NMR (CD$_3$OD, selected data for the free base): 0.7 (d, 3H), 1.55 (m, 1H), 2.7 (d, 1H), 2.95 (m, 5H), 3.2 (d, 1H), 7.0–7.3 (m, 4H).

MS (thermospray): M/Z [MH$^+$] 283.2; C$_{14}$H$_{22}$N$_2$O$_2$S+H requires 283.1.

Preparation 11

3-Cyclopentylpropyl 4-bromobenzenesulfonate

To a solution of 3-cyclopentyl-1-propanol (2.0 g, 15.6 mmol) in triethylamine (3.25 ml, 23.4 mmol) and dichloromethane (50 ml) was added 4-bromobenzenesulfonyl chloride (4.4 g, 17.6 mmol). The solution was stirred for 16 h, diluted with 2 N aqueous hydrochloric acid (100 ml) and extracted with dichloromethane (100 ml). The extract was washed with saturated aqueous sodium hydrogen carbonate solution (100 ml) and brine (100 ml), dried (MgSO$_4$) and concentrated in vacuo to give the title compound as a white crystalline solid (4.50 g, 80%).

NMR (CDCl$_3$): 1.0–1.8 (m, 13H), 4.05 (t, 2H), 7.65 (d, 2H), 7.8 (d, 2H).

Preparation 12

3-Cyclopentyl-1-iodopropane

To a solution of 3-cyclopentylpropyl 4-bromobenzenesulfonate (Preparation 12, 1.0 g, 2.85 mmol) in acetone (30 ml) was added sodium iodide (1.0 g, 6.67 mmol) and the reaction mixture was left to stir at room temperature for 16 h. The resulting precipitate was filtered and the filtrate was diluted with water (100 ml) and extracted with dichloromethane (100 ml). The extract was washed with brine (100 ml), dried (MgSO$_4$) and concentrated in vacuo to give the title compound as a light pink oil (0.60 g, 90%).

NMR (CDCl$_3$): 1.0–1.8 (m, 11H), 1.8 (t, 2H), 3.1 (t, 2H).

Preparation 13

Ethyl 2-(4,4-dimethyl-2-cyclohexen-1-ylidene)acetate

To a suspension of sodium hydride (60% dispersion in oil, 2.2 g, 55 mmol) in tetrahydrofuran (100 ml) at 0° C. was added ethyl 2-(diethoxyphosphoryl)acetate (11.2 g, 50 mmol) over 30 min, and the mixture was stirred at room temperature for 1 h. To this was added 4,4-dimethyl-2-cyclohexene-1-one over 20 min and the reaction mixture was stirred for a further 1 h. Water (100 ml) was added and the mixture was extracted with ether (2×100 ml). The combined extracts were dried (MgSO$_4$), filtered and concentrated in vacuo to afford the title compound as a colourless oil (9.7 g, 100%).

NMR (CDCl$_3$, selected data): 1.0 (s, 6H), 1.1 (t, 3H), 1.4–1.6 (m, 2H), 2.35 (t, 1H), 2.95 (t, 1H), 4.1 (q, 2H), 5.4 (s, 1H), 5.85 (d, 1H), 7.25 (d, 1H).

Preparation 14

Ethyl 2-(4,4-dimethylcyclohexyl)acetate

A solution of ethyl 2-(4,4-dimethyl-2-cyclohexene-1-ylidene)acetate (Preparation 13, 4.0 g, 21 mmol) in methanol (40 ml) was treated with 5% palladium on carbon, and the suspension was placed under an atmosphere of hydrogen (60 p.s.i.) at room temperature for 48 h. The mixture was filtered through a short pad of silica (40 g) and the filtrate was concentrated in vacuo to afford the title compound as a colourless oil (3.7 g, 91%).

NMR (CDCl$_3$, selected data) 0.9 (s, 3H), 0.95 (s, 3H), 1.1–1.55 (m, 11H), 1.65 (m, 1H), 2.1 (d, 2H), 4.1 (q, 2H).

Preparation 15

2-(4,4-Dimethylcyclohexyl)-1-ethanol

To a solution of ethyl 2-(4,4-dimethylcyclohexyl)acetate (Preparation 14, 2.0 g, 10 mmol) in tetrahydrofuran (20 ml) under an atmosphere of nitrogen at 0° C. was added lithium aluminium hydride (1.0M solution in tetrahydrofuran, 11 ml, 11 mmol) and the reaction mixture was allowed to warm to room temperature overnight. The mixture was poured onto ice (300 g), acidified to pH 1 with 1N aqueous hydrochloric acid and extracted with dichloromethane (200 ml). The organic extract was dried (MgSO$_4$), filtered and concentrated in vacuo to afford the title compound as a pale yellow oil (1.45 g, 93%).

NMR (CDCl$_3$, selected data): 0.9 (s, 3H), 0.95 (s, 3H), 1.0–1.65 (m, 11H), 3.75 (m, 3H).

Preparation 16

2-(4,4-Dimethylcyclohexyl)ethyl 4-bromobenzenesulfonate

To a solution of 2-(4,4-dimethylcyclohexyl)-1-ethanol (Preparation 15, 1.45 g, 9 mmol) and 4-bromobenzenesulfonyl chloride (2.53 g, 10 mmol) in dichloromethane (30 ml) was added triethylamine (1.9 ml, 13.5 mmol), and the reaction mixture was allowed to stir at room temperature for 24 h. After a further addition of 4-bromobenzenesulfonyl chloride (2.53 g, 10 mmol) and triethylamine (1.9 ml, 13.5 mmol), the reaction mixture was heated under reflux for 1 h. After allowing the reaction mixture to cool to room temperature, the mixture was treated with 2N aqueous hydrochloric acid (100 ml) and the phases were separated. The organic extract was dried (MgSO$_4$), filtered and concentrated in vacuo to afford the crude product. The residue was purified by silica (80 g) column chromatography eluting with diethyl ether:hexane (1:20) to give the title compound as a colourless oil (450 mg, 13%).

NMR (CDCl$_3$, selected data): 0.85 (s, 3H), 0.95 (s, 3H), 1.0–1.6 (m, 11H), 4.05 (m, 3H), 7.65 (d, 2H), 7.75 (d, 2H).

Preparation 17

4-(2-Iodoethyl)-1,1-dimethylcyclohexane

To a solution of 2-(4,4-dimethylcyclohexyl)ethyl 4-bromobenzenesulfonate (Preparation 16, 410 mg, 1 mmol) in acetone (100 ml) was added sodium iodide (370 mg, 2.5 mmol), and the mixture was heated under reflux for 3 h. After allowing the reaction mixture to cool to room temperature, the mixture was filtered and the filtrate was diluted with water (500 ml) and extracted with diethyl ether (500 ml). The organic extract was dried (MgSO$_4$), filtered and concentrated in vacuo to afford the title compound as a colourless oil (220 mg, 83%).

NMR (CDCl$_3$, selected data): 0.9 (s, 3H), 0.95 (s, 3H), 1.0–1.6 (m, 9H), 1.75 (m, 2H), 3.2 (m, 2H).

Preparation 18

2-Cyclohexyloxyethyl 4-bromobenzenesulfonate

To a solution of 2-cyclohexyloxy-1-propanol (4.0 g, 28 mmol) in triethylamine (5.8 ml) and dichloromethane (250 ml) was added 4-bromobenzenesulfonyl chloride (7.87 g, 31 mmol) at 0° C. under nitrogen, and the resultant mixture was stirred for 16 h at room temperature. The reaction mixture was washed with saturated aqueous sodium hydrogen carbonate solution, water and brine (100 ml each), dried ($MgSO_4$) and concentrated in vacuo to give the crude product. This was purified by silica (200 g) column chromatography using a gradient elution of hexane:ethyl acetate (6:1 to 1:1) to give the title compound as a white crystalline solid (8.0 g, 80% yield).

NMR ($CDCl_3$): 1.1–1.8 (m, 14H), 3.2 (m, 2H), 3.65 (t, 2H), 4.15 (t, 2H), 7.6–7.9 (m, 4H).

MS (thermospray): M/Z [MH$^+$] 362.9; $C_{14}H_{19}BrO_4S$+H requires 363.0.

Preparation 19

2-Cyclohexyloxy-1-iodoethane

To a solution of 2-cyclohexyloxyethyl 4-bromobenzenesulfonate (Preparation 18, 120 mg, 0.3 mmol) in acetone (5 ml) was added sodium iodide (90 mg, 0.6 mmol) and the reaction mixture was left to stir at room temperature for 18 h. A further equivalent of sodium iodide was added and the reaction mixture was stirred at room temperature for a further 18 h after which time the reaction mixture was heated to 80° C. for 5 h. The resulting precipitate was filtered and the filtrate was diluted with water (100 ml) and extracted with dichloromethane (100 ml). The extract was washed with brine (100 ml), dried ($MgSO_4$) and concentrated in vacuo to give the title compound as a colourless oil (50 mg, 60%).

NMR ($CDCl_3$): 1.1–1.9 (m, 11H), 3.1 (t, 2H), 3.7 (t, 2H).

Preparation 20

3-Ethyl-1-vinylbenzene

To a solution of 1-bromo-3-ethylbenzene (2.0 g, 10.8 mmol) in deoxygenated N,N-dimethylformamide (50 ml) under nitrogen was added tributylvinyltin (5.0 g, 16.2 mmol) and tetrakistriphenylphosphine palladium (0) (500 mg, 4 mol %) and the reaction mixture was heated to 75° C. for 7 h. The cooled reaction mixture was poured onto water (400 ml) and extracted with diethyl ether (5×200 ml). The combined extracts were dried ($MgSO_4$), filtered and concentrated in vacuo to afford the crude product. This was distilled under reduced pressure to afford a residue that was partitioned between water and hexane. The layers were separated and the aqueous layer was extracted with hexane. The combined extracts were dried ($MgSO_4$), filtered and concentrated in vacuo to afford the title compound as a colourless oil (1.4 g, 98%).

NMR ($CDCl_3$): 1.25 (m, 3H), 2.65 (m, 2H), 5.2 (d, 1H), 5.75 (d, 1H), 6.75 (m, 1H), 7.1–7.3 (m, 4H).

Preparation 21

1-(2-Bromoethyl)-3-ethylbenzene

To a solution of 3-ethyl-1-vinylbenzene (Preparation 20, 1.45 g, 10.9 mmol) in anhydrous tetrahydrofuran (50 ml) under nitrogen at 0° C. was added diborane (1.0M solution in tetrahydrofuran, 4 ml, 4 mmol) dropwise over 30 min. After 30 min at room temperature, methanol (0.1 ml) was added to destroy excess diborane. The reaction mixture was cooled to 0° C., and bromine (0.59 ml, 11 mmol) and a solution of sodium methoxide in methanol (12.1 mmol) were added via separate syringes at such a rate that a pale yellow coloration was always maintained. The reaction mixture was partitioned between aqueous saturated potassium carbonate solution and hexane. The layers were separated and the aqueous layer was extracted with dichloromethane. The combined extracts were dried ($MgSO_4$), filtered and concentrated in vacuo to afford the crude product. The residue was purified by silica column chromatography eluting with hexane to afford the title compound (640 mg, 28%).

NMR ($CDCl_3$): 1.25 (m, 3H), 2.65 (m, 2H), 3.15 (t, 2H), 3.6 (t, 2H), 7.0–7.4 (m, 4H).

Preparation 22

3-Methoxyphenethyl 4-bromobenzenesulfonate

To a solution of 3-methoxyphenylethanol (1.6 g, 10.5 mmol) and 4-bromobenzenesulfonyl chloride (2.81 g, 11 mmol) in dichloromethane (20 ml) was added triethylamine (2.0 ml, 15 mmol), and the reaction mixture was allowed to stir at room temperature for 48 h. The reaction mixture was treated with 1N aqueous hydrochloric acid (5 ml) and the phases were separated. The organic extract was dried ($MgSO_4$), filtered and concentrated in vacuo to afford 2.8 g of crude product. A portion of the residue (200 mg) was purified by silica (5 g) column chromatography eluting with dichloromethane:hexane (2:1) to afford the title compound as a colourless oil (100 mg, 33% based on material taken through).

NMR ($CDCl_3$, selected data): 2.95 (t, 2H), 3.75 (s, 3H), 4.15 (t, 2H), 6.6 (s, 1H), 6.8 (d, 1H), 7.15 (m, 1H), 7.6 (m, 4H).

Preparation 23

3-(Trifluoromethyl)phenethyl 4-bromobenzenesulfonate

To a solution of 3-trifluoromethylphenylethanol (2.0 g, 10.5 mmol) and 4-bromobenzenesulfonyl chloride (2.81 g, 11 mmol) in dichloromethane (20 ml) was added triethylamine (2.0 ml, 15 mmol), and the reaction mixture was allowed to stir at room temperature for 48 h. The reaction mixture was treated with 1N aqueous hydrochloric acid (5 ml) and the phases were separated. The organic extract was dried ($MgSO_4$), filtered and concentrated in vacuo to afford 3.6 g of crude product. A portion of the residue (200 mg) was purified by silica (5 g) column chromatography eluting with dichloromethane:hexane (2:1) to afford the title compound as a colourless oil (130 mg, 54% based on material taken through).

NMR ($CDCl_3$, selected data): 3.05 (t, 2H), 4.15 (t, 2H), 7.2–7.4 (m, 3H), 7.5 (d, 1H), 7.6 (m, 4H).

Preparation 24

1-Naphthylethyl 4-bromobenzenesulfonate

To a solution of 1-naphthylethanol (2.0 g, 12 mmol) and 4-bromobenzenesulfonyl chloride (4.45 g, 17 mmol) in dichloromethane (50 ml) was added triethylamine (2.43 ml, 17 mmol), and the mixture was allowed to stir at room temperature for 48 h. The reaction mixture was treated with 2N aqueous hydrochloric acid (100 ml) and the phases were separated. The organic extract was dried ($MgSO_4$), filtered and concentrated in vacuo to afford 6.62 g of crude product. The residue was purified by silica (400 g) column chromatography eluting with dichloromethane:hexane (2:1) to afford the title compound as a colourless oil (3.1 g, 69%).

NMR (CDCl$_3$, selected data): 3.45 (t, 2H), 4.45 (t, 2H), 7.2–7.5 (m, 8H), 7.7–7.9 (m, 3H).

Preparation 25

Methyl 3-(tetrahydropyran-2-yl)propenoate

A mixture of methyl (E)- and (Z)-3-(tetrahydropyran-2-yl)-2-propenoate (H. Priepke and R. Brückner, Chem. Ber., 1990, 123, 153), (537 mg, 3.15 mmol) was dissolved in methanol (10 ml) containing 10% palladium on charcoal (50 mg) and placed under an atmosphere of hydrogen (50 psi) at room temperature overnight. The reaction mixture was filtered through Celite™, the residue was washed with methanol and the combined filtrates were concentrated in vacuo. The crude product was purified by silica (30 g) column chromatography eluting with diethyl ether:hexane (1:4) to give the title compound as a colourless oil (470 mg, 87%).

NMR (CDCl$_3$): 1.2 (q, 1H), 1.5–1.6 (m, 4H), 1.7–1.8 (m, 3H), 2.4 (m, 2H), 3.2 (m, 1H), 3.35 (t, 1H), 3.6 (s, 3H), 3.9 (d, 1H).

Preparation 26

3-(Tetrahydropyran-2-yl)propanoic Acid

A 2M aqueous solution of lithium hydroxide (4 ml) was added to a solution of methyl 3-(tetrahydropyran-2-yl)propanoate (Preparation 25, 460 mg, 2.67 mmol) in tetrahydrofuran (16 ml) and the reaction mixture was heated under reflux for 10 h. The cooled reaction mixture was acidified with 2N aqueous hydrochloric acid to pH 1 and extracted with ethyl acetate (3×50 ml). The combined extracts were washed with brine (30 ml), dried (MgSO$_4$), filtered and concentrated in vacuo to give the title compound as a colourless oil (460 mg, 67%).

NMR (CDCl$_3$): 1.15 (m, 1H), 1.4–1.6 (m, 4H), 1.7–1.9 (m, 3H), 2.5 (m, 2H), 3.25 (m, 1H), 3.4 (m, 1H), 3.95 (d, 1H).

MS (thermospray): M/Z [MH$^+$] 159.2; C$_8$H$_{14}$O$_3$+H requires 159.1.

Preparation 27

(±)-4-(3-Methanesulfonylaminophenyl)-trans-3,4-dimethyl-N-(3-(tetrahydropyran-2-yl)propanoyl) piperidine A mixture of 3-(tetrahydropyran-2-yl)propanoic acid (Preparation 26, 79 mg, 0.5 mmol), 1-hydroxybenzotriazole hydrate (72 mg, 0.53 mmol) and 1-(3-dimethylaminopropyl)-3-ethylcarbodiimide hydrochloride (136 mg, 0.71 mmol) was dissolved in N,N-dimethylformamide (10 ml) and stirred at room temperature for 5 min. To this was added (±)-4-(3-methanesulfonylaminophenyl)-trans-3,4-dimethylpiperidine (Preparation 10, 150 mg, 0.53 mmol) in one portion and the reaction mixture was stirred overnight at room temperature. This was diluted with water (10 ml) and extracted with diethyl ether (3×20 ml). The combined extracts were washed with water (15 ml) and brine (15 ml), dried (Na$_2$SO$_4$) and concentrated in vacuo to give a clear oil which was purified by silica (9 g) column chromatography eluting with dichloromethane:ethanol:0.880 ammonia (300:8:1) to give the title compound as a clear viscous oil (157 mg, 74%).

NMR (CDCl$_3$): 0.6 (m, 3H), 1.4 (s, 3H), 3.0 (s, 3H), 3.05–3.7 (m, 4H), 7.0–7.35 (m, 4H).

MS (APCI): M/Z [MH$^+$] 423.4; C$_{22}$H$_{34}$N$_2$O$_4$S+H requires 423.2.

Preparation 28

2-Adamantylethyl 4-bromobenzenesulfonate

To a solution of 1-adamantylethanol (5.8 g, 32 mmol) in triethylamine (6.7 ml) and dichloromethane (50 ml) was added 4-bromobenzenesulphonyl chloride (8.9 g, 35 mmol) at room temperature. The solution was stirred for 16 h, diluted with 2N aqueous hydrochloric acid (100 ml) and extracted with dichloromethane (100 ml). The extract was washed with saturated aqueous sodium hydrogen carbonate solution (100 ml) and brine (100 ml), dried (MgSO$_4$), and concentrated in vacuo to give the title compound as a white crystalline solid (11.2 g, 88%).

NMR (CDCl$_3$): 1.4–1.6 (m, 11H), 1.65 (d, 3H), 2.0 (2, 3H), 4.1 (t, 2H), 7.6–7.8 (m, 4H).

MS (thermospray): M/Z [MH$^+$] 416.3; C$_{18}$H$_{23}$BrO$_3$S+NH$_4$ requires 416.1.

Preparation 29

1-Adamantyl-2-iodoethane

To a solution of 2-adamantylethyl 4-bromobenzenesulfonate (Preparation 28, 1.0 g, 2.5 mmol) in acetone (25 ml) was added sodium iodide (0.75 g, 5 mmol) and the reaction mixture was left to stir at room temperature for 72 h. The resulting precipitate was filtered and the filtrate was diluted with water (100 ml) and extracted with dichloromethane (100 ml). The extract was washed with brine (100 ml), dried (MgSO$_4$) and concentrated in vacuo to give the title compound as a white crystalline solid (0.54 g, 75%).

NMR (CDCl$_3$): 1.4–1.8 (m, 15H), 1.95 (t, 2H), 3.1 (t, 2H).

Preparation 30

(E)-1-Bromo-3-cyclohexylprop-2-ene

To a stirred solution of (E)-3-cyclohexyl-2-propen-1-ol (A. G. M. Barrett et al, Tetrahedron, 1996, 52, 15325), (1.47 g, 10.5 mmol) in diethyl ether (20 ml) and pyridine (1 ml) was added phosphorus tribromide (1.40 ml, 15 mmol) dropwise at room temperature under an atmosphere of nitrogen. After 16 h, the reaction mixture was carefully poured onto ice water (100 ml) and extracted with diethyl ether (100 ml). The extract was washed with saturated aqueous sodium hydrogen carbonate solution (100 ml), dried (MgSO$_4$) and concentrated in vacuo to give the crude product. This was purified by silica (20 g) column chromatography eluting with hexane:ethyl acetate (4:1) to give the title compound as a colourless oil (1.3 g, 61%).

NMR (CDCl$_3$): 0.8–1.4 (m, 6H), 1.6–1.8 (m, 4H), 2.0 (m, 1H), 3.95 (d, 2H), 5.6–5.8 (m, 2H).

MS (thermospray): M/Z [MH$^+$] 203.3; C$_9$H$_{15}$Br+H requires 203.0.

Preparation 31

3-Cyclohexyl-3-oxopropyl 4-bromobenzenesulfonate

To a solution of (S)-3-cyclohexyl-3-hydroxypropyl 4-bromobenzenesulfonate (J. A. Werner et al, J. Org. Chem., 1996, 61, 587), (40 mg, 0.106 mmol) in dichloromethane (3 ml) was added silica (50 mg) and pyridinium chlorochromate (20 mg, 0.09 mmol), and the reaction mixture was left to stir at room temperature for 16 h. The reaction mixture was subjected to direct silica (5 g) column chromatography eluting with dichloromethane:hexane (4:1) to afford the title compound as a yellow solid (38 mg, 96%).

NMR (CDCl$_3$): 1.1–1.9 (m, 10H), 2.3 (m, 1H), 2.85 (m, 2H), 4.3 (m, 2H), 7.7–7.85 (m, 4H).

Preparation 32

4-(Bromomethyl)benzamide

A solution of 4-(bromomethyl)benzonitrile (500 mg, 2.55 mmol) in 90% sulphuric acid (8 ml) was heated at 100° C. for 1 h. The solution was carefully poured onto ice water (50 ml) and a precipitate formed. The solid was filtered, washed with water and diethyl ether and dried in vacuo to afford the title compound as a white solid (353 mg, 65%).

NMR (CDCl$_3$): 4.55 (s, 2H), 5.6–6.2 (br. s, 2H), 7.65 (d, 2H), 7.85 (d, 2H).

Preparation 33

1-(2-Bromoethoxy)-2,3-dichlorobenzene

To a mixture of 2,3-dichlorophenol (20 g, 0.123 mol) and 1,2-dibromoethane (30.5 g, 0.162 mol) was added a sodium hydroxide solution (5 g, 0.125 mol in 125 ml of water), and the mixture was heated under reflux for 8 h. The mixture was allowed to cool and extracted with chloroform (2×100 ml). The combined extracts were washed with 1N aqueous sodium hydroxide solution (100 ml), dried, filtered and concentrated in vacuo. The residue was distilled at 106° C./0.3 mm of mercury to afford on cooling to room temperature the title compound as a yellow solid (20 g, 60%).

m.p. 51–56° C.

Preparation 34

2-(3-Bromopropoxy)-1,3-dichlorobenzene

A mixture of 2,6-dichlorophenol (163 g, 1 mol) and 1,3-dibromopropane (262 g, 1.3 mol) was heated to 100° C., and a solution of sodium hydroxide (40 g) in water (1000 ml) was added dropwise over 75 min. The mixture was heated under reflux for 5 h and then cooled to room temperature upon which a biphasic solution developed. The organic layer was separated and the aqueous layer was extracted with diethyl ether (3×250 ml). The combined organic fractions were washed with 2N aqueous sodium hydroxide solution (4×250 ml) and water (250 ml), dried (MgSO$_4$), filtered and concentrated in vacuo to afford the crude product. The residue was distilled at 100–120° C./0.3 mm of mercury to afford the title compound as an oil (202.5 g, 71%).

Preparation 35

2-(Bromomethyl)pyridine

A mixture of 2-(hydroxymethyl)pyridine (5.0 g, 46 mmol) and 48% aqueous hydrobromic acid (40 ml) was heated to 150° C. for 4 h. The mixture was concentrated in vacuo, dissolved in ethanol (100 ml) and cooled to −18° C. for 48 h. The precipitate was filtered to afford white crystals which were dissolved in 48% aqueous hydrobromic acid (40 ml) and heated under reflux for 24 h. The mixture was concentrated in vacuo, dissolved in ethanol (100 ml) and cooled to −18° C. for 48 h. The precipitate was filtered to afford the title compound as the hydrobromide salt (7.7 g, 66%)

m.p. 150–153° C.

Preparation 36

4-Bromo-N-methyl-3-oxo-N-phenylbutanamide

To a solution of N-methyl-3-oxo-N-phenylbutanamide (26.0 g, 0.136 mol) in carbon tetrachloride (200 ml) was added bromine (24.05 g, 0.15 mol) dropwise over 30 min, and the mixture was heated under reflux for 5 min. After allowing to cool to room temperature, the reaction mixture was concentrated in vacuo, triturated with diethyl ether and filtered to afford the title compound as a white solid (10.3 g, 28%).

Preparation 37

4-(Bromomethyl)-1-methyl-2(1H)-quinoline

A solution of 4-bromo-N-methyl-3-oxo-N-phenylbutanamide (Preparation 36, 3.0 g, 11.2 mmol) in concentrated sulphuric acid (10 ml) was stirred at room temperature for 24 h. The reaction mixture was diluted with water (100 ml) and the resulting precipitate was filtered, treated with water (100 ml) to form a suspension, neutralised to pH 7 with sodium bicarbonate and extracted with ethyl acetate. The extract was dried (MgSO$_4$), filtered and concentrated in vacuo to afford the title compound as a white solid (610 mg, 22%).

NMR (CDCl$_3$) 7.85 (1H, d), 7.60 (1H, t), 7.4 (1H, d), 7.35 (1H, t), 6.80 (1H, s), 4.60 (2H, s), 3.70 (3H, s).

Preparation 38

1-(2-Bromoethyl)-2,5-dimethyl-1H-pyrrole

To a solution of 2-bromoethylamine hydrobromide (20.5 g, 0.1 mol) and acetonylacetone (12.5 ml, 0.1 mol) in acetic acid (10 ml) was added potassium acetate (10 g, 0.1 mol), and the mixture was stirred for 1 h at 20° C. and for 2 h at 80° C. The reaction mixture was diluted with water (150 ml) and extracted with diethyl ether (150 ml). The extract was washed with brine and concentrated in vacuo to afford an oily residue. The residue was distilled at 60–64° C./0.5 mm of mercury to afford the title compound as a colourless oil (9.45 g, 47%).

Preparation 39

(±)4-(3-Ethanesulfonylaminophenyl)-trans-3,4-dimethylpiperidine

To a solution of (±)-N-benzyl-4-(3-ethanesulfonylaminophenyl)-trans-3,4-dimethylpiperidine (Example 142, 340 mg, 0.9 mmol) in methanol (15 ml) was added 10% debenzylation catalyst (200 mg) (Degussa type E101). The reaction mixture was placed under an atmosphere of hydrogen (40 p.s.i. at room temperature) for 2 d. The reaction mixture was filtered through Arbocel™, further 10% debenzylation catalyst (200 mg) (Degussa type E101) was added and the reaction mixture was placed under an atmosphere of hydrogen (40 p.s.i. at room temperature) for 2 d. The reaction mixture was filtered through Arbocel™ and concentrated in vacuo to give the title compound as a yellow oil which was used without further purification (263 mg, 98%).

NMR (CDCl$_3$, selected data for the free base): 0.75 (d, 3H), 1.2 (t, 3H), 1.75 (m, 1H), 2.95 (q, 2H), 6.9–7.25 (m, 4H).

MS (thermospray): M/Z [MH$^+$] 297.5; $C_{15}H_{24}N_2O_2S$+H requires 297.2.

Preparation 40

(±)-trans-3,4-Dimethyl-4-(3-n-propanesulfonylaminophenyl)piperidine

To a solution of (±)-N-benzyl-trans-3,4,dimethyl-4-(3-n-propanesulphonylaminophenyl)piperidine (Example 143, 500 mg, 1.25 mmol) in methanol (50 ml) was added 10% debenzylation catalyst (200 mg) (Degussa type E101). The reaction mixture was placed under hydrogen (60 psi at 60° C.) and left overnight. Further 10% debenzylation catalyst (200 mg) (Degussa type E101) was added to the reaction mixture which was placed under an atmosphere of hydrogen and left overnight. Further 10% debenzylation catalyst (200 mg) (Degussa type E101) was added to the reaction mixture which was placed under an atmosphere of hydrogen and left overnight. The reaction mixture was filtered through a pad of Arbocel™ and concentrated in vacuo to give the title compound as a yellow oil (390 mg, 100% crude yield).

MS (APCI): M/Z [MH$^+$] 311.4; $C_{16}H_{26}N_2O_2S$+H requires 311.2.

Preparation 41

(±)-trans-3-4-Dimethyl-4-(3-(1-methylimidazole-4-yl-sulfonylamino)phenyl)piperidine To a solution of (±)-N-benzyl-trans-3-4-dimethyl-(4-(3-(1-methylimidazole-4-yl-sulfonylamino)phenyl)piperidine (Example 144, 440 mg, 1 mmol) in methanol:dichloromethane (5:3, 80 ml) was added 10% debenzylation catalyst (200 mg) (Degussa type E101). The reaction mixture was placed under hydrogen (60 psi) at room temperature and left for 2 d. The reaction mixture was filtered through a pad of Celite™ and concentrated in vacuo to give the title compound as an off-white foam (348 mg, 100%).

NMR (CDCl$_3$, selected data for the free base): 0.7 (d, 3H), 1.35 (s, 3H), 3.6 (s, 3H), 6.9–7.2 (m, 4H), 7.35 (s, 1H), 7.6 (s, 1H).

MS (thermospray): M/Z [MH$^+$] 349.4; $C_{17}H_{24}N_4O_2S$+H requires 349.2.

Preparation 42

(±)-N-Hexyl-trans-3,4-dimethyl-4-(3-N-methaneaminophenyl)piperidine

To a stirred solution of (±)-4-(3-aminophenyl)-N-hexyl-trans-3,4-dimethylpiperidine (Preparation 5, 100 mg, 0.35 mmol) in triethylorthoformate (1 ml) at 0° C. was added trifluoroacetic acid (1 drop). The mixture was stirred at room temperature for 2 h, then it was concentrated in vacuo. The residual oil was dissolved in ethyl acetate (1 ml), cooled to 0° C. and sodium borohydride (80 mg, 2.16 mmol) was added. The mixture was stirred at room temperature overnight, then water (5 ml) was added and the mixture was extracted with dichloromethane (3×5 ml). The combined extracts were dried (Na$_2$SO$_4$), filtered and concentrated in vacuo to give the crude product which was purified by silica (5 g) column chromatography eluting with ethyl acetate:0.880 ammonia (99:1) to give the title compound as a colourless oil (70 mg, 66%).

MS (thermospray): M/Z [MH$^+$] 303.4; $C_{20}H_{34}N_2$+H requires 303.3.

Preparation 43

N-Ethyl-4-hydroxy-4-(3-(1-methylethoxy)phenyl)piperidine

To a stirred solution of 1-bromo-3-(1-methylethoxy)benzene (5.0 g, 23 mmol) in anhydrous tetrahydrofuran (50 ml) at –78° C. under an atmosphere of nitrogen was added n-butyllithium (1.6M in hexane, 13.7 ml, 22 mmol) dropwise. The reaction mixture was stirred for 1 h at –78° C., before N-ethyl-4-piperidone (2.95 ml, 22 mmol) was added dropwise at –78° C. over 15 minutes, and the reaction mixture was then warmed to –20° C. over 30 minutes. The solution was poured onto 2N aqueous hydrochloric acid (35 ml) and this was further acidified to pH 1 with concentrated hydrochloric acid. Hexane (50 ml) was added and the two layers were separated. The organic layer was discarded and the pH of the aqueous layer was adjusted to 14 using sodium hydroxide pellets. The basic aqueous layer was extracted with hexane:diethyl ether (1:1, 5×50 ml) and the combined extracts were dried (MgSO$_4$) and concentrated to give the title compound as a crude oil (4.2 g, 73% crude yield) which was used without further purification.

NMR (CDCl$_3$, selected data for the free base): 1.1 (t, 3H), 1.3 (d, 6H), 1.6 (s, 1H), 1.75 (d, 2H), 2.1–2.2 (m, 2H), 2.4–2.6 (m, 4H), 2.85 (m, 2H), 4.55 (m, 1H), 6.8–7.2 (m, 4H).

Preparation 44

N-Ethyl-1,2,3,6-tetrahydro-4-(3-(1-methylethoxy)phenyl)pyridine p-Toluenesulfonic acid (6.1 g, 31.9 mmoi) was added to a solution of N-ethyl-4-hydroxy-4-(3-(1-methylethoxy)phenyl)piperidine (Preparation 43, 4.2 g, 16.0 mmol) in toluene (50 ml), and the reaction mixture was heated under reflux for 3 h. The reaction mixture was allowed to cool to room temperature, water (20 ml) was added, and the resultant biphasic system was stirred vigorously for several minutes. The aqueous layer was basified with 2N aqueous sodium hydroxide solution (10 ml) and the two phases were separated. The aqueous layer was then further extracted with ether (3×10 ml) and the combined extracts were dried (MgSO$_4$), filtered and concentrated to give a crude oil which was purified by silica column chromatography eluting with ethyl acetate:methanol: 0.880 ammonia (96:3:1) to give the title compound as an oil (2.1 g, 54%).

NMR (CDCl$_3$, selected data for the free base): 1.15 (t, 3H), 1.3 (d, 6H), 2.45–2.7 (m, 6H), 3.15 (m, 2H), 4.55 (m, 1H), 6.05 (m, 1H), 6.75–7.1 (m, 4H).

Preparation 45

N-Ethyl-4-(3-(1-methylethoxy)phenyl)piperidine

N-Ethyl-1,2,3,6-tetrahydro-4-(3-(1-methylethoxy)phenyl)pyridine (Preparation 44, 2.0 g, 8.16 mmol) was dissolved in ethanol (20 ml) and 5% palladium on carbon (0.2 g) was added. The suspension was heated at 60° C. under hydrogen (20 psi) for 5 h. The mixture was cooled and the solid was removed by filtration through Arbocel™, washing the resultant cake with ethyl acetate. The filtrate was concentrated in vacuo to give the title compound as an oil (2.0 g, 99%) which was used without further purification.

NMR (CDCl$_3$, selected data for the free base): 1.1 (t, 3H), 1.3 (d, 6H), 1.65 (s, 1H), 1.7–2.1 (m, 6H), 2.45 (m, 3H), 3.1 (m, 2H), 4.5 (m, 1H), 6.7–7.2 (m, 4H).

Preparation 46

4-(3-(1-Methylethoxy)phenyl)-1-piperidinecarboxylic acid phenyl ester

To N-ethyl-4-(3-(1-methylethoxy)phenyl)piperidine (Preparation 45, 2.0 g, 8.10 mmol) in toluene (20 ml) at 85°

C. was added phenyl chloroformate (1.0 ml, 9.70 mmol) and the mixture was heated at reflux for 4 h. The solution was cooled to 45° C. and aqueous sodium hydroxide solution (1 ml of 50% aqueous sodium hydroxide solution in 8 ml of water) was added. The reaction mixture was cooled to room temperature and the organic layer was separated and washed with methanol: 1N aqueous hydrochloric acid (1:1, 2×20 ml), methanol: 1N aqueous sodium hydroxide solution (1:1, 25 ml) and water (20 ml). The organic extract was dried ($MgSO_4$), filtered and concentrated in vacuo to give the crude product. This was purified by silica column chromatography eluting with ethyl acetate:hexane (1:5) to give the title compound as an oil (1.7 g, 62%).

NMR ($CDCl_3$, selected data): 1.3 (d, 6H), 1.65–2.0 (m, 4H), 2.65–3.2 (m, 3H), 4.5 (m, 3H), 6.75–7.45 (m, 9H).

Preparation 47

3-(4-Piperidinyl)phenol 4-(3-(1-Methylethoxy)phenyl)-1-piperidine-carboxylic acid phenyl ester (Preparation 46, 1.7 g, 5.01 mmol) was heated under reflux in 47% aqueous hydrobromic acid:glacial acetic acid (1:1, 20 ml) for 16 h. The solution was allowed to cool to room temperature and water (10 ml) was added. The solution was extracted with methyl tert-butyl ether (3×10 ml) to remove phenol as a by-product. The pH was adjusted to 10.3–10.5 with 15% w:v aqueous sodium hydroxide solution and the reaction mixture was left at room temperature for 2 h to precipitate the product. After cooling to 0° C. the precipitate was filtered and washed with cold water (5 ml) to give the title compound as a solid (380 mg, 43%).

Preparation 48

N-Hexyl-4-(3-hydroxyphenyl)piperidine

To a stirred solution of 3-(4-piperidinyl)phenol (Preparation 47, 376 mg, 2.12 mmol) in N,N-dimethylformamide (5 ml) was added sodium hydrogen carbonate (267 mg, 3.18 mmol) and 1-bromohexane (0.36 ml, 2.55 mmol). The reaction mixture was heated at 100° C. for 4 h. The reaction mixture was then diluted with water (20 ml) and extracted with diethyl ether (3×10 ml). The combined organic extracts were dried ($MgSO_4$), filtered and concentrated in vacuo to give the title compound as an oil which was not purified further (500 mg, 89%).

NMR ($CDCl_3$, selected data for the free base): 0.9 (m, 3H), 1.25 (m, 6H), 2.0 (m, 2H), 2.35 (m, 3H), 3.1 (m, 2H), 6.6–7.1 (m, 4H).

Preparation 49

4-(3-(1-Carbamoyl-1-methylethoxy)phenyl)-N-hexylpiperidine

To a solution of N-hexyl-4-(3-hydroxyphenyl)piperidine (Preparation 48, 490 mg, 1.90 mmol) in 1,4-dioxan (12 ml) under an atmosphere of nitrogen was added caesium carbonate (1.24 g, 3.81 mmol) carefully followed by sodium hydride (60% dispersion in mineral oil, 152 mg, 3.81 mmol) in four portions over 10 min. The resultant mixture was stirred for 30 min then 2-bromo-2-methyl-propionamide (I. G. C. Coutts and M. R. Southcott, J. Chem. Soc., Perkin I, 1990, 767–771), (1.63 g, 3.81 mmol) was added and the mixture was heated under reflux for 16 h. The reaction mixture was cooled, filtered and concentrated in vacuo to give the crude product which was purified by silica column chromatography, eluting with a gradient of ethyl acetate-:hexane:0.880 ammonia (90:9:1 to 99:0:1) to give recovered starting phenol (100 mg, 21%) followed by the title compound as a clear oil (390 mg, 60%).

NMR ($CDCl_3$, selected data for the free base): 0.9 (m, 3H), 1.3 (m, 6H), 2.0 (m, 2H), 3.05 (m, 2H), 5.4 (br.s, 1H), 6.6 (br.s, 1H), 6.7–7.2 (m, 4H).

Preparation 50

4-(3-Aminophenyl)-N-hexylpiperidine

A solution of N-hexyl-4-(3-(2-hydroxy-2-methylpropanoylamino)phenyl)piperidine (Example 158) in 1,4-dioxan:5N aqueous hydrochloric acid solution (1:1, 10 ml) was heated under reflux overnight. The reaction mixture was cooled, diluted with water (10 ml) and extracted with diethyl ether (3×10 ml). The pH of the aqueous layer was adjusted to 8–9 using 5N aqueous sodium hydroxide, and extracted with dichloromethane (5×10 ml). The combined extracts were washed with brine (10 ml), dried ($Na_2SO_4$) and concentrated in vacuo to give the title compound as an oil which was not purified further (178 mg, 61% over two steps).

NMR ($CDCl_3$, selected data for the free base): 0.85 (m, 3H), 1.3 (m, 6H), 3.05 (m, 2H), 3.6 (m, 2H), 6.5–7.1 (m, 4H).

Preparation 51

N-Ethyl-4-methyl-4-(3-(1-methylethoxy)phenyl) piperidine (i) To N-ethyl-1, 2, 3, 6-tetrahydro-4-(3-(1-methylethoxy) phenyl)pyridine (Preparation 44, 4.2 g, 15.97 mmol) in tetrahydrofuran (30 ml) at −10° C. was added n-butyllithium (1.6M in hexane, 15.0 ml, 24.0 mmol) over 20 min via a syringe at which point a deep red color persisted. After 15 min the reaction mixture was cooled to −50° C. and dimethyl sulfate (1.59 ml, 16.8 mmol) was added dropwise over 20 min. The resultant pale yellow/brown solution was stirred for another 20 min at −50° C., then it was poured onto an ice cold aqueous ammonia solution (60 ml) with rapid stirring. This mixture was extracted with ethyl acetate (3×30 ml) and the combined organic extracts were dried ($Na_2SO_4$) and concentrated in vacuo to give an orange oil which was used without further purification.

(ii) The crude orange oil was dissolved in MeOH (20 ml) and the solution was cooled to −5° C. Solid sodium borohydride (724 mg, 19.2 mmol) was added portionwise over 20 min and the mixture was then allowed to stir at room temperature for 3 h. To this was added 1:1 acetone:saturated aqueous sodium hydrogen carbonate (10 ml), and after 5 min the mixture was concentrated in vacuo. Water (10 ml) was added and the aqueous layer was extracted with ethyl acetate (3×10 ml). The combined extracts were dried ($MgSO_4$), filtered and concentrated in vacuo to give the title compound as a crude oil (3.96 g) which was used without further purification.

NMR ($CDCl_3$, selected data for the free base): 1.1 (t, 3H), 1.2 (s, 3H), 1.35 (d, 6H), 2.35–2.6 (m, 6H), 4.6 (m, 1H), 6.7–7.2 (m, 4H).

Preparation 52

4-Methyl-4-(3-(1-methylethoxy)phenyl)-1-piperidinecarboxylic acid phenyl ester To N-ethyl-4-methyl-4-(3-(1-methylethoxy)phenyl) piperidine (Preparation 51, 3.98 g, 15.23 mmol) in toluene (30 ml) at 85° C. was slowly added phenyl chloroformate (2.1 ml, 16.75 mmol) and the mixture was then heated under reflux for 16 h. The solution was cooled to 45° C. and 50% w:v aqueous sodium hydroxide solution (2 ml) was added. Once the solution had cooled to room temperature the organic layer was separated and washed with methanol:1N aqueous hydrochloric acid (1:1, 3×10 ml), methanol:1N aqueous sodium hydroxide solution (1:1, 12 ml) and water (20 ml). The organic layer was dried ($MgSO_4$), filtered and concentrated in vacuo to give the crude product. This was purified by silica column chromatography using ethyl acetate:hexane (20:80) to give the title compound as an oil (2.5 g, 45% over three steps).

NMR ($CDCl_3$, selected data) 1.3 (s, 3H), 1.4 (d, 6H), 1.75 (m, 2H), 2.15 (m, 2H), 3.4–3.8 (m, 4H), 4.6 (m, 1H), 6.7–7.2 (m, 9H).

Preparation 53

N-Hexyl-4-(3-hydroxyphenyl)-4-methylpiperidine (i) A solution of 4-methyl-4-(3-(1-methylethoxy)phenyl)-1-piperidinecarboxylic acid phenyl ester (Preparation 52, 2.4 g, 6.80 mmol) in 1:1 47% aqueous hydrobromic acid:g-lacial acetic acid (8 ml) was heated under reflux for 16 h. The solution was allowed to cool to room temperature and water (5 ml) was added. The aqueous layer was extracted with methyl tert-butyl ether (3×10 ml) to remove phenol as by-product. The pH was adjusted to 10.3–10.5 with 15% w:v aqueous sodium hydroxide solution and the mixture was left at room temperature for 2 h to allow the product to precipitate. After cooling to 0° C. the precipitate was filtered and washed with cold water (5 ml) to give 4-(3-hydroxyphenyl)-4-methylpiperidine as a solid (776 mg, 60%).

(ii) To 4-(3-hydroxyphenyl)-4-methylpiperidine (776 mg, 4.06 mmol) in N,N-dimethylformamide (5 ml) was added sodium hydrogen carbonate (341 mg, 4.06 mmol) and 1-bromohexane (0.57 ml, 4.06 mmol). The reaction mixture was heated at 100° C. for 4 h and then allowed to cool to room temperature. The solution was poured onto water (20 ml) and extracted with diethyl ether (3×10 ml). The combined extracts were washed with water (20 ml), dried ($MgSO_4$) and concentrated in vacuo to give the title compound as a clear oil (1.0 g, 90%).

NMR ($CDCl_3$, selected data for the free base): 0.9 (t, 3H), 1.2 (s, 3H), 1.25 (m, 6H), 6.4 (br.s, 1H), 6.6–7.15 (m, 4H).

MS (thermospray): M/Z [$MH^+$] 276.3; $C_{18}H_{29}NO+H$ requires 276.2.

Preparation 54

N-Hexyl-4-methyl-4-(3-trifluoromethanesulfonyloxyphenyl)piperidine

To N-hexyl-4-(3-hydroxyphenyl)-4-methylpiperidine (Preparation 53, 252 mg, 0.87 mmol) in dichloromethane (5 ml) at room temperature was added triethylamine (0.25 ml, 1.83 mmol) and then N-phenylbis(trifluoromethanesulfonimide) (491 mg, 1.37 mmol). The mixture was stirred for 16 h at room temperature and then saturated aqueous sodium hydrogen carbonate solution (5 ml) was added. The two layers were separated and the aqueous layer was extracted with dichloromethane (2×10 ml). The combined organic extracts were dried ($MgSO_4$), filtered and concentrated in vacuo to give the crude product. This was purified by silica column chromatography eluting with a gradient of ethyl acetate:hexane:0.88 ammonia (50:50:1 to 100:0:1) to give the title compound as a colourless oil (167 mg, 45%).

MS (APCI): M/Z [$MH^+$] 407.9; $C_{19}H_{28}F_3NO_3S+H$ requires 408.2.

Preparation 55

N-Hexyl-4-methyl-4-(3-N-diphenylmethylideneaminophenyl)piperidine

To a solution of N-hexyl-4-methyl-4-(3-trifluoromethanesulfonyloxyphenyl)piperidine (Preparation 54, 133 mg, 0.33 mmol) in deoxygenated tetrahydrofuran (5 ml) at room temperature was added caesium carbonate (149 mg, 0.46 mmol), 3 mol % palladium acetate (2.2 mg, 9.8 mmol), 4.5 mol % 2,2'-bis(diphenylphosphino)-1-,1'-binaphthyl (9.2 mg, 14.7 mmol) and benzophenone imine (71 mg, 0.39 mmol). The mixture was heated under reflux for 20 h, cooled and the solid was removed by filtration washing with diethyl ether. The filtrate was concentrated in vacuo to give the crude product. This was purified by silica column chromatography eluting with a gradient of ethyl acetate:hexane:0.880 ammonia (50:50:1 to 98:2:1) to give the title compound as a yellow oil (112 mg, 78%).

NMR ($CDCl_3$, selected data for the free base): 0.9 (t, 3H), 1.0 (s, 3H), 6.6–7.8 (m, 14H).

Preparation 56

4-(3-Aminophenyl)-N-hexyl-4-methylpiperidine

To a solution of N-hexyl-4-methyl-4-(3-diphenylmethylideneaminophenyl)piperidine (Preparation 55, 112 mg, 0.26 mmol) in tetrahydrofuran (4 ml) was added 2N aqueous hydrochloric acid (1 ml) and the mixture was stirred at room temperature for 30 min. The mixture was concentrated in vacuo, 2N aqueous hydrochloric acid (3 ml) was added and the aqueous phase was extracted with hexane:ethyl acetate (2:1, 5 ml). The aqueous layer was then basified with 2N aqueous sodium hydroxide solution and extracted with dichloromethane (3×10 ml). The combined extracts of the basic aqueous layer were dried ($MgSO_4$), filtered and concentrated in vacuo to give the title compound which was used without further purification (70 mg, 99% crude yield).

NMR ($CDCl_3$, selected data for the free base) 0.9 (t, 3H), 1.2 (s, 3H), 1.3 (m, 6H), 1.9 (m, 2H), 2.15 (m, 2H), 3.6 (br.s, 2H), 6.5–7.1 (m, 4H).

Preparation 57

Ethyl 3-(3-nitrophenyl)-2-pentenoate

To a solution of sodium hydride (60% dispersion in oil, 40 g, 1.0 mol) in tetrahydrofuran (2 l) stirred at −10° C. under nitrogen was added triethylphosphonoacetate (224 g, 1.0 mol) dropwise over 30 min. To the mixture was added 3-nitropropiophenone (180 g, 1 mol) at such a rate that the temperature was maintained below 10° C. The mixture was allowed to warm to room temperature and was stirred for 18 h. Water (1.5 l) was added, and the mixture was extracted with diethyl ether (2×1 l). The combined extracts were washed with water (1 l), dried ($MgSO_4$), filtered and concentrated in vacuo and the residue was purified by silica column (4×2 kg) chromatography eluting with hexane:diethyl ether (12:1). Appropriate fractions were combined and concentrated in vacuo to give the title compound as a very pale yellow oil (105 g, 42%).

NMR ($CDCl_3$): 1.1 (t, 3H), 1.35 (t, 3H), 3.15 (q, 2H), 4.2 (q, 2H), 6.05 (s, 1H), 7.55 (t, 1H), 7.75 (d, 1H), 8.2 (d, 1H), 8.3 (s, 1H).

MS (thermospray): M/Z [MH$^+$] 250.0; $C_{13}H_{15}NO_4$+H requires 250.1.

Preparation 58

(E/Z)-3-(3-Nitrophenyl)-2-penten-1-ol

To a solution of ethyl 3-(3-nitrophenyl)-2-pentenoate (Preparation 57, 2 g, 8.03 mmol) in anhydrous toluene (144 ml) at −10° C. was added diisobutyl aluminium hydride (1.0 M solution in toluene, 18 ml, 18 mmol) dropwise at such a rate that the temperature did not rise above 0° C. The reaction mixture was stirred at 0° C. for 5 h and then it was allowed to warm to room temperature. The reaction mixture was again cooled to −10° C. and water (2 ml) was added cautiously, followed by ethyl acetate (40 ml) and then it was allowed to warm to room temperature. Solid sodium bicarbonate was added until the aluminium residues became a fine precipitate and the mixture was stirred at room temperature overnight. The reaction mixture was filtered and concentrated in vacuo, and the residue was partitioned between dichloromethane (75 ml) and water (75 ml). The phases were separated and the extract was dried (MgSO$_4$), filtered and concentrated in vacuo to give a 2:1 ratio of geometric isomers of the title compound as an oil which was used without further purification (1.5 g, 90%).

NMR (CDCl$_3$, selected data for the major isomer) 1.0 (t, 3H), 2.40 (dd, 2H), 4.0 (t, 2H), 5.80 (t, 1H), 7.2–8.3 (m, 4H). NMR (CDCl$_3$, selected data for the minor isomer): 2.60 (dd, 2H), 4.40 (t, 2H), 5.90 (t, 1H).

MS (thermospray): M/Z [MNa$^+$] 230.2; $C_{11}H_{13}NO_3$+Na requires 230.1.

Preparation 59

Methyl 3-ethyl-3-(3-nitrophenyl)-4-pentenoate

A solution of (E/Z)-3-(3-nitrophenyl)-2-penten-1-ol (Preparation 58, 1.5 g, 7.25 mmol) in trimethyl orthoacetate (10 ml) was heated under reflux for 5 h and then the reaction mixture was concentrated in vacuo. The residue was dissolved in petroleum spirit 140–160° C. (20 ml) and was heated under reflux under nitrogen employing a Dean-Stark apparatus for 24 h. The reaction mixture was concentrated in vacuo to give the title compound as an oil which was used without further purification.

MS (thermospray): M/Z [MNH$_4^+$] 281.2; $C_{14}H_{17}NO_4$+NH$_4$ requires 281.2.

Preparation 60

3-Ethyl-3-(3-nitrophenyl)-4-pentenoic acid

A solution of methyl 3-ethyl-3-(3-nitrophenyl)-4-pentenoate (Preparation 59, assume 7.25 mmol) in isopropyl alcohol (9 ml) and 2M aqueous sodium hydroxide solution (4.4 ml, 8.75 mmol) was heated under reflux for 11 h, then the reaction mixture was concentrated in vacuo. The residue was partitioned between ethyl acetate and water. The phases were separated and the organic extract was dried (MgSO$_4$), filtered and concentrated in vacuo to give the title compound as an oil which was used without further purification.

NMR (CDCl$_3$, selected data): 0.80 (t, 3H), 2.80 (dd, 2H), 3.50 (s, 2H), 5.10 (d, 1H), 5.30 (d, 1H), 6.0 (dd, 1H), 7.4–7.7 (m, 2H), 8.0–8.2 (m, 2H).

MS (thermospray): M/Z [MNH$_4^+$] 267.0; $C_{13}H_{15}NO_4$+NH$_4$ requires 267.3.

Preparation 61

3-Ethyl-3-(3-nitrophenyl)-1,5-pentanediol

To a solution of 3-ethyl-3-(3-nitrophenyl)-4-pentenoic acid (Preparation 60, assume 7.25 mmol) in tetrahydropyran (43 ml) at 0° C. was added sodium borohydride (0.55 g, 14.5 mmol) and the reaction mixture was stirred at 0° C. for 10 min. To the reaction mixture was added borontrifluoride tetrahydrofuran complex (2.72 g, 19.4 mmol) over 5 min. The reaction mixture was stirred under nitrogen at 0° C. for 30 min then it was allowed to warm to room temperature overnight. Ethanol (10 ml) was added cautiously, followed sequentially by water (10 ml), 2M aqueous sodium hydroxide solution (1.8 ml), water (10 ml) and finally 2M aqueous sodium hydroxide solution (1.8 ml). Solid sodium carbonate (1.8 g) was added followed by 30% w:w aqueous hydrogen peroxide solution (60 ml) and the reaction mixture was stirred at room temperature for 30 minutes. The mixture was filtered and the filtrate was partitioned between brine (100 ml) and ethyl acetate (100 ml). The phases were separated and the organic extract was dried (MgSO$_4$), filtered and concentrated in vacuo to give the crude product. This was purified by silica (150 g) column chromatography eluting with a gradient of ethyl acetate:toluene: 0.880 ammonia (49:50:1 to 66:33:1) to give the title compound as a yellow oil (661 mg, 34% over 3 steps).

NMR (CDCl$_3$, selected data): 0.7 (t, 3H), 3.5–3.7 (m, 4H), 7.1 (d, 2H), 7.2 (d, 2H), 7.4–7.8 (m, 2H), 8.0–8.3 (m, 2H).

MS (thermospray): M/Z [MNH$_4^+$] 271.2; $C_{13}H_{19}NO_4$+NH$_4$ requires 271.2.

Preparation 62

3-Ethyl-5-((methylsulfonyl)oxy)-3-(3-nitrophenyl) pentyl methanesulfonate

To a solution of 3-ethyl-3-(3-nitrophenyl)-1,5-pentanediol (Preparation 61, 661 mg, 2.27 mmol) in toluene (24 ml) was added triethylamine (0.76 ml, 5.43 mmol) followed by methanesulfonyl chloride (0.42 ml, 5.4 mmol). The reaction mixture was stirred at room temperature under nitrogen for 18 h. The reaction mixture was poured onto water (10 ml), the phases were separated and the aqueous layer was extracted with dichloromethane (10 ml). The combined extracts were dried (MgSO$_4$), filtered and concentrated in vacuo to give the title compound as an oil which was used without further purification (850 mg, 81% crude yield).

MS (thermospray): M/Z [MNH$_4^+$] 427.2; $C_{15}H_{23}NO_8S_2$+NH$_4$ requires 427.1.

Preparation 63

4-Ethyl-N-hexyl-4-(3-nitrophenyl)piperidine

To a solution of 3-ethyl-5-((methylsulfonyl)oxy)-3-(3-nitrophenyl)pentyl methanesulfonate (Preparation 62, 850 mg, 2.1 mmol) in toluene (6 ml) under an atmosphere of nitrogen was added hexylamine (1.66 ml, 12.6 mmol). The reaction mixture was heated under reflux for 16 h, then it was concentrated in vacuo to give the crude product. This was purified by silica (25 g) column chromatography eluting with ethyl acetate:hexane:0.880 ammonia (49:50:1) to give the title compound as a clear oil (335 mg, 50%).

NMR (CDCl$_3$, selected data for the free base) 0.5 (t, 3H), 1.4–2.3 (m, 14H), 3.1–3.6 (m, 7H), 7.3–8.2 (m, 4H).

MS (thermospray): M/Z [MH$^+$] 319.2; $C_{19}H_{30}N_2O_2$+H requires 319.2.

Preparation 64

4-(3-Aminophenyl)-4-ethyl-N-hexylpiperidine

To a solution of 4-ethyl-N-hexyl-4-(3-nitrophenyl) piperidine (Preparation 63, 335 mg, 1.05 mmol) in 9:1 ethanol:water (41 ml) was added iron powder (530 mg, 9.45 mmol) followed by calcium chloride (58 mg, 0.53 mmol). The reaction mixture was heated under reflux for 2 h, then the mixture was allowed to cool. The mixture was filtered and the filtrate was concentrated in vacuo. The residue was partitioned between dichloromethane (20 ml) and water (20 ml). The phases were separated and the organic extract was dried (MgSO$_4$), filtered and concentrated in vacuo to give the crude product. This was purified by silica (10 g) column chromatography eluting with methanol:dichloromethane:0.880 ammonia (10:89:1) to give the title compound as a brown oil (103 mg, 34%).

NMR (CDCl$_3$, selected data for the free base): 0.5 (t, 3H), 0.90 (m, 3H), 1.20–2.40 (m, 12H), 2.60 (m, 1H), 3.30 (m, 1H), 6.50 (d, 1H), 6.60 (s, 1H), 6.70 (d, 1(d, 1H), 7.10 (t, 1H).

MS (thermospray): M/Z [MH$^+$] 289.2; C$_{19}$H$_{32}$N$_2$+H requires 289.3.

Preparation 65

N-Ethyl-4-(3-(1-methylethoxy)phenyl)-4-n-propylpiperidine (i) To N-ethyl-1,2,3,6-tetrahydro-4-(3-(1-methylethoxy)phenyl)pyridine (Preparation 44, 10 g, 40.8 mmol) in tetrahydrofuran (75 ml) at –10° C. was added n-butyllithium (2.5M in hexanes, 22.9 ml, 57.25 mmol) over 20 min via a syringe at which point a deep red color persisted. After 30 min the reaction mixture was cooled to –20° C. and n-propyl bromide (3.89 ml, 42.9 mmol) was added dropwise over 20 min. The resultant pale yellow/brown solution was stirred for another 50 min at –20 ° C., then saturated aqueous sodium hydrogen carbonate (50 ml) was added and reaction mixture was allowed to warm to room temperature. The mixture was diluted with water (100 ml) and extracted with hexane (3×100 ml), and the combined extracts were washed with water (50 ml), dried (Na$_2$SO$_4$) and concentrated in vacuo to give a dark orange oil (10.8 g) which was used without further purification.

(ii) The crude orange oil (10.8 g) was dissolved in MeOH (50 ml) and the solution was cooled to 0° C. Solid sodium borohydride (1.86 g, 49.0 mmol) was added portionwise over 20 min and the mixture was then allowed to stir at room temperature for 3 d. To this was added 1:1 acetone:saturated aqueous sodium hydrogen carbonate (10 ml), and after 10 min the mixture was concentrated in vacuo. Water (50 ml) was added and the aqueous mixture was extracted with diethyl ether (100, 2×50 ml). The combined extracts were washed with water and brine (25 ml each), dried (Na$_2$SO$_4$), filtered and concentrated in vacuo to give the title compound as a crude brown oil (11.1 g) which was used without further purification.

NMR (CDCl$_3$, selected data for the free base): 0.75 (m, 3H), 1.05 (m, 3H), 1.8 (m, 2H), 2.2 (m, 2H), 2.35 2.6 (m, 2H), 4.55 (m, 1H), 6.65–6.85 (m, 3H), 7.2 (m, 1H).

MS (thermospray): M/Z [MH$^+$] 290.3; C$_{19}$H$_{31}$NO+H requires 290.2.

Preparation 66

4-(3-(1-Methylethoxy)phenyl)-4-n-propyl-1-piperidinecarboxylic acid phenyl ester To N-ethyl-4-(3-(1-methylethoxy)phenyl)-4-n-propylpiperidine (Preparation 65, 10.9 g) in toluene (80 ml) under nitrogen at 85° C. was slowly added phenyl chloroformate (5.63 ml, 44.88 mmol) over 20 min. The mixture was then heated under reflux for 4 h. The solution was cooled to 50° C. and 5M aqueous sodium hydroxide (10 ml) was added. Once the solution had cooled to room temperature the layers were separated and the organic extract was washed with methanol:1N aqueous hydrochloric acid (1:1, 2×10 ml), methanol 1N aqueous sodium hydroxide solution (1:1, 20 ml) and water (20 ml). The organic layer was dried (Na$_2$SO$_4$), filtered and concentrated in vacuo to give the crude product. This was purified by silica column chromatography using ethyl acetate:hexane:0.880 ammonia (15:85:1) to give the title compound as a pale yellow oil (6.9 g, 42% over three steps).

NMR (CDCl$_3$, selected data for the free base): 0.8 (m, 3H), 1.0 (m, 2H), 1.8 (m, 2H), 2.25 (m, 2H), 3.3 (m, 2H), 3.85 (m, 2H), 4.55 (m, 1H), 6.7–6.9 (m, 3H), 7.05–7.4 (m, 6H).

MS (thermospray): M/Z [MH$^+$] 399.5; C$_{24}$H$_{31}$NO$_3$+H requires 399.2.

Preparation 67

4-(3-Hydroxyphenyl)-4-n-propylpiperidine

A solution of 4-(3-(1-methylethoxy)phenyl)-4-n-propyl-1-piperidinecarboxylic acid phenyl ester (Preparation 66, 6.7 g, 17.6 mmol) in 1:1 47% aqueous hydrobromic acid:glacial acetic acid (20 ml) was heated under reflux overnight. The solution was allowed to cool to room temperature and water (10 ml) was added. The aqueous layer was extracted with methyl tert-butyl ether (3×20 ml) to remove phenol as by-product. The aqueous layer was basified with 10M aqueous sodium hydroxide solution. At approximately pH 4, a biphasic solution developed as more methyl tert-butyl ether came out of solution. The layers were separated, and the aqueous layer was further diluted with water (10 ml) to solubilise a red oily deposit. The pH was adjusted to 10.3–10.5 with 10M aqueous sodium hydroxide and the precipitate was filtered and dried in vacuo at 50° C. to give the title compound as a pale brown solid (1.87 g, 48%).

NMR (CD$_3$OD, selected data for the free base): 0.85 (m, 3H), 1.0 (m, 2H), 1.5 (m, 2H), 1.7 (m, 2H), 2.2 (m, 2H), 2.7 (m, 2H), 2.85 (m, 2H), 6.6–6.8 (m, 3H), 7.15 (m, 1H).

MS (thermospray): M/Z [MH$^+$] 220.3; C$_{14}$H$_2$,NO+H requires 220.2.

Preparation 68

N-Hexyl-4-(3-hydroxyphenyl)-4-n-propylpiperidine

To 4-(3-hydroxyphenyl)-4-n-propylpiperidine (Preparation 67, 1.10 g, 5.0 mmol) in N,N-dimethylformamide (25 ml) was added sodium hydrogen carbonate (462 mg, 5.5 mmol) and 1-bromohexane (0.77 ml, 5.5 mmol). The reaction mixture was heated at 100° C. for 3 h 30 min and then allowed to cool to room temperature. The mixture was diluted with water (25 ml) and extracted with dichloromethane (3×25 ml). The combined extracts were washed with water (20 ml), dried (MgSO$_4$) and concentrated in vacuo. The residue was purified by (50 g) silica column chromatography eluting with ethyl acetate:hexane:0.880 ammonia (40:60:1) to give the title compound as a pale yellow oil (1.17 g, 77%).

NMR (CDCl$_3$, selected data for the free base): 0.9 (t, 3H), 1.25 (m, 6H), 1.8 (m, 2H), 2.6 (m, 2H), 6.4–6.65 (m, 3H), 7.15 (m, 1H).

MS (thermospray): M/Z [MH$^+$] 304.4; C$_{20}$H$_{33}$NO+H requires 304.3.

Preparation 69

N-Hexyl-4-n-propyl-4-(3-trifluoromethanesulfonyloxyphenyl)piperidine

To N-hexyl-4-(3-hydroxyphenyl)-4-n-propylpiperidine (Preparation 68, 1.0 g, 3.3 mmol) in dichloromethane (20 ml) under nitrogen at room temperature was added triethylamine (5 ml) and then N-phenylbis(trifluoromethanesulfonimide) (1.53 g, 4.29 mmol). The mixture was stirred for 16 h at room temperature and then 1N aqueous sodium hydroxide solution (5 ml) was added. After 1 h, water (5 ml) was added, the two layers were separated and the aqueous layer was extracted with dichloromethane (2×10 ml). The combined extracts were washed with water (10 ml), dried ($Na_2SO_4$), filtered and concentrated in vacuo to give the title compound as a yellow oil which was used without further purification (1.34 g, 94% crude yield).

NMR ($CDCl_3$, selected data for the free base): 0.75 (m, 3H), 1.25 (m, 6H), 1.9 (m, 2H), 2.6 (m, 2H), 7.05–7.45 (m, 4H).

MS (thermospray): M/Z [$MH^+$] 436.4; $C_{21}H_{33}F_3NO_3S$+H requires 436.2.

Preparation 70

4-(3-Aminophenyl)-N-hexyl-4-n-propylpiperidine (i) To a solution of N-hexyl-4-n-propyl-4-(3-trifluoromethanesulfonyloxyphenyl)piperidine (Preparation 69, 1.33 g, 3.05 mmol) in deoxygenated tetrahydrofuran (50 ml) at room temperature was added caesium carbonate (1.43 g, 4.41 mmol), 3 mol % palladium acetate (21 mg, 0.1 mmol), 4.5 mol % 2,2'-bis(diphenylphosphino)-1-1'-binaphthyl (89 mg, 1.5 mmol) and benzophenone imine (0.69 g, 0.64 ml, XX mmol). The mixture was heated under reflux for 2 d, when NMR of an aliquot that was removed and subjected to standard work-up indicated approximately 75% conversion. The reaction mixture was allowed to cool and the solid was removed by filtration washing with diethyl ether. The filtrate was concentrated in vacuo to give a residue that was partitioned between water (25 ml) and dichloromethane (50 ml). The layers were separated and the aqueous layer was extracted with dichloromethane (40 ml). The combined extracts were washed with water (40 ml), dried ($Na_2SO_4$), filtered and concentrated in vacuo. The residue was purified by silica column chromatography eluting with a gradient of ethyl acetate:hexane:0.880 ammonia (50:50:1 to 98:2:1) to give 4-methyl-4-(3-diphenylmethylideneaminophenyl)-4-n-propylpiperidine which was used without further purification.

(ii) To a solution of 4-methyl-4-(3-diphenylmethylideneaminophenyl)-4-n-propylpiperidine (1.42 g, 3.05 mmol) in tetrahydrofuran (20 ml) was added 2N aqueous hydrochloric acid (10 ml) and the mixture was stirred at room temperature for 1 h. Ethyl acetate:hexane (1:1, 20 ml) was added and the biphasic mixture was stirred for 30 min. The layers were separated and the organic layer was extracted with 2N aqueous hydrochloric acid (10 ml). The pH of the combined aqueous extracts was adjusted to 8 using 10N aqueous sodium hydroxide solution, and this was extracted with ethyl acetate (50, 25 ml). The combined extracts of the basic aqueous layer were washed with water (20 ml), dried ($MgSO_4$), filtered and concentrated in vacuo. The residue was purified by silica (50 g) column chromatography eluting with ethyl acetate:hexane:0.880 ammonia (33:66:1 to 50:50:1) to give the title compound as a pale yellow oil (500 mg, 54% over two steps).

NMR ($CDCl_3$, selected data for the free base): 0.75 (m, 3H), 1.25 (m, 6H), 1.8 (m, 2H), 2.6 (m, 2H), 3.6 (br.s, 2H), 6.5–6.7 (m, 3H), 7.1 (m, 1H).

MS (thermospray): M/Z [$M^+$] 303.6; $C_{22}H_{34}N_2$+H requires 303.3.

Preparation 71

(±)-4-(3-N,N-Diethylaminocarbonyloxyphenyl)-N-hexyl-trans-3,4-dimethylpiperidine To a solution of (±)-N-hexyl-4-(3-hydroxyphenyl)-trans-3,4-dimethylpiperidine (Preparation 1, 2.0 g, 6.92 mmol) in acetone (15 ml) was added potassium carbonate (2.72 g, 25.7 mmol) and N,N-diethylcarbamoyl chloride (3.26 ml, 25.7 mmol), and the mixture was heated under reflux for 6 h and then cooled to room temperature. The mixture was filtered and the filtrate was concentrated in vacuo to give the crude product. This was purified by silica column chromatography eluting with a gradient of hexane:ethyl acetate (5:1 to 2:1) to afford the title compound as a colourless oil (1.76 g, 66%).

NMR ($CDCl_3$, selected data for the free base): 0.8 (d, 3H), 0.9 (m, 3H), 1.2–1.4 (m, 15H), 1.4–1.55 (m, 2H), 1.6 (m, 1H), 2.0 (m, 1H), 2.2–2.6 (m, 6H), 2.8 (m, 1H), 3.3–3.5 (m, 4H), 6.95 (d, 1H), 7.05 (s, 1H), 7.15 (d, 1H), 7.25 (m, 1H).

MS (APCI): M/Z [$MH^+$] 389.0; $C_{24}H_{40}N_2O_2$+H requires 389.3.

Preparation 72

(±)-4-((3-N,N-Diethylaminocarbonyloxy)-4-methylphenyl)-N-hexyl-trans-3,4-dimethylpiperidine To a solution of (±)-4-(3-N,N-diethylaminocarbonyloxyphenyl)-N-hexyl-trans-3,4-dimethylpiperidine (Preparation 71, 0.38 g, 0.98 mmol) in tetrahydrofuran (2.5 ml) under nitrogen at −78° C., was added N,N,N',N'-tetramethylethylenediamine (0.29 ml, 1.95 mmol) and sec-butyllithium (1.3M solution in cyclohexane, 1.50 ml, 1.95 mmol). The solution was stirred for 45 min at −78° C., and then methyl iodide (0.28 g, 1.95 mmol) was added dropwise. The mixture was allowed to warm to −20° C. over 1 h, and saturated aqueous sodium hydrogen carbonate solution (5.0 ml) was added. The mixture was extracted with diethyl ether (3×5 ml) and the combined extracts were dried ($MgSO_4$), filtered and concentrated in vacuo to give the crude product. This was purified by silica column chromatography eluting with hexane:ethyl acetate (3:1) to give the title compound as a colourless oil (0.29 g, 74%).

NMR ($CDCl_3$, selected data for the free base): 0.8 (d, 3H), 0.9 (m, 3H), 1.18–1.38 (m, 15H), 1.40–1.53 (m, 2H), 1.60 (m, 1H), 1.95 (m, 1H), 2.18 (s, 3H), 2.20–2.60 (m, 6H), 2.80 (m, 1H), 3.32–3.58 (m, 4H), 6.99 (s, 1H), 7.02 (d, 1H), 7.12 (d, 1H).

MS (thermospray): M/Z [$MH^+$] 403.0; $C_{25}H_{42}N_2O_2$+H requires 403.3.

Preparation 73

(±)-N-Hexyl-4-(3-hydroxy-4-methylphenyl)-trans-3,4-dimethylpiperidine

To a solution of (±)-4-((3-N,N-diethylaminocarbonyloxy)-4-methylphenyl)-N-hexyl-trans-3,4-dimethylpiperidine (Preparation 72, 290 mg, 0.72 mmol) in tetrahydrofuran (5 ml) under nitrogen at 0° C., was added lithium aluminium hydride (1.0 M solution in diethyl ether, 1.44 ml, 1.44 mmol). The solution was stirred at room temperature for 3 h then water (1 ml) was added at 0° C. followed by 1N aqueous sodium hydroxide solution (2.0 ml) and finally water (5 ml). The mixture was filtered and the solid was washed with tetrahydrofuran (15 ml). The filtrate was concentrated in vacuo, taken up in dichloromethane (20 ml) and treated with 1N aqueous sodium hydroxide solution (15 ml). The two layers were separated and the aqueous layer was extracted with dichloromethane (3×10 ml). The combined extracts were dried ($MgSO_4$), filtered and concentrated in vacuo to give the crude product. This was purified by silica column chromatography eluting with hexane:ethyl acetate (1:1) to give the title compound as a colourless oil (170 mg, 77%).

NMR ($CDCl_3$, selected data for the free base): 0.79 (d, 3H), 0.90 (t, 3H), 1.22–1.38 (m, 9H), 1.40–1.53 (m, 2H), 1.60 (m, 1H), 1.95 (m, 1H), 2.20 (s, 3H), 2.22–2.61 (m, 6H), 2.80 (m, 1H), 6.70 (s, 1H), 6.79 (d, 1H), 7.02 (d, 1H).

Preparation 74

(±)-N-Hexyl-trans-3,4-dimethyl-4-(4-methyl-3-(trifluoromethanesulfonyloxyphenyl)phenyl)piperidine To a solution of (±)-N-hexyl-4-(3-hydroxy-4-methylphenyl)-trans-3,4-dimethylpiperidine (Preparation 73, 167 mg, 0.55 mmol) in dichloromethane (5 ml) at room temperature under nitrogen was added triethylamine (0.13 ml, 0.94 mmol) and N-phenylbis(trifluoromethanesulfonimide) (295 mg, 0.83 mmol). The reaction mixture was stirred at room temperature for 16 h and then concentrated in vacuo to give the crude product. This was purified by silica column chromatography eluting with hexane:ethyl acetate (3:1) to give the title compound as a colourless oil (0.17 g, 71%).

NMR ($CDCl_3$, selected data for the free base): 0.75 (d, 3H), 0.90 (m, 3H), 1.4–1.6 (m, 3H), 1.95 (m, 1H), 2.35 (s, 3H), 2.4–2.6 (m, 2H), 2.8 (m, 1H), 7.1–7.25 (m, 3H).

MS (thermospray): M/Z [$MH^+$] 436.3; $C_{21}H_{32}F_3NO_3S+H$ requires 436.2.

Preparation 75

(±)-4-(3-Amino-4-methylphenyl)-N-hexyl-trans-3,4-dimethylpiperidine (±) To a solution of (±)-N-Hexyl-trans-3,4-dimethyl-4-(4-methyl-3-(trifluoromethanesulfonyloxyphenyl)phenyl)piperidine (Preparation 74, 196 mg, 0.45 mmol) in deoxygenated tetrahydrofuran (4.5 ml) under nitrogen was added caesium carbonate (206 mg, 0.63 mmol), palladium acetate (3.0 mg, 0.01 mmol), 2,2'-bis(diphenylphosphino)-1,1'-binapthyl (12.6 mg, 0.02 mmol) and a solution of benzophenone imine (91 µl, 0.54 mmol) in tetrahydrofuran (0.5 ml). The reaction mixture was heated under reflux for 20 h and then cooled to room temperature. The mixture was filtered, the solid was washed with diethyl ether and the filtrate was concentrated in vacuo to give a crude residue. This was purified by silica column chromatography eluting with a gradient of hexane:ethyl acetate (5:1 to 3:1) to afford (±)-N-hexyl-trans-3,4-dimethyl-4-(4-methyl-3-(diphenylmethylideneamino)phenyl)piperidine as a colourless oil (86 mg).

(ii) A solution of (±)-N-hexyl-trans-3,4-dimethyl-4-(4-methyl-3-(diphenylmethylideneamino)phenyl)piperidine (86 mg, 0.19 mmol) in tetrahydrofuran:2N aqueous hydrochloric acid (4:1, 3.0 ml) was stirred at room temperature for 1 h. The solvent was concentrated in vacuo and 2N aqueous hydrochloric acid (2.0 ml) was added to the residue. The aqueous layer was first extracted with hexane:ethyl acetate (2:1, 3 ml) and then basified with 2N aqueous sodium hydroxide solution to pH 12. The basic aqueous layer was extracted with dichloromethane (3×5 ml) and the combined extracts were dried ($MgSO_4$), filtered and concentrated in vacuo to give the crude product as a colourless oil (30 mg, 22%) which was used without further purification.

NMR ($CDCl_3$, selected data for the free base): 0.8–0.9 (m, 6H), 2.05 (m, 1H), 2.15 (s, 3H), 2.85 (m, 1H), 3.60 (br s, 2H), 6.6–6.65 (m, 2H), 6.95 (d, 1H).

MS (thermospray): M/Z [$MH^+$] 303.6; $C_{20}H_{34}N_2+H$ requires 303.3.

Preparation 76

Ethyl 3-(3-bromophenyl)-2-methyl-2-butenoate

To a suspension of potassium tert-butoxide (183.1 g, 1.63 mol) in toluene (1400 ml) under an atmosphere of nitrogen was slowly added triethyl 2-phosponopropionate (361.1 g, 1.52 mol) with ice cooling at such a rate that the internal temperature was maintained at approximately 20° C. The resultant yellow solution was stirred at room temperature for 3 h after which time it was cooled in an ice bath. To this cooled solution was added a solution of 3-bromoacetophenone (274.2 g, 1.38 mol) in toluene (400 ml) at such a rate that the internal temperature did not rise above 20 ° C. The resultant red-brown solution was then stirred at room temperature for 18 h. After this time, more potassium tert-butoxide (38.7 g, 0.34 mol) was added, and the resultant mixture was stirred at room temperature for an additional 20 h. The reaction was quenched by the cautious addition of water (2000 ml), and the layers were separated. The organic layer was washed with water (4×2000 ml), and was then concentrated in vacuo to give the crude product as a brown oil (344 g) which was distilled under reduced pressure to give the impure title compound (2:3 mixture of geometric isomers) as a colourless liquid (212 g) which was contaminated with small amounts of triethyl 2-phosphonopropionate and 3-bromoacetophenone. In the present synthetic route the impure title compound was taken forward into the next step without any further purification. However, purification, for example using flash chromatography eluting with 5% ethyl acetate in hexane, affords the analytically pure title compound as a clear colourless oil.

NMR ($CDCl_3$): 0.9 (t, 1H, minor isomer), 1.35 (t, 2H, minor isomer), 1.75 (s, 2H, major isomer), 2.0 (s, 1H, minor isomer), 2.05 (s, 1H, minor isomer), 2.2 (s, 2H, major isomer), 3.9 (q, 0.67H, minor isomer), 4.25 (q, 1.33H, major isomer), 7.0–7.45 (m, 4H). b.p. 115–1190° C. @ 0.4 mmHg.

Preparation 77

3-(3-Bromophenyl)-2-methyl-2-butenol

To a solution of ethyl 2-methyl-3-(3-nitrophenyl)-2-butenoate (Preparation 76, 100 g, 353 mmol) in dry tetrahydrofuran (800 ml) at −12° C. (internal temperature) under an atmosphere of nitrogen was slowly added diisobutylaluminium hydride (1.0M solution in heptane, 800 ml, 0.8 mol) at such a rate that the internal temperature did not rise above 5° C. The resultant mixture was stirred with cooling for a further 1 h 30 min, and was then cannulated into a solution of citric acid (300 g) in water (1 l) at 0° C. at such a rate that the temperature did not rise above 20° C. The resultant mixture was stirred at room temperature for 1 h 30 min after which time the layers were separated and the aqueous phase was extracted with ethyl acetate (1×250 ml). The combined extracts were washed successively with water (1 l), saturated aqueous sodium bicarbonate solution (1 l) and saturated brine (1 l), dried (MgSO$_4$) and concentrated in vacuo to give the crude title compound (2:3 mixture of geometric isomers) as a clear oil (89.1 g) that contained approximately 5% by weight of ethyl acetate. In the present synthetic route the crude mixture was taken forward into the next step without any purification. However, purification, for example using distillation under reduced pressure affords the analytically pure title compound.

NMR (CDCl$_3$): 1.65 (s, 2H, major isomer), 1.9 (s, 1H, minor isomer), 2.0 (s, 1H, minor isomer), 2.05 (s, 2H, major isomer), 3.95 (s, 0.67H, minor isomer), 4.3 (s, 1.33H, major isomer), 7.0–7.4 (m, 4H). b.p. 123–128° C. @ 0.4 mmHg.

Preparation 78

(±)-Methyl 3-(3-bromophenyl)-3,4-dimethyl-4-pentenoate

A solution of crude 2-methyl-3-(3-nitrophenyl)-2-butenol (Preparation 77, 59.3 g, 246 mmol) in trimethylortho acetate (300 ml) was heated under reflux under a nitrogen atmosphere for 4 h, and was then allowed to stand at room temperature for 18 h. The resultant mixture was concentrated in vacuo to give an oil (83.3 g) which was dissolved in nonane (500 ml). The resultant solution was heated under reflux under an atmosphere of nitrogen with a Dean-Stark trap fitted for 24 h with periodic draining of the Dean-Stark trap. After this time, the reaction mixture was cooled and concentrated in vacuo to give the crude title compound as a slightly yellow mobile liquid (108 g) which still contained appreciable amounts of nonane. In the present synthetic route the crude mixture was taken forward into the next step without any purification. However, purification, for example using flash chromatography eluting with a gradient of ethyl acetate:hexane (5:95 to 20:80) affords the analytically pure title compound.

NMR (CDCl$_3$): 1.55 (s, 3H), 1.6 (s, 3H), 2.8 (d, 1H), 2.9 (s, 1H), 5.0 (br. s, 2H), 7.1–7.45 (m, 4H).

Preparation 79

(±)-3-(3-Bromophenyl)-3,4-dimethyl-4-pentenoic acid

To a solution of crude (±)-methyl 3-(3-bromophenyl)-3,4-dimethyl-4-pentenoate (Preparation 78, 108 g, assumed 0.25 mol) in isopropanol (350 ml) was added 2M aqueous sodium hydroxide solution (175 ml, 0.35 mol), and the resultant mixture was heated under reflux for 2 h. The mixture was cooled and then concentrated in vacuo to give a yellow oil which was crystallised by the addition of toluene (200 ml). The suspension was concentrated in vacuo, and the solid residue was suspended in toluene (250 ml). The solid was collected by filtration, washed with toluene (2×100 ml), and allowed to dry at room temperature to give a white solid (96 g). This material was added to water (500 ml), the pH was adjusted to 1 by the addition of concentrated hydrochloric acid and the resultant mixture was extracted with ethyl acetate (2×300 ml). The combined extracts were washed with saturated brine (200 ml), dried (MgSO$_4$), filtered and concentrated in vacuo to give a viscous oil that crystallised on standing to give the title compound as a white solid (52.2 g, 75%).

NMR (CDCl$_3$): 1.55 (s, 3H), 1.6 (s, 3H), 2.8 (d, 1H), 2.9 (s, 1H), 3.55 (s, 3H), 5.0 (brs, 2H), 7.1–7.45 (m, 4H).

Preparation 80

(±)-3-(3-Bromophenyl)-3,4-dimethyl-4-pentenoic acid

A solution of (±)-3-(3-bromophenyl)-3,4-dimethyl-4-pentenoic acid (Preparation 79, 634.3 g, 2.24 mol) in acetone (9.2 l) was heated to 52° C., and (S)-(+)-cyclohexylethylamine (285 g, 2.24 mol) was added dropwise over 15 minutes. The resultant clear solution was placed in an ice bath, and was allowed to cool to 42° C. at which point the crystallisation was seeded. The resultant suspension was then stirred at ambient temperature for 18 h. The solid was collected by filtration, washed with acetone (500 ml) and dried in vacuo to give a white solid (395.3 g, 43%). A suspension of this solid (395.3 g) in acetone (4 l) was heated under reflux until dissolution was almost complete, and the mixture was allowed to cool to ambient temperature. The resultant thick slurry was stirred at ambient temperature for 3 h, and was then cooled to 5° C. The solid was collected by filtration, washed with acetone (500 ml) and dried in vacuo to give a white solid (334 g). To a suspension of this solid (334 g) in dichloromethane (1 l) was added water (2 l) and the resultant biphasic mixture was cooled to 0° C. The pH was adjusted to 1 by the addition of concentrated hydrochloric acid, and the phases were separated. The aqueous phase was extracted with dichloromethane (2×500 ml), and the combined extracts were concentrated in vacuo to give a viscous oil. This material was re-dissolved in toluene (1 l) and then concentrated in vacuo to give a viscous oil that crystallised on standing to afford the title compound as a white solid (239.3 g, 37.5% overall, 75% of theory). HPLC analysis (Chiralpak AS column eluting with 99:1:0.1 hexane:ethanol:trifluoroacetic acid, flow rate 1 ml/min, detection at 220 nM) showed the product to be predominantly the (+)-enantiomer ((+): (−) 96:4).

NMR (CDCl$_3$): 1.55 (s, 3H), 1.6 (s, 3H), 2.8 (d, 1H), 2.9 (s, 1H), 5.0 (br s, 2H), 7.1–7.45 (m, 4H).

Preparation 81

(+)-3-(3-Bromophenyl)-trans-2,3-dimethyl-1,5-pentanediol

To a solution of (+)-3-(3-bromophenyl)-3,4-dimethyl-4-pentenoic acid (Preparation 80, 122.3 g, 0.432 mol) in dry tetrahydrofuran (2 l) under an atmosphere of nitrogen was added sodium borohydride (24.51 g, 0.648 mol) in portions over 10 min. The resultant mixture was then cooled to 0° C., and boron trifluoride-tetrahydrofuran complex (121 g, 0.864 mol) was cautiously added over 15 min. The resultant mixture was stirred at 0° C. for 1 h and then at room temperature for 18 h. The reaction mixture was cooled to 0° C., and ethanol (100 ml) was cautiously added. Water (1.8 l) was added followed by sodium percarbonate (203.4 g, 1.3 mol), and the resultant mixture was stirred at room temperature for 1 h 30 min. The mixture was filtered, and the filtrate was diluted with water (1 l). The diluted filtrate was extracted with ethyl acetate (3×1 l), and the combined extracts were washed with water (1 l) and brine (1 l). The organic phase was concentrated in vacuo to give a wet oil that was re-dissolved in toluene (1 l) and concentrated in vacuo to give a viscous oil (126 g) comprising of the title compound and a diastereoisomer. This material was purified by silica column chromatography eluting with a gradient of ethyl acetate:toluene (50:50 to 70:30) to afford the title compound as a viscous oil (90 g, 72%).

NMR (CDCl$_3$, selected data): 1.05 (d, 3H), 1.15 (s, 3H), 1.85–2.1 (m, 3H), 3.1–3.55 (m, 4H), 7.1–7.45 (m, 4H).

Preparation 82

(+)-3-(3-Bromophenyl)-trans-2,3-dimethyl-5-((methylsulfonyl)-oxy)pentyl methanesulfonate To a solution of (+)-3-(3-bromophenyl)-trans-2,3-dimethyl-1,5-pentanediol (Preparation 81, 467 g, 1.63 mol) in toluene (2.3 l) under an atmosphere of nitrogen was added triethylamine (362 g, 3.58 mol). The resultant clear solution was cooled to 0° C. and methanesulfonyl chloride (410 g, 3.58 moles) was slowly added over 1 h 30 min at such a rate that the internal temperature did not exceed 20° C. Once the addition was complete, the resultant mixture was stirred at room temperature for 18 h. Water (1.8 l) was added to the stirred solution, and the phases were separated. The aqueous phase was extracted with toluene (700 ml), and the extracts were combined to give a toluene solution of the title compound. In the present synthetic route the crude solution so formed was taken forward into the next step without any purification. However, purification, for example by concentration of this solution and subsequent silica column chromatography eluting with a gradient of ethyl acetate:hexane (10:90 to 50:50) affords the analytically pure title compound.

NMR (CDCl$_3$): 1.15 (d, 3H), 1.2 (s, 3H), 2.1–2.3 (m, 3H), 2.8 (s, 3H), 2.85 (s, 3H), 3.7–3.8 (m, 3H), 3.8–4.05 (m, 1H), 7.2–7.5 (m, 4H).

Preparation 83

(+)-4-(3-Bromophenyl)-N-hexyl-trans-3,4-dimethylpiperidine

To the crude toluene solution of (+)-3-(3-bromophenyl)-trans-2,3-dimethyl-5-((methylsulfonyl)oxy)pentyl methanesulfonate (Preparation 82, assume 1.63 mol in ca. 3 l) was added a solution of sodium carbonate (547 g, 4.1 mol) in water (1.4 l) followed by n-hexylamine (345 g, 3.42 mol). The resultant biphasic mixture was heated on a steam bath with stirring for 24 h. More n-hexylamine (82.3 g, 0.81 mol) was added, and the reaction was heated for a further 20 h. The mixture was allowed to cool, and water (1 l) was added. The resultant mixture was warmed to 40° C. and succinic anhydride (277 g, 2.76 mol) was added in portions over 15 min. Once the addition was complete, the reaction mixture was allowed to cool to room temperature and the phases were separated. The aqueous phase was extracted with toluene (1 l) and the combined extracts were washed with water (4 l) and saturated brine (4 l), and then concentrated in vacuo to give the crude title compound as a brown oil (ca 600 g). In the present synthetic route the crude product so formed was taken forward into the next step without any purification. However, purification, for example by silica column chromatography eluting with methanol:dichloromethane:0.880 ammonia (3:97:0.5) affords the analytically pure title compound.

NMR (CDCl$_3$, selected data for the free base): 0.9 (d, 3H), 0.95 (m, 3H), 1.2–1.65 (m, 13H), 1.9–2.05 (m, 1H), 2.15–2.2 (m, 3H), 2.45 (dd, 1H), 2.55 (br dd, 1H), 2.75–2.9 (m, 1H), 7.1–7.4 (m, 4H).

Preparation 84

(+)-4-(3-Aminophenyl)-N-hexyl-trans-3,4-dimethylpiperidine

To a solution of crude (+)-4-(3-bromophenyl)-N-hexyl-trans-3,4-dimethylpiperidine (Preparation 83, 12.56 g, 35.6 mmol) in deoxygenated toluene (75 ml) under an atmosphere of nitrogen was added benzophenone imine (7.75 g, 42.8 mmol), (R)-2,2'-bis(diphenylphosphino)-1,1'-binapthyl (33 mg, 0.054 mmol), sodium tert-butoxide (4.80 g, 49.9 mmol) and palladium acetate (8 mg, 0.036 mmol) and the mixture was heated under reflux for 20 h. The reaction mixture was cooled to room temperature and a solution of concentrated hydrochloric acid (26 ml) in water (120 ml) was added. The resultant biphasic mixture was heated under reflux for 4 h, before allowing to cool to room temperature. The layers were separated and the aqueous phase was washed with toluene (2×75 ml). The aqueous phase was cooled to 0° C., dichloromethane (75 ml) was added and the pH of the resultant mixture was adjusted to 12 by the addition of 40% w:v aqueous sodium hydroxide solution. The layers were separated, and the aqueous layer was extracted with dichloromethane (75 ml). The combined extracts were washed with water (75 ml), dried (MgSO$_4$), filtered and concentrated in vacuo to give the crude title compound. In the present synthetic route the crude product so formed was taken forward into the next step without any purification. However, purification, for example by silica column chromatography eluting with a gradient of diethyl ether:hexane:diethylamine (25:75:1 to 100:0:1) affords the analytically pure title compound.

NMR (CDCl$_3$, selected data for the free base): 0.8 (d, 3H), 0.9 (m, 3H), 1.1–1.7 (m, 13H), 1.95 (m, 1H), 2.2–2.4 (m, 3H), 2.45 (m, 1H), 2.55 (m, 1H), 2.7–2.85 (m, 1H), 3.6 (br s, 2H), 6.5 (m, 1H), 6.6 (br s, 1H), 6.7 (m, 1H), 7.1 (m, 1H).

What is claimed is:

1. A compound having the formula:

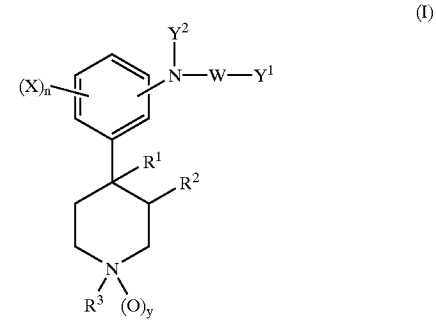

(I)

or pharmaceutically and veterinarily acceptable salts thereof wherein:

$R^1$ and $R^2$ are each independently H or $C_1$–$C_4$ alkyl; $R^3$ is $C_1$–$C_{10}$ alkyl, $C_3$–$C_{10}$ alkenyl, or $C_3$–$C_{10}$ alkynyl; wherein said alkyl, alkenyl or alkynyl group may optionally be substituted by one or more substituents independently chosen from:

OH; CN: one or more halo atoms; $C_1$–$C_6$ alkoxy; $C_1$–$C_6$ alkoxycarbonyl; $C_2$–$C_6$ alkanoyloxy; $C_3$–$C_8$ cycloalkyl; $C_3$–$C_8$ cycloalkoxy; $C_4$–$C_9$ cycloalkanoyl; aryl; aryloxy; aryl($C_1$–$C_4$)alkoxy; heteroaryl; a saturated heterocyclic group; adamantyl or ZBNRARS wherein Z is a direct bond, CO or S(O)$_p$ wherein p=0, 1, 2 and wherein B=(CH$_2$)$_m$ wherein m from 0 to 10 and wherein $R^4$ and $R^5$ are independently selected from H, $C_1$–$C_{10}$ alkyl, $C_3$–$C_{10}$ alkenyl, $C_3$–$C_{10}$ alkynyl, $C_3$–$C_8$ cycloalkyl, aryl or heteroaryl or wherein $R^4$ and $R^5$ represent unbranched $C_2$–$C_6$ alkylene groups which when taken together with the N to which they are bonded form a 4 to 7 memebered saturated heterocyclic ring optionally containing O, S, or N—R wherein said heterocyclic ring may be substituted by one or more $C_1$–$C_4$ alkyl groups and wherein $R^6$ is H, $C_1$–$C_6$ alkyl, $C_3$–$C_6$ cycloalkyl, —($C_1$–$C_6$ alkylene)($C_3$–$C_8$ cycloalkyl)or —($C_1$–$C_6$ alkylene)aryl and wherein when Z is a direct bond and m=0, then $R^3$ is not a terminal alkenyl or alkynyl;

W is $SO_2$, C=O, $P(Y^1)°O$ or $P(Y^1)$=S;

X is one or more substitiLents independently selected from H, halo, $C_1$–$C_4$ alkyl, $C_1$–$C_4$ alkoxy, halo ($C_1$–$C_4$) alkyl or halo($C_1$–$C_4$)alkoxy;

$Y^1$ is $C_1$-$C_{10}$ alkyl which may optionally be substituted by one or more halo atoms or by OH, $C_1$–$C_4$ alkoxy, $C_2$–$C_6$ alkanoyloxy, $CONH_2$, $NH_2$ or aryl; $NH_2$ or aryl; $NH_2$, mono- or di-($C_1$–$C_4$) alkylamino, $C_3$–$C_8$ cycloatkyl, aryl, phthalimidyl or heteroaryl;

$Y^2$ is H, $C_1$–$C_4$ alkyl, or $C_3$–$C_6$ alkenyl, wherein said alkyl or alkenyl groups may optionally be substituted by aryl, aryloxy or heteroaryl;

n is 0, 1 or 2;

y is 0 or 1, and wherein aryl is phenyl or naphthyl, and wherein aryl may optionally be substituted with 1 to 3 substituents, each independently selected from OH, $C_1$–$C_4$alkyl, $C_1$–$C_4$alkoxy, $C_1$–$C_4$ haloalkyl, $C_1$–$C_4$ haloalkoxy, $C_2$–$C_5$alkanoyl, halo, CN, $CH_2$, CN and $CONH_2$, and when W is $SO_2$, $R^1$ and $R^2$ cannot both be hydrogen.

2. Compounds according to claim 1 wherein $N(Y^2)(WY^1)$ is in the meta position, y=0, W=$SO_2$, $R^1$ and $R^2$ are $C_1$–$C_4$ alkyl groups with trans relative stereochemistry, or $R^1$ is a $C_1$–$C_4$ alkyl group and $R^2$ is hydrogen; $Y^2$ is hydrogen and wherein:

$Y^1$ is $C_1$–$C_{10}$ alkyl; imidazolyl or pyridyl; mono- or di-$C_1$–$C_3$ alkyl; phenyl; or $C_1$–$C_{10}$ alkyl substituted by $C_1$–$C_2$ alkoxy, or phenyl and wherein, $R^3$ is selected from: $C_4$–$C_{10}$ straight or branched chain alkyl; or;

$C_1$–$C_{10}$ alkyl substituted by: $C_5$–$C_6$ cycloalkyl, optionally substituted by one or more $C_1$–$C_4$ alkyl groups; $C_3$–$C_4$ alkoxy; $C_5$–$C_6$ cycloalkyloxy; aryloxy, optionally mono-substituted at the ortho position by chloro, or, at the ortho or para positions for fluoro, bromo, iodo, or at the ortho position for $C_1$–$C_2$ alkyl; aryl($C_1$–$C_2$) alkoxy; $C_5$–$C_6$ cycloalkanoyl; saturated 5- or 6-membered heterocyclic ring wherein the heteroatom(s) are at the 2- or 4-positions; or heteroaryl selected from isoxazolyl or indolyl; or;

$C_1$–$C_{10}$ alkyl substituted by: aryl, optionally substituted by one or more $C_1$–$C_4$ alkyl or halo groups or $CH_2CN$; $ZNR^4R^5$ wherein Z is carbonyl or a direct link, $R^4$ is hydrogen and $R^5$ is $C_5$–$C_6$ cycloalkyl; or $C_2$–$C_{10}$ alkyl substituted by hydroxy and $C_5$–$C_6$ cycloalkyl; or $C_3$–$C_{10}$ alkenyl; or $C_3$–$C_4$ alkenyl substituted by: $C_5$–$C_6$ cycloalkyl; aryl; or $C_3$–$C_{10}$ alkynyl.

3. Compounds according to claim 1 wherein $R^1$ and $R^2$ are methyl groups with trans relative stereochemistry.

4. Compounds according to claim 1 wherein $R^1$ is propyl and $R^2$ is hydrogen.

5. Compounds claim 1 wherein $N(Y^2)(WY^1)$ is in the meta position, y is zero, n is zero, W=$SO_2$, $R^1$ and $R^2$ are methyl groups with trans relative stereochemistry; $Y^2$ is hydrogen and wherein $Y^1$ is methyl, ethyl, propyl, 1-methylethyl or butyl; imidazolyl or pyridinyl or N-isopropylamino and wherein $R^3$ is selected from: hexyl; methyl-hexyl; or ethyl or propyl substituted by: cyclohexyl; cyclohexanoyl; 2-tetrahydropyranyl or methyl, ethyl or propyl, substituted by: phenyl; or 3-cyclohexyl-3-hydroxypropyl; or prop-2-enyl substituted by cyclohexyl or phenyl.

6. Compounds according to claim 1 wherein $Y^1$ is selected from: methyl, ethyl, propyl, 1-methylethyl, butyl, 3-pyridinyl, 1-methyl-1H-imidazol-4-yl and N-isopropylamino.

7. Compounds according to claim 1 wherein $R^3$ is selected from: N-hexyl, N-(5-methylhexyl), N-(3-cyclohexylpropyl), N-benzyl, N-(3-phenylpropyl), N-(3-cyclohexyl-3-oxopropyl), N-(2-(3-methylphenyl)ethyl), N-(1-(4-ethylphenyl)methyl), N-(2-(2-methylphenyl)ethyl), N-(3-(2-methylphenyl)propyl), N-(3-(tetrahydropyran-2-yl)propyl), N-((S)-3-cyclohexyl-3-hydroxy propyl), N-((E)-3-cyclohexylprop-2-enyl) and N-cinnamyl.

8. Compounds according to claim 1 wherein $Y^1$ is selected from methyl, ethyl, propyl and wherein $R^3$ is: hexyl or 5-methylhexyl; or methyl or ethyl substituted by phenyl, substituted methyl or ethyl; or propyl substituted by phenyl.

9. Compounds according to any claim 1 wherein $Y^1$ is selected from methyl, ethyl or propyl.

10. Compounds according to claim 1 wherein $R^3$ is selected from: N-hexyl, N-(5-methylhexyl), N-benzyl, N-(3-phenylpropyl), N-(2-(3-methylphenyl)ethyl), N-(2-(2methylphenyl)ethyl) and N-(3-(2-methylphenyl) propyl).

11. Compounds according to claim 1 selected from:

(±)-4-(3-ethanesulfonylaminophenyl)-N-hexyl-trans-3,4-dimethylpiperidine, (+)-4-(3-ethanesulfonylaminophenyl)-N-hexyl-trans-3,4-dimethylpiperidine, (±)-4-(3-ethanesulfonylaminophenyl)-trans-3,4-dimethyl-N-(5-methylhexyl)piperidine, (±)-trans-3,4-dimethyl-N-(5-methylhexyl)-4-(3-propanesulfonylaminophenyl)piperidine, (±)-N-hexyl-trans-3,4-dimethyl-4-(3-propanesulfonylaminophenyl)piperidine, (±)-N-benzyl-trans-3,4-dimethyl-4-(3-propanesulfonylaminophenyl)piperidine, (±)-trans-3,4-dimethyl-N-(3-phenylpropyl)-4-(3-propanesulfonylaminophenyl)piperidine, (±)-4-(3-methanesulfonylaminophenyl)-trans-3,4-dimethyl-N-(5-methylhexyl)piperidine, (±)-N-hexyl-4-(3-methanesulfonylaminophenyl)-trans-3,4-dimethylpiperidine, (±)-4-(3-methanesulfonylaminophenyl)-trans-3,4-dimethyl-N-(2-(3-methylphenyl)-ethyl)piperidine, (±)-4-(3-methanesulfonylaminophenyl)-trans-3,4-dimethyl-N-(3-phenylpropyl)piperidine, (±)-4-(3-methanesulfonylaminophenyl)-trans-3,4-dimethyl-N-(2-(2-methylphenyl)ethyl)piperidine and (±)-4-(3-methanesulfonylaminophenyl)-trans-3,4-dimethyl-N-(3-(2-methylphenyl)propyl)piperidine and pharmaceutical salts thereof.

12. A process for the formation of compounds and salts having the formula (I):

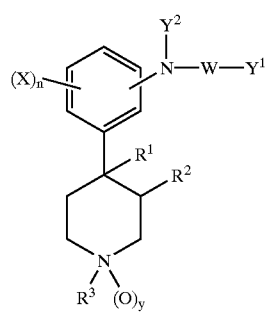

(I)

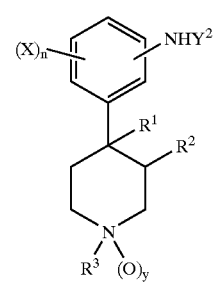

(IIa)

wherein $R^1$, $R^2$, $R^3$, X, $Y^2$ and n are as defined above, by reaction with either a group of the formula Q—W—$Y^1$, in the presence of a base, wherein W and $Y^1$ are as defined above and Q is a leaving group; or with an anhydride of the formula $(Y^1W)_2O$ in the presence of a base.

13. A process for the preparation of compounds and salts having the formula (I):

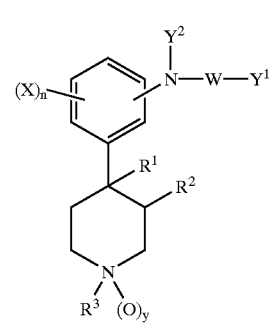

(I)

wherein: $R^1$ and $R^2$ are each independently H or $C_1$–$C_4$ alkyl; $R^3$ is $C_1$–$C_{10}$ alkyl, $C_3$–$C_{10}$ alkenyl, or $C_3$–$C_{10}$ alkynyl; wherein said alkyl, alkenyl or alkynyl group may optionally be substituted by one or more substituents independently chosen from:

wherein: $R^1$ and $R^2$ are each independently H or $C_1$–$C_4$alkyl; $R^3$ is $C_1$–$C_{10}$ alkyl, $C_3$–$C_{10}$ alkenyl, or $C_3$–$C_{10}$ alkynyl; wherein said alkyl, alkenyl or alkynyl group may optionally be substituted by one or more substituents independently chosen from:

OH; CN; one or more halo atoms; $C_1$–$C_6$ alkoxy; $C_1$–$C_6$ alkoxycarbonyl; $C_2$–$C_6$ alkanoyl; $C_2$–$C_6$ alkanoyloxy; $C_3$–$C_8$ cycloalkyl; $C_3$–$C_8$ cycloalkoxy; $C_4$–$C_9$ cycloalkanoyl; aryl; aryloxy; aryl($C_1$–$C_4$)alkoxy; heteroaryl; a saturated heterocyclic group; adamantyl or $ZBNR^4R^5$ wherein Z is a direct bond, CO or $S(O)_p$ wherein p=0, 1, 2 and wherein B=$(CH_2)_m$, wherein m=from 0 to 10 and wherein $R^4$ and $R^5$ are independently selected from H, $C_1C_{10}$ alky, $C_3$–$C_{10}$ alkenyl, $C_3$–$C_{10}$ alkenyl, $C_3$–$C_8$ cycloalkyl, aryl or heteroaryl or wherein $R^4$ and $R^5$ represent unbranched $C_2$–$C_6$ alkylene groups which when taken together with the N to which they are bonded form a 4 to 7 membered saturated heterocyclic ring optionally containing O, S or N—$R^6$ wherein said heterocyclic ring may be substituted by one or more $C_1$–$C_4$ alkyl groups and wherein $R^6$ is H, $C_1$–$C_6$ alkyl, $C_3$–$C_8$ cycloalkyl, —($C_1$–$C_6$ alkylene)($C_3$–$C_8$ cycloalkyl) or —($C_1$–$C_6$ alkylene)aryl and wherein when Z is a direct bond and m=0, then $R^3$ is not a terminal alkenyl or alkynyl;

W is $SO_2$, C=O, $P(Y^1)$=O or $P(Y^1)$=S;

X is one or more substitutents independently selected from H, halo, $C_1$–$C_4$ alkyl, $C_1$–$C_4$ alkoxy, halo ($C_1$–$C_4$) alkyl or halo($C_1$–$C_4$)alkoxy;

$Y^1$ is $C_1$–$C_{10}$ alkyl which may optionally be substituted by one or more halo atoms or by OH, $C_1$–$C_4$ alkoxy, $C_2$–$C_6$ alkanoyloxy, $CONH_2$, $NH_2$ or aryl; $NH_2$, mono or di-($C_1$–$C_4$) alkylamino, $C_3$–$C_8$ cycloalkyl, aryl, phthalimidyl or heteroaryl;

$Y^2$ is H, $C_1$–$C_4$ alkyl, or $C_3$–$C_6$ alkenyl, wherein said alkyl or alkenyl groups may optionally be substituted by aryl, aryloxy or heteroaryl;

n is 0, 1 or 2; and y is 0 or 1.

said process comprising reacting a compound having the formula (IIa):

OH; CN; one or more halo atoms; $C_1$–$C_6$ alkoxy; $C_1$–$C_6$ alkoxycarbonyl; $C_2$–$C_6$ alkanoyl; $C_2$–$C_6$ alkanoyloxy; $C_3$–$C_8$ cycloalkyl; $C_3$–$C_8$ cycloalkoxy; $C_4$–$C_9$ cycloalkanoyl; aryl; aryloxy; aryl($C_1$–$C_4$)alkoxy; heteroaryl; a saturated heterocyclic group; adamantyl or $ZBNR^4R^5$ wherein Z is a direct bond, CO or $S(O)_p$ wherein p=0, 1, 2 and wherein B=$(CH_2)_m$ wherein m=from 0 to 10 and wherein $R^4$ and $R^5$ are independently selected from H, $C_1$–$C_{10}$ alkyl, $C_3$–$C_{10}$ alkenyl, $C_3$–$C_{10}$ alkynyl, $C_3$–$C_8$ cycloalkyl, aryl or heteroaryl or wherein $R^4$ and $R^5$ represent unbranched $C_2$–$C_6$ alkylene groups which when taken together with the N to which they are bonded form a 4 to 7 membered saturated heterocyclic ring optionally containing O, S or N—$R^6$ wherein said heterocyclic ring may be substituted by one or more $C_1$–$C_4$ alkyl groups and wherein $R^6$ is H, $C_1$–$C_6$ alkyl, $C_3$–$C_8$ cycloalkyl, —($C_1$–$C_6$ alkylene)($C_3$–$C_8$ cycloalkyl) or —($C_1$–$C_6$ alkylene)aryl and wherein when Z is a direct bond and m=0, then $R^3$ is not a terminal alkenyl or alkynyl;

W is $SO_2$, C=O, $P(Y^1)$=O or $P(Y^1)$=S;

is one or more substituents independently selected from H, halo, $C_1$–$C_4$ alkyl, $C_1$–$C_4$ alkoxy, halo ($C_1$–$C_4$) alkyl or halo($C_1$–$C_4$)alkoxy;

Y¹ is $C_1$–$C_{10}$ alkyl which may optionally be substituted by one or more halo atoms or by OH, $C_1$–$C_4$ alkoxy, $C_2$–$C_6$ alkanoyloxy, $CONH_2$, $NH_2$ or aryl; $NH_2$, mono or di-($C_1$–$C_4$)-alkylamino, $C_3$–$C_8$ cycloalkyl, aryl, phthalimidyl or heteroaryl;

Y² is H, $C_1$–$C_4$ alkyl, or $C_3$–$C_6$ alkenyl, wherein said alkyl or alkenyl groups may optionally be substituted by aryl, aryloxy or heteroaryl;

n is 0, 1 or 2; and y is 0 or 1;

said process comprising reaction of a compound of formula (IIIa):

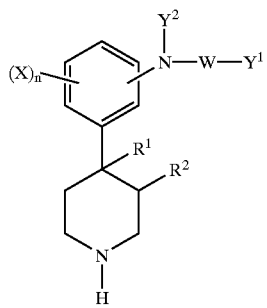

(IIIa)

wherein $R^1$, $R^2$, $Y^1$, $Y^2$, W, X and n are as defined above, with a compound of formula $R^3$—X, wherein $R^3$ is as defined above and wherein X is chloro, bromo, iodo or a suitable leaving group.

14. A process according to claim 12 or 13 for the preparation of compound of the formula (Ib):

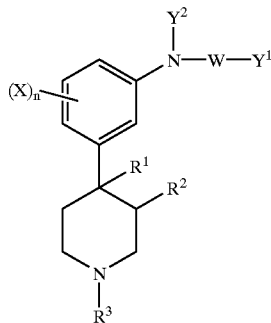

(Ib)

wherein $N(Y^2)(WY^1)$ is in the meta position and y is zero.

15. A process according to claim 12 or 13 wherein the compound having formula (I) is a compound having the general formula (XXIV):

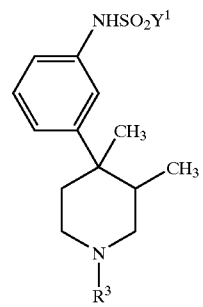

(XXIV)

wherein $Y^1$ is methyl, ethyl or propyl and $R^3$ is selected from: N-hexyl, N-(5-methylhexyl), N-benzyl, N-(3-phenylpropyl), N-(2-(3-methylphenyl)ethyl), N-(2-(2-methylphenyl)ethyl) or N-(3-(2-methylphenyl)propyl) and wherein the compound having formula (II) is a compound having the formula (XXIII):

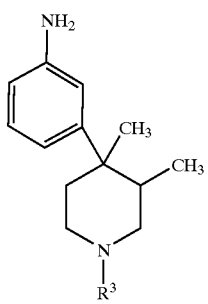

(XXIII)

wherein the reagents are $(Y^1SO_2)_2O$ or $Y^1SO_2Cl$.

16. A process according to claim 12 or 13 wherein the molar ratio of $(Y^1SO_2)_2O$ or $Y^1SO_2Cl$ to compound (XXIII) is at least 2:1 and wherein the reaction of compound (XIII) with $(Y^1SO_2)_2O$ or $Y^1SO_2Cl$ is followed by alkaline hydrolysis.

17. A process claim 12 or 13 wherein compounds having the formula (I) are subsequently converted to a salt and recrystallised.

18. A process claim 12 or 13 wherein the compound having the formula (I) is a compound having the general formula (XXIV) as defined in claim 15 and wherein the salt formed is the (+)- or (−)-camphorsulfonic acid salt.

19. A process for the formation of compounds having the formula (II) comprising hydrolysing compounds having the general formula (XIV):

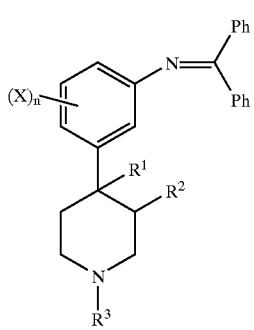

(XIV)

wherein $R^1$, $R^2$, $R^3$, X and n are as defined for the compound of formula (I) in claim 12 with the proviso that the $R^3$ group is not substituted by CN or $C_1$–$C_6$ alkoxycarbonyl and wherein y and $N(Y^2)(WY^1)$ are as defined in claim 14.

20. A process for the formation of compounds having the formula (XIV) as defined in claim 19 comprising reaction of a compound of general formula (XIII):

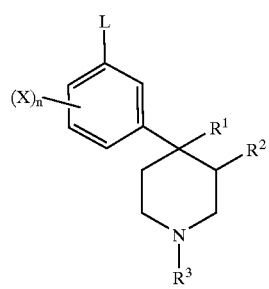

(XIII)

wherein L is a bromo, iodo, or $OSO_2CF_3$ group and wherein $R^1$, $R^2$, $R^3$, X and n are as defined for a compound of formula (I) in claim 12 with the proviso that the $R^3$ group is not substituted by CN or $C_1$–$C_6$ alkoxycarbonyl and wherein y is zero with the proviso that $(X)_n$ is not a bromo or iodo group, said reaction comprising reacting a compound of general formula (XIII) with benzophenone imine in the presence of a palladium catalyst and a base.

21. A process according to claims 19 and 20 wherein the compounds having the formula (II) are formed from compounds having the formula (XIII) by:

a) reaction with benzophenone imine in the presence of a palladium catalyst, a ligand, and base to form a compound of general formula (XIV); followed by b) acid hydrolysis; and wherein the intermediate compound having the formula (XIV) is not isolated.

22. A process according to claim 19 or 20 wherein the base is sodium tertiary butoxide or caesium carbonate.

23. A process according to any of claim 19 or 20 wherein the compound having the general formula (XIII) is a compound having the general formula (XXII):

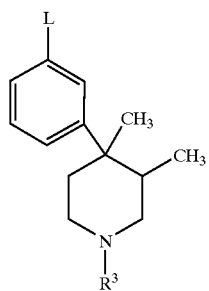

(XXII)

wherein L is a bromo or iodo group and $R^3$ is as defined in claim 12 and wherein the reaction is carried out with palladium diacetate, (R)-(+)-2,2'-bis (diphenylphosphino)-1,1'-binaphthyl, benzophenone imine and sodium tertiary butoxide in toluene followed by acid hydrolysis to form a compound having the general formula (XXIII) as defined in claim 15.

24. A process according to claim 19 for the formation of compounds having the formula (II) as defined in claim 12 wherein y is zero and wherein the $NHY^2$ group is in the meta position from compounds having the general formula (XXV) via compounds having the formula (XIV) as defined in claim 19:

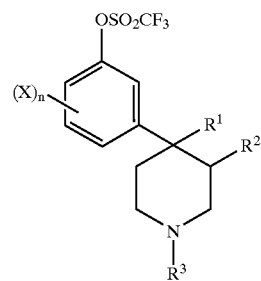

(XXV)

wherein $R^1$, $R^2$, $R^3$, X and n are as defined for the compounds of general formula (I) in claim 12, with the proviso that the $R^3$ group is not substituted by CN or $C_1$–$C_6$ alkoxycarbonyl, which are in turn prepared from the corresponding alcohols having the formula (V).

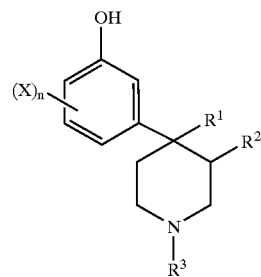

(V)

wherein $R^1$, $R^{2,}$ $R^3$, X and n are as defined in claim 12.

25. A process for the formation of compounds having the formula (II) as defined in claim 12 wherein y is zero via reduction of compounds having the general formula (XIII) wherein L is —$NO_2$.

26. A process for the formation of compounds having the formula (XIII), as defined in claim 15 from compounds having the formula (XII):

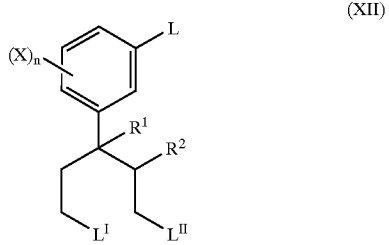

(XII)

wherein L is a bromo, iodo, —$NO_2$ or —$OR^{15}$ group, and wherein $R^1$, $R^2$, $R^3$, X and n are as defined for a compound of general formula (I) in claim 12 with the provisos that: the $R^3$ group is not substituted by $C_1$–$C_6$ alkoxycarbonyl, $C_2$–$C_6$ alkanoyl or $C_2$–$C_6$ alkanoyloxy, or by $ZBNR^4R^5$ wherein Z is CO; when L is bromo or iodo $(X)_n$ is not a bromo, iodo; when L is —$OR^{15}$, $(X)_n$ is not a bromo, iodo or alkoxy group, and wherein L' and L" are leaving groups derived from alcohol which are displaceable by an amine selected from alkyl or arylsulfonate or halo and wherein $R^{15}$ is a $C_1$–$C_4$ alkyl group;

said reaction comprising reaction of a compound having formula (XII) with an amine of the formula $NH_2R^3$ or $NH_3$ wherein $R^3$ is as defined in claim 12.

27. A process according to claim 26 wherein L' and L" are each independently selected from alkyl sulfonyloxy, aryl sulfonyloxy or halogen.

28. A process according to claim 26 wherein the compound having the formula (XII) is a compound having the formula (XXI):

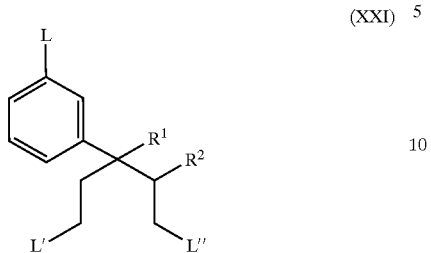

(XXI)

wherein L is a bromo or iodo group and wherein L' and L" are as defined in claim 26 and wherein the reaction is carried out with n-hexylamine, aqueous sodium carbonate and toluene to provide compounds having the general formula (XXII) as defined in claim 23.

29. A process for the formation of a compound having formula (XII) as defined in any of claim 25 comprising reacting a compound having the general formula (XI):

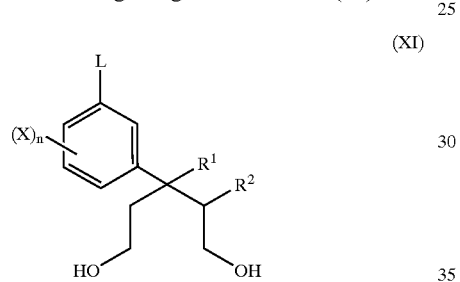

(XI)

wherein $R^1$, $R^2$, L, X and n are as defined in claim 26; with a) an alkyl or arylsulfonylhalide or anhydride in the presence a base in an inert solvent; and, optionally, b) conversion of the diol (XI) to its corresponding dihalo derivative.

30. A process for the formation of a diol having general formula (XI) as defined in claim 29 from a γ,δ unsaturated acid having the general formula (X):

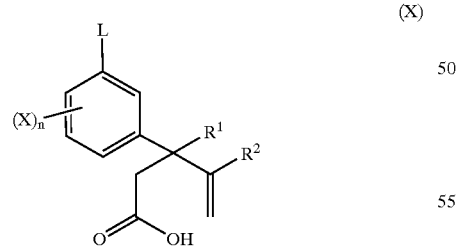

(X)

wherein $R^1$, $R^2$, L, X and n are as defined in claim 26;

said process comprising reduction of the acid group and concomitant hydroboration of the alkene group followed by subsequent oxidative work-up provides the diol (XI).

31. A process according to claim 30 wherein the acid having the formula (X) is a compound having the general formula (XIX):

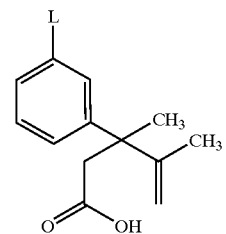

(XIX)

wherein L is a bromo or iodo group and wherein hydroboration of (XIX) with diborane in tetrahydrofuran followed by treatment with aqueous sodium percarbonate provides compounds having the general formula (XX):

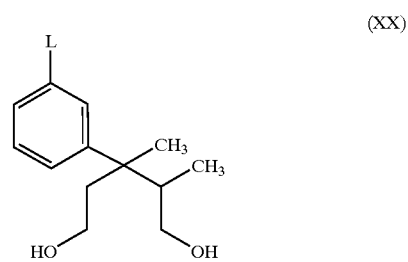

(XX)

wherein L is as defined above.

32. A process for the formation of compounds having the formula (X), as defined in claims 30 and 31, by alkaline hydrolysis of compounds having the general formula (IX):

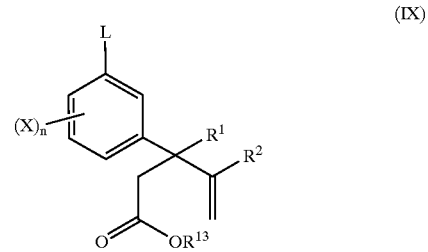

(IX)

wherein L is a bromo or iodo group and wherein $R^1$, $R^2$ L, X and n are as defined in claim 26 and wherein $R^{13}$ is a $C_1$–$C_4$ alkyl group.

33. A process for the formation of a compound having the formula (IX) as defined in claim 32 from a compound having general formula (VIII):

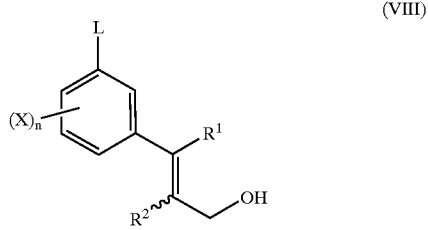

(VIII)

wherein $R^1$, $R^2$, L, X and n are as defined in claim 26;

said process comprising reacting (VII) with a compound of the formula $MeC(OR^{13})_3$ wherein $R^{13}$ is $C_1$–$C_4$ alkyl or aryl, with subsequent thermal rearrangement to furnish compounds having the general formula (IX).

34. A process according to claim 33 wherein the compound having the formula (VII) is a compound having the general formula (XVI):

(XVI)

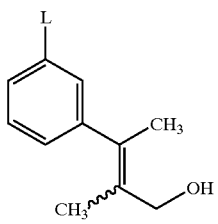

wherein L is a bromo or iodo group and wherein said compound (XVI) is reacted with $CH_3C(OCH_3)_3$ to provide an intermediate compound having the general formula (XVII):

(XVII)

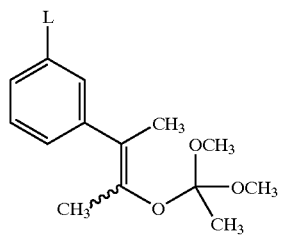

wherein L is a bromo or iodo group and wherein compound (XVII) rearranges upon heat treatment to provide a compound having the general formula (XVIII).

(XVIII)

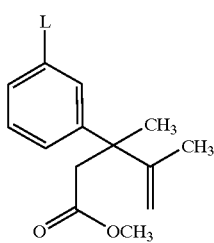

35. A process for the formation of compounds having the formula (VIII), as defined in claims 33 and 34, from compounds having the general formula (VII):

(VII)

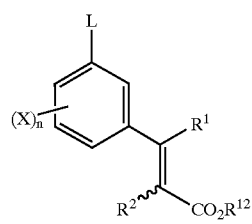

wherein $R^1$, $R^2$, L, X and n are as defined in claim 26 and wherein $R^{12}$ is a $C_1$–$C_4$ alkyl group; comprising reduction of the α,β unsaturated ester group via reaction with a metal hydride in an inert solvent.

36. A process according to claim 35 wherein the compound having the formula (VII) is a compound having the general formula (XV):

(XV)

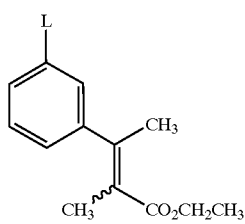

wherein L is a bromo or iodo group.

37. A process according to any of claim 12 wherein an optional separation of -cis and -trans geometric isomers of compounds having the formulae (VII), (VIII), (XV) or (XVI) is carried out using chromatographic techniques and wherein an optional optical resolution of the —(R) and —(S) isomers of compounds having the general formulae (X) or (XIX) is carried out via treatment with a chiral amine followed by recrystallisation; and wherein an optional separation of -cis and -trans diastereoisomers of diols having the general formulae (XI) or (XX) is carried out via recrystallisation or chromatographic techniques; and wherein an optional resolution of the racemic mixture of compounds having the general formulae (I), with the proviso that y is zero, or (XXIV) is carried out via recrystallisation or chromatographic techniques.

38. A process according to claim 12 wherein compounds of the formulae (I) or (XXIV) are treated with (+) or (–) camphorsulfonic acid (CSA) followed by resolution of the resultant diastereomeric (+) and (–) CSA salts.

39. A process according to any of claim 12 wherein no resolution is performed throughout and wherein separation of the enantiomers diastereoisomers of formula (I) is accomplished via chiral phase HPLC.

40. A pharmaceutical composition comprising a compound of formula (I), of claim 1 or a pharmaceutically acceptable salt thereof, together with a pharmaceutically acceptable diluent or carrier.

41. A method of treating pruritus in a human or animal which comprises administering a therapeutically effective amount of a compound of formula (I), of claim 1 or a pharmaceutically or veterinarily acceptable salt thereof.

* * * * *